US008841318B2

(12) United States Patent
Arvanitis et al.

(10) Patent No.: US 8,841,318 B2
(45) Date of Patent: Sep. 23, 2014

(54) SUBSTITUTED HETEROCYCLES AS JANUS KINASE INHIBITORS

(71) Applicant: Incyte Corporation, Wilmington, DE (US)

(72) Inventors: Argyrios G. Arvanitis, Kennett Square, PA (US); James D. Rodgers, Landenberg, PA (US); Louis Storace, Middletown, DE (US); Beverly Folmer, Hockessin, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 13/834,040

(22) Filed: Mar. 15, 2013

(65) Prior Publication Data

US 2013/0274257 A1 Oct. 17, 2013

Related U.S. Application Data

(63) Continuation of application No. 11/961,424, filed on Dec. 20, 2007, now Pat. No. 8,513,270.

(60) Provisional application No. 60/928,205, filed on May 8, 2007, provisional application No. 60/876,705, filed on Dec. 22, 2006.

(51) Int. Cl.
*C07D 471/14* (2006.01)
*C07D 487/04* (2006.01)
*C07D 487/14* (2006.01)
*A61K 31/437* (2006.01)

(52) U.S. Cl.
CPC ............. *C07D 487/14* (2013.01); *A61K 31/437* (2013.01); *C07D 471/14* (2013.01); *C07D 487/04* (2013.01)
USPC ............................................ 514/292; 546/85

(58) Field of Classification Search
CPC ............................ A61K 31/437; C07D 471/04
USPC .......................................... 546/85; 514/292
See application file for complete search history.

(56) References Cited

U.S. PATENT DOCUMENTS

| | | | |
|---|---|---|---|
| 5,521,184 A | 5/1996 | Zimmermann | |
| 6,335,342 B1 | 1/2002 | Longo et al. | |
| 6,486,322 B1 | 11/2002 | Longo et al. | |
| 6,579,882 B2 | 6/2003 | Stewart et al. | |
| 7,005,436 B2 | 2/2006 | Lloyd et al. | |
| 7,598,257 B2 | 10/2009 | Rodgers et al. | |
| 8,119,655 B2 * | 2/2012 | Dong et al. ............. | 514/292 |
| 2003/0165576 A1 | 9/2003 | Fujii et al. | |
| 2004/0009983 A1 | 1/2004 | Cox et al. | |
| 2004/0198737 A1 | 10/2004 | Cox et al. | |
| 2005/0153989 A1 | 7/2005 | Grotzfeld et al. | |
| 2006/0106020 A1 | 5/2006 | Rodgers et al. | |
| 2006/0183761 A1 | 8/2006 | Ledeboer et al. | |
| 2006/0183906 A1 | 8/2006 | Rodgers et al. | |
| 2007/0135461 A1 | 6/2007 | Rodgers et al. | |
| 2007/0149506 A1 | 6/2007 | Arvanitis et al. | |
| 2008/0312258 A1 | 12/2008 | Rodgers et al. | |
| 2008/0312259 A1 | 12/2008 | Rodgers et al. | |
| 2009/0181959 A1 | 7/2009 | Rodgers et al. | |
| 2009/0197869 A1 | 8/2009 | Arvanitis et al. | |
| 2009/0215766 A1 | 8/2009 | Rodgers et al. | |
| 2009/0233903 A1 | 9/2009 | Rodgers et al. | |
| 2009/0318405 A1 | 12/2009 | Li et al. | |
| 2010/0022522 A1 | 1/2010 | Rodgers et al. | |

FOREIGN PATENT DOCUMENTS

| | | |
|---|---|---|
| DE | 30 36 390 | 5/1982 |
| WO | WO 97/02262 | 1/1997 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/53595 | 9/2000 |
| WO | WO 01/14402 | 3/2001 |
| WO | WO 01/42246 | 6/2001 |
| WO | WO 01/64655 | 9/2001 |
| WO | WO 02/00196 | 1/2002 |
| WO | WO 02/00661 | 1/2002 |
| WO | WO 02/055084 | 7/2002 |
| WO | WO 02/060492 | 8/2002 |
| WO | WO 02/096909 | 12/2002 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/099771 | 12/2003 |
| WO | WO 2004/005281 | 1/2004 |
| WO | WO 2004/041814 | 5/2004 |
| WO | WO 2004/046120 | 6/2004 |

(Continued)

OTHER PUBLICATIONS

"INCB18424 Discussion" Presentation at the American Society of Hematology, 49th Annual Meeting and Exposition, Atlanta, GA. Abstract #558, Dec. 10, 2008.
26$^{th}$ Annual JPMorgan Healthcare Conference presentation dated Jan. 8, 2008.
Adv Pharmacol. 2000;47:113-74.
Agents Actions. Jan. 1993;38(1-2):116-21.
Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.
Bioreversible Carriers in Drug Design, ed. Edward B. Roche, American Pharmaceutical Association and Pergamon Press, 1987.

(Continued)

*Primary Examiner* — Erich A Leeser
(74) *Attorney, Agent, or Firm* — Fish & Richardson P.C.

(57) ABSTRACT

The present invention provides substituted tricyclic heteroaryl compounds, including, for example, pyridoindoles, pyrimidinoindoles and triazinoindoles that modulate the activity of Janus kinases and are useful in the treatment of diseases related to activity of Janus kinases such as immune-related diseases, skin disorders, myeloid proliferative disorders, cancer, and other diseases.

14 Claims, No Drawings

(56) References Cited

FOREIGN PATENT DOCUMENTS

| WO | WO 2004/047843 | 6/2004 | | |
|---|---|---|---|---|
| WO | WO 2004/056786 | 7/2004 | | |
| WO | WO 2004/072063 | 8/2004 | | |
| WO | WO 2004/080980 | 9/2004 | | |
| WO | WO 2004/099204 | 11/2004 | | |
| WO | WO 2004/099205 | 11/2004 | | |
| WO | WO 2005/013986 | 2/2005 | | |
| WO | WO 2005/028444 | 3/2005 | | |
| WO | WO 2005/037825 | 4/2005 | | |
| WO | WO 2005/051393 | 6/2005 | | |
| WO | WO 2005/060972 | 7/2005 | | |
| WO | WO 2005/095400 | 10/2005 | | |
| WO | WO 2005/105146 | 11/2005 | | |
| WO | WO 2005/105814 | 11/2005 | | |
| WO | WO 2005/105988 | 11/2005 | | |
| WO | WO 2005/110410 | 11/2005 | | |
| WO | WO 2005/121130 | 12/2005 | | |
| WO | WO 2006/013114 | 2/2006 | | |
| WO | WO 2006/046023 | 5/2006 | | |
| WO | WO 2006/046024 | 5/2006 | | |
| WO | WO 2006/056399 | 6/2006 | | |
| WO | WO 2006/096270 | 9/2006 | | |
| WO | WO 2006/116733 | 11/2006 | | |
| WO | WO 2006/127587 | 11/2006 | | |
| WO | WO 2007/025090 | 3/2007 | | |
| WO | WO 2007/041130 | 4/2007 | | |
| WO | WO 2007/044779 | * | 4/2007 | ........... C07D 471/04 |
| WO | WO 2007/076423 | 7/2007 | | |
| WO | WO 2007/084557 | 7/2007 | | |
| WO | WO 2007/117494 | 10/2007 | | |

OTHER PUBLICATIONS

Blume-Jensen P et al, Nature 2001, 411(6835):355-365.
Bolen JB. Nonreceptor tyrosine protein kinases. Oncogene. 1993, 8(8):2025-31.
Borie, D.C. et al., Transplantation. Dec. 27, 2005;80(12):1756-64.
Boudny, V., and Kovarik, J., Neoplasm. 49:349-355, 2002.
Bowman, T., et al. Oncogene 19:2474-2488, 2000.
Burger, R., et al. Hematol J. 2:42-53, 2001.
Candotti, F., L. Notarangelo, et al. (2002). "Molecular aspects of primary immunodeficiencies: lessons from cytokine and other signaling pathways." J Clin Invest 109(10): 1261-9.
Candotti, F., S. A. Oakes, et al. (1997). "Structural and functional basis for JAK3-deficient severe combined immunodeficiency." Blood 90(10): 3996-4003.
Cetkovic-Cvrlje, M., A. L. Dragt, et al. (2003). "Targeting JAK3 with JANEX-1 for prevention of autoimmune type 1 diabetes in NOD mice." Clin Immunol 106(3): 213-25.
Chalandon et al., Haematologica (2005), 90(7):949-968.
Chalandon, Yves, and Schwaller, Jürg, "Targeting mutated protein tyrosine kinases and their signaling pathways in hematologic malignancies." Hematologica, 90:949-968.
Changelian, P.S. et al. Science, 2003, 302, 875-878.
Chen, C.L. et al., "Stat3 Activation in Human Endometrial and Cervical Cancer", *British journal of Cancer*, 96,, 591-599, 2007.
Communication pursuant to Article 94(3) EPC for EP 2121692 (App. No. 07 855 296.5-2117) dated May 17, 2010.
Conklyn, M. et al., Journal of Leukocyte Biology, 2004, 76, 1248-1255.
International Search Report for PCT/US2007/088357, dated Mar. 20, 2008.
Current Protocols in Immunology, vol. 3., Coligan, J.E. et al, Wiley Press.
Daniels et al., "Imatinib mesylate inhibits the profibrogenic activity of TGF-β and prevents bleomycinmediated lung fibrosis." J. Clin. Invest., 114(9):1308-1316, Nov. 2004.
De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol 109(4): 823-8.
Deuse, T. et al., Transplantation, 2008, 85(6) 885-892.
Doleschall G., and Lempert, K. "Thermal and Acid Catalysed Degradations of 3-Alkylthio-6,7-Dihydro-[I.2.4]Triazino[1.6-c]Quinazolin-5-IUM-I-Olates." Tetrahedron, 30:3997-4012, 1974.
Dudley, A.C. et al. Biochem. J. 2005, 390(Pt 2):427-36.
E. Quesada et al, Tetrahedron, 62 (2006) 6673-6680.
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007.
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285.
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007.
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov 8-10, 2007. Poster 0009.
Gone, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303.
Gottlieb et al., Nat. Rev. Drug Disc., 4:19-34.
Gottlieb, A.B., et al, Nat Rev Drug Disc., 4:19-34.
Hubschwerlen, c. et al., "Piramido[1,6-a]benzimidazoles: A New Class of DNA Gurase Inhibitors", *J. med. Chem.*, 35, 1385-1392, 1992. XP-002309406.
Immunol Today. Jan. 1998;19(1):37-44.
International Preliminary Report on Patentability received in International Application No. PCT/US2007/088357, dated Jun. 24, 2009.
Ishizaki, T. et al. Molecular Pharmacology, 2000, 57, 976-983.
Itagaki, Noriaki; Kimura, Man; Sugahara, Tsutomu; Iwabuchi, Yoshiharu. (Organic Letters 2005; 7(19); 4181-4183.
James, C., et al. Nature 434:1144-1148.
Journal of Pharmaceutical Science, 66, 2 (1977).
Kawamura, M., D. W. McVicar, et al. (1994). "Molecular cloning of L-JAK, a Janus family protein-tyrosine kinase expressed in natural killer cells and activated leukocytes." Proc Natl Acad Sci U S A 91(14): 6374-8).
Kharas, Michael, and Fruman, David, "ABL Oncogenes and Phosphoinositide 3-Kinase: Mechanism of Activation and Downstream Effectors." Cancer Res., 65(6):2047-2053, Mar. 15, 2005.
Kruh et al., "The complete coding sequence of arg defines the Abelson subfamily of cytoplasmic tyrosine kinases." Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, E. et al. European Journal of Pharmacology 582 (2008) 154-161.
Levine, et al., Cancer Cell, vol. 7, 2005: 387-397.
Madhusudan S, Ganesan TS. Tyrosine kinase inhibitors in cancer therapy. Clin Biochem. 2004, 37(7):618-35.
Manning, G. et al., Science. 2002, 298(5600):1912-1934.
Methods in Molecular Biology: vol. 225, Inflammation Protocols., Winyard, P.G. and Willoughby, D.A., Humana Press, 2003.
Milici, A.J., et al., Arthritis Research & Therapy 2008, 10:R14 (http://arthritis-research.com/content/10/1/R14).
Nakagawara, Akira, "Trk receptor tyrosine kinases: A bridge between cancer and neural development." Cancer Letters, 169:107-114, 2001.
Neubauer, H., A. Cumano, et al. (1998). Cell 93(3): 397-409.
Nishio, M. et al. FEBS Letters, 1999, 445, 87-91.

(56) References Cited

OTHER PUBLICATIONS

O'Hare et al., "Targeted CML therapy: controlling drug resistance, seeking cure", Current Opinion in Genetics & Development 16:92-99 (2006).
Ortmann, R. A., T. Cheng, et al. (2000). "Janus kinases and signal transducers and activators of transcription: their roles in cytokine signaling, development and immunoregulation." Arthritis Res 2(1): 16-32.
Palmer, Amparo, and Klein, Rudiger, "Multiple roles of ephrins in morphogenesis, neuronal networking, and brain function." *Genes & Dev.*, 17:1429-1450, 2003.
Parganas, E., D. Wang, et al. (1998). Cell 93(3): 385-95.
Park et al., Analytical Biochemistry 1999, 269, 94-104.
Patani, G.A. et al. Chem. Rev. 1996, 96, 3147-3176.
Pernis, A. B. and P. B. Rothman (2002). "JAK-STAT signaling in asthma." J Clin Invest 109(10): 1279-83.
Peters et al., "Functional Significance of Tie2 Signaling in the Adult Vasculature." *The Endocrine Society*, pp. 51-71, 2004.
Remington's Pharmaceutical Sciences, 17th ed., Mack Publishing Company, Easton, Pa., 1985, p. 1418.
Report of STN database search run on Nov. 2, 2006 in files: Registry and Caplus; 79 pages.
Report of STN database search run on Nov. 9, 2006 in Registry file; 14 pages.
Report of STN database search run on Sep. 7, 2006 in files: Registry, Hcaplus, Marpat, Wpindex, Derwent Chemistry Resource, and Merged Markush Service; 79 pages.
Robinson, Eur. J. Surg. (1998).
Rodig, S. J., M. A. Meraz, et al. (1998). "Disruption of the Jak1 gene demonstrates obligatory and nonredundant roles of the Jaks in cytokine-induced biologic responses." Cell 93(3): 373-383.
Rousvoal, G. et al. Transpl Int. Dec. 2006;19(12):1014-21.
Saemann, M. D., C. Diakos, et al. (2003). "Prevention of CD40-triggered dendritic cell maturation and induction of T-cell hyporeactivity by targeting of Janus kinase 3." *Am J Transplant*, 3(11): 1341-1349.
Samanta et al., "Janus Kinase 2: A critical target in chronic myelogenous leukemia", Cancer Res 66(13):6468-6472 (2006).
Scott, M. J., C. J. Godshall, et al. (2002). "Jaks, STATs, Cytokines, and Sepsis." Clin Diagn Lab *Immunol* 9(6): 1153-9.
Seto, Y., H. Nakajima, et al. (2003). "Enhanced Th2 cell-mediated allergic inflammation in Tyk2-deficient mice." *J Immunol* 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Singh et al., British Journal of Surgery (2001).
Sriram, K. et al. *J. Biol. Chem.* 2004, 279(19):19936-47. Epub Mar. 2, 2004.
Staerk, J., et al. *JBC* 280:41893-41899.
T. Higuchi and V. Stella, "Pro-drugs as Novel Delivery Systems," vol. 14 of the A.C.S. Symposium Series.
T.W. Green and P.G.M. Wuts, Protective Groups in Organic Synthesis, 3rd. Ed., Wiley & Sons, Inc., New York (1999).
Takemoto, S., J. C. Mulloy, et al. (1997). "Proliferation of adult T cell leukemia/lymphoma cells is associated with the constitutive activation of JAK/STAT proteins." *Proc Natl Acad Sci U S A* 94(25): 13897-902.
Thompson, J.E., et al. Bioorganic & Medicinal Chemistry Letters 12 (2002) 1219-1223.
Wang et al., "Adaptive secretion of the Granulocyte Macrophage Colony Stimulating Factor (GM-CSF) mediates Imatinib- and Nilotinib-resistance in BCR/ABL-positive progenitors via JAK-2/STAT-5 pathway activation", Blood, 109(5): 2147-2155 (2007); pre-published online as a Blood First Edition Paper on Nov. 7, 2006.
Williams et al., "Arf gene loss enhances oncogenicity and limits imatinib response in mouse models of Bcr-Abl-induced acute lymphoblastic leukemia", PNAS 103(17):6688-6693 (2006).
Wu T.Y.H., et al. Organic Letters, 2003, 5(20), 3587-3590.
Zou, Xiaoming, and Calame, Kathryn, "Signaling Pathways Activated by Oncogenic Forms of Abl Tyrosine Kinase." *Journal of Biological Chemistry*, 274(26):18141-18144, 1999.

\* cited by examiner

SUBSTITUTED HETEROCYCLES AS JANUS KINASE INHIBITORS

CROSS REFERENCE TO RELATED APPLICATIONS

This application is a continuation of U.S. Ser. No. 11/961,424, filed on Dec. 20, 2007, which claims the benefit of U.S. Ser. No. 60/876,705, filed Dec. 22, 2006, and U.S. Ser. No. 60/928,205, filed May 8, 2007, the disclosures of each of which are incorporated herein by reference in their entireties.

FIELD OF THE INVENTION

The present invention provides substituted tricyclic heteroaryl compounds, including, for example, pyridinoindoles, pyrimidinoindoles and triazinoindoles that modulate the activity of kinases and are useful in the treatment of diseases related to activity of kinases including, for example, immune-related diseases, skin disorders, myeloid proliferative disorders, cancer, and other diseases.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

Protein kinases can be categorized as receptor type and non-receptor type and may show specificity for phosphorylating either a Ser/Thr residue or a Tyr residue. Thus, a kinase may be described as a receptor Ser/Thr kinase, a non-receptor Ser/Thr kinase, a receptor Tyr kinase, or a non-receptor Tyr kinase. Receptors that bind to ligands from the TGFβ family of growth factors are Ser/Thr kinases and are termed TGFβR. Examples of non-receptor Ser/Thr kinases include PKA, PKG, PKC, CaM-kinase, phosphorylase kinase, MAPK (ERK), MEKK, Akt, and mTOR.

Receptor Tyr kinases (RTKs) have an extracellular portion, a transmembrane domain, and an intracellular portion, while non-receptor tyrosine kinases are entirely intracellular. RTK mediated signal transduction is typically initiated by extracellular interaction with a specific growth factor (ligand), typically followed by receptor dimerization, stimulation of the intrinsic protein tyrosine kinase activity, and receptor transphosphorylation. Binding sites are thereby created for intracellular signal transduction molecules and lead to the formation of complexes with a spectrum of cytoplasmic signaling molecules that facilitate the appropriate cellular response such as cell division, differentiation, metabolic effects, and changes in the extracellular microenvironment.

At present, at least nineteen (19) distinct RTK subfamilies have been identified. One RTK subfamily, designated the HER subfamily, includes EGFR, HER2, HER3 and HER4. A second family of RTKs, designated the insulin subfamily, includes the INS-R, the IGF-1R and the IR-R. A third family, the "PDGF" subfamily, includes the PDGF alpha and beta receptors, CSFIR, c-kit and FLK-II. Another subfamily of RTKs, referred to as the FLK subfamily, encompasses the Kinase insert Domain-Receptor fetal liver kinase-1 (KDR/FLK-1), the fetal liver kinase 4 (FLK-4) and the fms-like tyrosine kinase 1 (flt-1). Two other subfamilies of RTKs have been designated as the FGF receptor family (FGFR1, FGFR2, FGFR3 and FGFR4) and the Met subfamily (c-Met, Ron and Sea). Additional RTKs are VEGFR/Flt2, FLT4, Eph family RTKs (A1, A2, A3, B2, B4), and Tie2. For a detailed discussion of protein kinases, see for example, Blume-Jensen, P. et al., Nature. 2001, 411(6835):355-365, and Manning, G. et al., Science. 2002, 298(5600):1912-1934. A review of TRK family kinases can be found in Cancer Letter 169 (2001) 107-114 which is herein incorporated by reference. A review of Eph family kinases can be found in Genes & Development, 17:1429-1450 and is herein incorporated by reference. Information on Tie2 kinase can be found in K. G. Peters et al. "Functional Significance of Tie2 Signaling in the Adult Vasculature", 2004, © The Endocrine Society.

The non-receptor Tyr kinases can be divided into numerous subfamilies, including Src, Btk, ABL, Fak, and JAK. Each of these subfamilies can be further subdivided into multiple members that have been frequently linked to oncogenesis. The ABL family includes ABL1 and ARG (ABL2). The JAK family includes JAK1, JAK2, JAK3, and TYK2. The Src family, is the largest and includes Src, Fyn, Lck and Fgr among others. For a detailed discussion of these kinases, see Bolen J B. Nonreceptor tyrosine protein kinases. Oncogene. 1993, 8(8):2025-31.

The inappropriate regulation of kinase activity can contribute to disease states. Deregulated kinase activity is known to occur through mutations (i.e. gene fusions resulting from chromosomal translocations, point mutations that effect kinase activity) or changes to expression of the kinase gene (i.e. increased expression through gene amplification). Over 40 chromosomal translocations, leading to gene fusions and the deregulation of 12 different Tyr kinases, are associated with various hematologic malignancies. The protein tyrosine kinases involved in hematologic malignancies include, ABL (ABL1), ARG (ABL2), PDGFβR, PDGFαR, JAK2, SYK, TRKC, FGFR1, FGFR3, FLT3, and FRK. The range of diseases associated with mutations in these kinases include myeloproliferative disorder, MPD; chronic myeloid leukemia, CML; acute myeloid leukemia, AML; acute lymphoblastic leukemia, ALL; chronic myelomonocytic leukemia, DMML; 8p13 myeloproliferative syndrome, EMS; anaplastic large cell lymphoma, ALCL; inflammatory myofibroblastic tumor, IMF; peripheral T-cell lymphoma, PTL; polycythemia vera, PV; and essential thrombocythemia, ET (Y. Chalandon and J. Schwaller, Haematologica, 2005; 90(7):949-968). Small molecule inhibitors of various kinases have been successfully employed to treat disease states. Small molecule inhibitors for the protein tyrosine kinases ABL, ALK, PDGFαR, PDGFβR, KIT, FLT3, FGFR1, and FGFR3 are used to treat hematologic malignancies (Y. Chalandon and J. Schwaller, Haematologica, 2005; 90(7):949-968).

Specifically, inappropriate activity of the ABL and JAK non-receptor Tyr kinases are implicated in human disease. Inappropriate ABL kinase activity is a hallmark of cancer and may contribute to myeloproliferative disorders and fibrotic conditions such as pulmonary fibrosis (Daniels C E et al., J Clin Invest, 2004 November; 114(9):1308-16). Inappropriate JAK kinase activity contributes to cancer, myeloid proliferative disorders and immune system disorders.

The ABL family of non-receptor Tyr kinases includes ABL1 and ARG (ABL2) (Kruh G D et al., PNAS, 1990 August; 87(15)5802-6). Henceforth, the ABL family will be referred to simply as ABL. Studies of ABL1 have demonstrated involvement in multiple signaling pathways, including Ras-dependent, Rac-dependent, JNK-dependent, PI3K-dependent, PKC-dependent, mTOR, and JAK/STAT. These signaling pathways regulate processes including cell cycle progression, cell cycle arrest, cell growth, cell differentiation and apoptosis (M G Kharas and D A Fruman, Cancer Research, 65:2047-2053; X. Zou and K. Calame, JBC, 274 (26):18141-18144).

Deregulation of ABL kinase activity are linked to disease and may occur through gene amplification and mutations. For example, Gene fusions of ABL kinases are linked to blood cancers. ABL1 fusions with TEL, NUP214, EMS, and SFQ have been correlated with CML and ALL and fusions of ARG (ABL2) with BCR and TEL have been correlated with CML (Y. Chalandon and J. Schwaller, Haematologica, 2005; 90(7): 949-968). The BCR/ABL1 fusion gene, which results from a chromosomal translocation generating the Philadelphia chromosome (Ph), is widely thought to be a causative factor in leukemia: the Philadelphia chromosome, is associated with 95% of CIVIL cases and 10% of ALL cases (X. Zou and K. Calame, JBC, 274(26):18141-18144).

The small molecule inhibitor Imatinib mesylate (Gleevec™), a small molecular inhibitor of ABL1 kinase activity, has been widely used to treat CIVIL. However, clinical resistance to Imatinib is increasingly problematic. Resistance occurs most commonly through clonal expansion of mutants in the kinase domain of BCR/ABL1 (Gone M E et al., Science, 293(5531):876-80). Numerous mutations have been mapped from clinical isolates, including T315D, F359D, D276G, E255K, M351T, G250E, H396R, Q252H, Y253H, E355G, F317L, G250E, Y253F, F359V, Q252R, L387M, M244V, M343T/F382L, and V379I (Shah N P et al., Cancer Cell, 2:117-25). Thus, alternative small molecule inhibitors are needed to target Imatinib resistant ABL1 mutants. In addition, combination therapy with multiple small molecule inhibitors targeting ABL1 are expected to reduce the likelihood of resistance arising in a single cell, through mutation of ABL1, and subsequent clonal expansion.

The pathway involving the Janus kinase family of protein tyrosine kinases (JAKs) and Signal Transducers and Activators of Transcription (STATs) is engaged in the signaling of a wide range of cytokines and growth factors. Cytokines are low-molecular weight polypeptides or glycoproteins that stimulate biological responses in virtually all cell types. For example, cytokines regulate many of the pathways involved in the host inflammatory response to sepsis. Cytokines influence cell differentiation, proliferation and activation, and they can modulate both proinflammatory and anti-inflammatory responses to allow the host to react appropriately to pathogens. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "JAKs, STATs, Cytokines, and Sepsis." *Clin Diagn Lab Immunol* 9(6): 1153-9).

The JAK family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra). While JAK1, JAK2 and TYK2 are ubiquitously expressed, JAK3 is reported to be preferentially expressed in lymphocytes.

Not only do the cytokine-stimulated immune and inflammatory responses contribute to normal host defense, they also play roles in the pathogenesis of diseases: pathologies such as severe combined immunodeficiency (SCID) arise from hypoactivity and suppression of the immune system, and a hyperactive or inappropriate immune/inflammatory response contributes to the pathology of autoimmune diseases such as rheumatoid and psoriatic arthritis, asthma and systemic lupus erythematosus, inflammatory bowel disease, multiple sclerosis, type I diabetes mellitus, myasthenia gravis, thyroiditis, immunoglobulin nephropathies, myocarditis as well as illnesses such as scleroderma and osteoarthritis (Ortmann, R. A., T. Cheng, et al. (2000). "Janus kinases and signal transducers and activators of transcription: their roles in cytokine signaling, development and immunoregulation." *Arthritis Res* 2(1): 16-32). Furthermore, syndromes with a mixed presentation of autoimmune and immunodeficiency disease are quite common (Candotti, F., L. Notarangelo, et al. (2002). "Molecular aspects of primary immunodeficiencies: lessons from cytokine and other signaling pathways." *J Clin Invest* 109(10): 1261-9). Thus, therapeutic agents are typically aimed at augmentation or suppression of the immune and inflammatory pathways, accordingly.

Deficiencies in expression of JAK family members are associated with disease states. JAK1-/- mice are runted at birth, fail to nurse, and die perinatally (Rodig, S. J., M. A. Meraz, et al. (1998). "Disruption of the JAK1 gene demonstrates obligatory and nonredundant roles of the JAKs in cytokine-induced biologic responses." *Cell* 93(3): 373-83). JAK2-/- mouse embryos are anemic and die around day 12.5 postcoitum due to the absence of definitive erythropoiesis. JAK2-deficient fibroblasts do not respond to IFN gamma, although responses to IFNalpha/beta and IL-6 are unaffected. JAK2 functions in signal transduction of a specific group of cytokine receptors required in definitive erythropoiesis (Neubauer, H., A. Cumano, et al. (1998). *Cell* 93(3): 397-409; Parganas, E., D. Wang, et al. (1998). *Cell* 93(3): 385-95.). JAK3 appears to play a role in normal development and function of B and T lymphocytes. Mutations of JAK3 are reported to be responsible for autosomal recessive severe combined immunodeficiency (SCID) in humans (Candotti, F., S. A. Oakes, et al. (1997). "Structural and functional basis for JAK3-deficient severe combined immunodeficiency." *Blood* 90(10): 3996-4003).

The JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. For instance, the inappropriate immune responses that characterize asthma are orchestrated by a subset of CD4+ T helper cells termed T helper 2 (Th2) cells. Signaling through the cytokine receptor IL-4 stimulates JAK1 and JAK3 to activate STAT6, and signaling through IL-12 stimulates activation of JAK2 and TYK2, and subsequent phosphorylation of STAT4. STAT4 and STAT6 control multiple aspects of CD4+ T helper cell differentiation (Pernis, A. B. and P. B. Rothman (2002). "JAK-STAT signaling in asthma." J Clin Invest 109(10): 1279-83). Furthermore, TYK2-deficient mice were found to have enhanced Th2 cell-mediated allergic airway inflammation (Seto, Y., H. Nakajima, et al. (2003). "Enhanced Th2 cell-mediated allergic inflammation in Tyk2-deficient mice." J Immunol 170(2): 1077-83). Moreover, multiple cytokines that signal through JAK kinases have been linked to inflammatory diseases or conditions of the upper respiratory tract such as those affecting the nose and sinuses (e.g. rhinitis, sinusitis) whether classically allergic reactions or not.

The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

The JAK/STAT pathway has also been implicated in cancers. Activation of STAT3 has been reported for endometrial and cervical cancers (C. L. Chen et al. (2007). British Journal of Cancer 96: 591-599). In addition, JAK/STAT pathway components, in particular JAK3, play a role in cancers of the immune system. In adult T cell leukemia/lymphoma (ATLL), human CD4+ T cells acquire a transformed phenotype, an event that correlates with acquisition of constitutive phosphorylation of JAKs and STATs. Furthermore, an association between JAK3 and STAT-1, STAT-3, and STAT-5 activation and cell-cycle progression was demonstrated by both propidium iodide staining and bromodeoxyuridine incorporation in cells of four ATLL patients tested. These results imply that JAK/STAT activation is associated with replication of leukemic cells and that therapeutic approaches aimed at JAK/STAT inhibition may be considered to halt neoplastic growth (Takemoto, S., J. C. Mulloy, et al. (1997). "Proliferation of adult T cell leukemia/lymphoma cells is associated with the constitutive activation of JAK/STAT proteins." *Proc Natl Acad Sci USA* 94(25): 13897-902).

Blocking signal transduction at the level of the JAK kinases holds promise for developing treatments for human cancers. Cytokines of the interleukin 6 (IL-6) family, which activate the signal transducer gp130, are major survival and growth factors for human multiple myeloma (MM) cells. The signal transduction of gp130 is believed to involve JAK1, JAK2 and Tyk2 and the downstream effectors STAT3 and the mitogen-activated protein kinase (MAPK) pathways. In IL-6-dependent MM cell lines treated with the JAK2 inhibitor tyrphostin AG490, JAK2 kinase activity and ERK2 and STAT3 phosphorylation were inhibited. Furthermore, cell proliferation was suppressed and apoptosis was induced (De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." *Br J Haematol* 109(4): 823-8). However, in some cases, AG490 can induce dormancy of tumor cells and actually then protect them from death.

Activation of JAK/STAT in cancers may occur by multiple mechanisms including cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Importantly, activation of STAT signaling, as well as other pathways downstream of JAKs (e.g. Akt), has been correlated with poor prognosis in many cancer types (Bowman, T., et al. *Oncogene* 19:2474-2488, 2000). Moreover, elevated levels of circulating cytokines that signal through JAK/STAT may adversely impact patient health as they are thought to play a causal role in cachexia and/or chronic fatigue. As such, JAK inhibition may be therapeutic for the treatment of cancer patients for reasons that extend beyond potential anti-tumor activity. The cachexia indication may gain further mechanistic support with realization that the satiety factor leptin signals through JAKs.

Pharmacological targeting of Janus kinase 3 (JAK3) has been employed successfully to control allograft rejection and graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann, M. D., C. Diakos, et al. (2003). "Prevention of CD40-triggered dendritic cell maturation and induction of T-cell hyporeactivity by targeting of Janus kinase 3." *Am J Transplant* 3(11): 1341-9). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type 1 diabetes (Cetkovic-Cvrlje, M., A. L. Dragt, et al. (2003). "Targeting JAK3 with JANEX-1 for prevention of autoimmune type 1 diabetes in NOD mice." *Clin Immunol* 106(3): 213-25).

It has been suggested that inhibition of JAK2 tyrosine kinase can be beneficial for patients with myeloproliferative disorder. (Levine, et al., *Cancer Cell, vol.* 7, 2005: 387-397) Myeloproliferative disorder (MPD) includes polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES) and systemic mast cell disease (SMCD). Although the myeloproliferative disorder (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possess a recurrent somatic activating mutation in the JAK2 tyrosine kinase. It has also been reported that inhibition of the JAK2V617F kinase with a small molecule inhibitor leads to inhibition of proliferation of hematopoietic cells, suggesting that the JAK2 tyrosine kinase is a potential target for pharmacologic inhibition in patients with PV, ET and MMM.

Inhibition of the JAK kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, *Nat Rev Drug Disc.*, 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins -2, -4, -6, -7, -12, -15, -18, and -23 as well as GM-CSF and IFNg, signal through the Janus (JAK) kinases (*Adv Pharmacol.* 2000; 47:113-74). As such, blocking signal transduction at the level of JAK kinases may result in therapeutic benefits in patients suffering from psoriasis or other immune disorders of the skin.

It has been known that certain therapeutics can cause immune reactions such as skin rash or diarrhea in some patients. For instance, administration of some of the new targeted anti-cancer agents such as Iressa, Erbitux, and Tarceva has induced acneiform rash with some patients. Another example is that some therapeutics used topically induce skin irritation, skin rash, contact dermatitis or allergic contact sensitization. For some patients, these immune reactions may be bothersome, but for others, the immune reactions such as rash or diarrhea may result in inability to continue the treatment. Although the driving force behind these immune reactions has not been elucidated completely at the present time, these immune reactions are likely linked to immune infiltrate.

Inhibitors of Janus kinases or related kinases are widely sought and several publications report effective classes of compounds. For example, certain inhibitors are reported in WO 99/65909, US 2004/0198737; WO 2004/099204; WO 2004/099205; and WO 01/42246. Heteroaryl substituted pyrroles and other compounds are reported in WO 2004/72063 and WO 99/62908.

Thus, new or improved agents which inhibit kinases are continually needed, in part, to cope with resistant mutants. Combination therapy (using newly identified agents), may decrease the odds of developing drug resistant kinase mutants and new agents are needed to treat existing drug-resistant kinase mutants (i.e. ABL1 mutants which are resistant to Imatinib). Agents that inhibit JAK kinases are continually needed, that act as immunosuppressive agents for organ transplants, as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease), diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics, to name a few. The compounds, compositions and methods described herein are directed toward these needs and other ends.

SUMMARY OF THE INVENTION

The present invention provides compounds of Formula I:

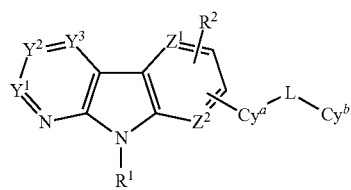

or pharmaceutically acceptable salt forms or prodrugs thereof, wherein constituent members are defined herein.

The present invention further provides compositions comprising a compound of Formula I, or pharmaceutically acceptable salt thereof, and at least one pharmaceutically acceptable carrier.

The present invention further provides methods of modulating an activity of JAK comprising contacting JAK with a compound of Formula I, or pharmaceutically acceptable salt thereof.

The present invention further provides methods of treating a disease in a patient, wherein the disease is associated with JAK activity, comprising administering to the patient a therapeutically effective amount of a compound of Formula I, or pharmaceutically acceptable salt thereof.

DETAILED DESCRIPTION

The present invention provides, inter alia, compounds that modulate the activity of one or more JAKs and are useful, for example, in the treatment of various diseases such as those associated with JAK expression or activity. The compounds of the invention have Formula I:

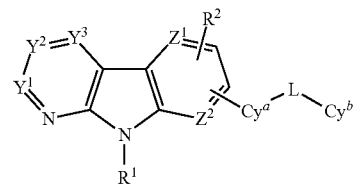

including pharmaceutically acceptable salt forms or prodrugs thereof, wherein:

$Cy^a$ is selected from arylene, heteroarylene, cycloalkylene, and heterocycloalkylene, each optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}NR^{c1}S(O)_2R^{b1}S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$;

$Cy^b$ is selected from aryl, heteroaryl, cycloalkyl, and heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O) R^{b2}NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)$ OR$^{a2}$, OC(O)R$^{b2}$, OC(O)NR$^{c2}$R$^{d2}$, C(=NR$^i$)NR$^{c2}$R$^{d2}$, NR$^{c2}$C(NR$^i$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$C(O)NR$^{c2}$R$^{d2}$, NR$^{c2}$S(O)R$^{b2}$, NR$^{c2}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$;

L is a divalent moiety selected from C$_{1-6}$ alkylene, C$_{2-6}$ alkenylene, C$_{2-6}$ alkynylene, (C$_{1-6}$ alkylene)$_p$-(C$_{3-10}$ cycloalkylene)-(C$_{1-6}$ alkylene)$_q$, (C$_{1-6}$ alkylene)$_p$-(C$_{3-10}$ heterocycloalkylene)-(C$_{1-6}$ alkylene)$_q$, (C$_{1-6}$ alkylene)$_p$-(C$_{6-10}$ arylene)-(C$_{1-6}$ alkylene)$_q$, (C$_{1-6}$ alkylene)$_p$-(C$_{3-10}$ heteroarylene)-(C$_{1-6}$ alkylene)$_q$, (C$_{1-6}$ alkylene)$_p$-O—(C$_{1-6}$ alkylene)$_q$, (C$_{1-6}$ alkylene)$_p$-S—(C$_{1-6}$ alkylene)$_q$, (C$_{1-6}$ alkylene)$_p$-NR$^{c3}$—(C$_{1-6}$ alkylene)$_q$, (C$_{1-6}$ alkylene)$_p$-C(O)—(C$_{1-6}$ alkylene)$_q$, (C$_{1-6}$ alkylene)$_p$-OC(O)—(C$_{1-6}$ alkylene)$_q$, (C$_{1-6}$ alkylene)$_p$-C(O)NR$^{c3}$—(C$_{1-6}$ alkylene)$_q$, (C$_{1-6}$ alkylene)$_p$-OC(O)NR$^{c3}$—(C$_{1-6}$ alkylene)$_q$, (C$_{1-6}$ alkylene)$_p$-SO—(C$_{1-6}$ alkylene)$_q$, (C$_{1-6}$ alkylene)$_p$-SO$_2$—(C$_{1-6}$ alkylene)$_q$, (C$_{1-6}$ alkylene)$_p$-SONR$^{c3}$—(C$_{1-6}$ alkylene)$_q$, (C$_{1-6}$ alkylene)$_p$-SO$_2$NR$^{c3}$—(C$_{1-6}$ alkylene)$_q$, (C$_{1-6}$ alkylene)$_p$-NR$^{c3}$CONR$^{d3}$—(C$_{1-6}$ alkylene)$_q$, (C$_{1-6}$ alkylene)$_p$-NR$^{c3}$SONR$^{d3}$—(C$_{1-6}$ alkylene)$_q$, and (C$_{1-6}$ alkylene)$_p$-NR$^{c3}$SO$_2$NR$^{d3}$—(C$_{1-6}$ alkylene)$_q$, wherein each of the C$_{1-6}$ alkylene, C$_{2-6}$ alkenylene, C$_{2-6}$ alkynylene, cycloalkylene, arylene, heterocycloalkylene, and heteroarylene is optionally substituted by 1, 2 or 3 substituents independently selected from C$_{1-4}$ alkyl, C$_{2-4}$ alkenyl, C$_{2-4}$ alkynyl, C$_{1-4}$ hydroxyalkyl, C$_{1-4}$ cyanoalkyl, aryl, heteroaryl, cycloalkyl, heterocycloalkyl, halo, CN, NO$_2$, SCN, OH, C$_{1-4}$ haloalkyl, halosulfanyl, C$_{1-4}$ alkoxy-C$_{1-4}$ alkyl, C$_{1-4}$ alkoxy, C$_{1-4}$ haloalkoxy, amino, C$_{1-4}$ alkylamino, and C$_{2-8}$ dialkylamino;

wherein L is oriented in either direction with respect to its attachment to Cy$^a$ and Cy$^b$;

Y$^1$ is selected from CR$^3$ and N;
Y$^2$ is selected from CR$^4$ and N;
Y$^3$ is selected from CR$^5$ and N;
provided that at least one of Y$^1$ and Y$^2$ is other than N;
Z$^1$ is selected from CR$^6$ and N;
Z$^2$ is selected from CR$^7$ and N;
R$^1$ is selected from H, C$_{1-6}$ alkyl, C(O)C$_{1-6}$ alkyl, and C(O) aryl;

R$^2$, R$^3$, R$^4$, R$^5$, R$^6$, and R$^7$ are independently selected from H, halo, C$_{1-6}$ alkyl, C$_{2-6}$ alkenyl, C$_{2-6}$ alkynyl, Cy$^1$, C$_{1-6}$ haloalkyl, halosulfanyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^i$)NR$^{c4}$R$^{d4}$, NR$^{c4}$C(=NR$^i$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{2-6}$ alkenyl, or C$_{2-6}$ alkynyl is optionally substituted with 1, 2, 3, 4, or 5 substituents selected from CN, NO$_2$, Cy$^1$, Cy$^1$-(C$_{1-6}$ alkyl)-, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, C(=NR$^i$)NR$^{c4}$R$^{d4}$, NR$^{c4}$C(=NR$^i$)NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

Cy, Cy$^1$, and Cy$^2$ are independently selected from aryl, heteroaryl, cycloalkyl, and heterocycloalkyl, each optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, N$_3$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^i$)NR$^{c5}$R$^{d5}$, NR$^{c5}$C(=NR$^i$)NR$^{c5}$R$^{d5}$, P(R$^{f5}$)$_2$, P(OR$^{e5}$)$_2$, P(O)R$^{e5}$R$^{f5}$, P(O)OR$^{e5}$OR$^{f5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$, wherein said C$_{1-6}$ alkyl, C$_{2-6}$ alkenyl, and C$_{2-6}$ alkynyl are each optionally substituted by 1, 2, or 3 substituents independently selected from halo, C$_{1-6}$ haloalkyl, halosulfanyl, CN, NO$_2$, N$_3$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, (=NR$^i$)NR$^{c5}$R$^{d5}$, NR$^{c5}$C(=NR$^i$)NR$^{c5}$R$^{d5}$, P(R$^{f5}$)$_2$, P(OR$^{e5}$)$_2$, P(O)R$^{e5}$R$^{f5}$, P(O)OR$^{e5}$OR$^{f5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{a1}$, R$^{a2}$, and R$^{a4}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, and C(O)—C$_{1-7}$ hydrocarbyl, wherein said C$_{1-6}$ alkyl, C$_{2-6}$ alkenyl, C$_{1-7}$ hydrocarbyl, or C$_{2-6}$ alkynyl is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{b1}$, R$^{b2}$, and R$^{b4}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, wherein said C$_{1-6}$ alkyl, C$_{2-6}$ alkenyl, or C$_{2-6}$ alkynyl is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{c1}$, R$^{c2}$, and R$^{c4}$ are independently selected from H, Cy$^2$, —(C$_{1-6}$ alkyl)-Cy$^2$, C$_{1-6}$ alkyl, C$_{1-6}$ haloalkyl, C$_{1-6}$ hydroxyalkyl, C$_{2-6}$ alkenyl, C$_{2-6}$ alkynyl, wherein said C$_{1-6}$ alkyl, C$_{2-6}$ alkenyl, or C$_{2-6}$ alkynyl, is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{d1}$, R$^{d2}$, and R$^{d4}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, wherein said C$_{1-6}$ alkyl, C$_{2-6}$ alkenyl, or C$_{2-6}$ alkynyl, is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl; or, one or more of R$^{c1}$ and R$^{d1}$, R$^{c2}$ and R$^{d2}$, and R$^{c4}$ and R$^{d4}$ together with the N atom to which they are attached, optionally form a 4-, 5-, 6- or 7-membered heterocycloalkyl group or heteroaryl group, each optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{c3}$ and R$^{d3}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, wherein said C$_{1-6}$ alkyl, C$_{2-6}$ alkenyl, or C$_{2-6}$ alkynyl is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{a5}$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

R$^{b5}$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; or $R^{c5}$ and $R^{d5}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{e5}$ is H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

$R^{f5}$ is H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl;

$R^i$ is H, CN, $NO_2$, $C(O)NH_2$, or $C_{1-6}$ alkyl;

p is 0 or 1; and q is 0 or 1.

In some embodiments, when $Cy^a$ is a piperazine ring, $R^2$ is other than halo.

In some embodiments, $Y^1$ is N and $Y^2$ is $CR^4$.
In some embodiments, $Y^2$ is N and $Y^1$ is $CR^3$.
In some embodiments, $Y^2$ is N.
In some embodiments, $Y^3$ is N.
In some embodiments, $Y^3$ is $CR^5$.
In some embodiments, at least one of $Y^1$, $Y^2$ and $Y^3$ is N.
In some embodiments, both of $Y^1$ and $Y^3$ are N.
In some embodiments, both of $Y^2$ and $Y^3$ are N.
In some embodiments, $Y^1$ is $CR^3$, $Y^2$ is $CR^4$, and $Y^3$ is $CR^5$.
In some embodiments, $Z^1$ is N.
In some embodiments, $Z^1$ is $CR^6$.
In some embodiments, $Z^2$ is N.
In some embodiments, $Z^2$ is $CR^7$.
In some embodiments, at least one of $Z^1$ and $Z^2$ is N.
In some embodiments, both of $Z^1$ and $Z^2$ are N.
In some embodiments, $Z^1$ is $CR^6$ and $Z^2$ is $CR^7$.

In some embodiments, $Cy^a$ is aryl or heteroaryl, each optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$.

In some embodiments, $Cy^a$ is aryl optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR$ $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$.

In some embodiments, $Cy^a$ is aryl optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$.

In some embodiments, $Cy^a$ is aryl optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, CN, $NO_2$, $OR^{a1}$, $SR^{a1}$, and $NR^{c1}R^{d1}$.

In some embodiments, $Cy^a$ is aryl optionally substituted by 1, 2, 3, 4 or 5 substituents independently selected from halo, $C_{1-6}$ alkyl, $C_{2-6}$ and $OR^{a1}$.

In some embodiments, $Cy^a$ is phenyl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{a1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$.

In some embodiments, $Cy^a$ is heteroaryl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^1$, $S(O)R^{b1}$, $S(O)NR^{c1}R^{d1}$, $S(O)_2R^{b1}$, and $S(O)_2NR^{c1}R^{d1}$.

In some embodiments, $Cy^a$ is cycloalkyl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$.

In some embodiments, $Cy^a$ is heterocycloalkyl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$.

In some embodiments, $Cy^a$ is a substituted aryl or substituted heteroaryl ring according to Formula IA:

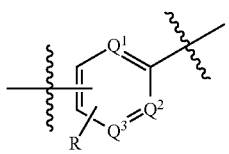

IA wherein:

R is selected from H, halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl, $C_{2-6}$ alkenyl, and $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; and the point of attachment on the right hand side of the ring of Formula IA is attached to L.

In some embodiments, $Cy^a$ is a substituted aryl or substituted heteroaryl ring according to Formula IB:

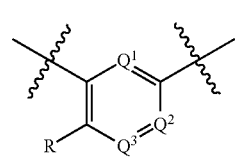

IB wherein:

R is selected from H, halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$;

$Q^1$, $Q^2$ and $Q^3$ are independently selected from $CR^Q$ and N;

$R^Q$ is independently selected from H, halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^i)NR^{c1}R^{d1}$, $NR^{c1}C(=NR^i)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $S(O)R^{b1}$, $S(O)NR^{c1}R^{d1}$, $S(O)_2R^{b1}$, and $S(O)_2NR^{c1}R^{d1}$; and the point of attachment on the right hand side of the ring of Formula IB is attached to L.

In some embodiments, R is selected from H, $C_{1-6}$ alkyl, halo and $OR^{a1}$.

In some embodiments, R is selected from $C_{1-6}$ alkyl, halo and $OR^{a1}$.

In some embodiments, R is selected from $C_{1-6}$ alkyl and $OR^{a1}$.

In some embodiments, R is selected from $C_{1-6}$ alkyl and halo.

In some embodiments, $Q^1$ is N.
In some embodiments, $Q^1$ is $CR^Q$.
In some embodiments, $Q^2$ is N.
In some embodiments, $Q^2$ is $CR^Q$.
In some embodiments, $Q^3$ is N.
In some embodiments, $Q^3$ is $CR^Q$.
In some embodiments, at least one of $Q^1$, $Q^2$ and $Q^3$ is N.
In some embodiments, at least two of $Q^1$, $Q^2$ and $Q^3$ is N.
In some embodiments, all of $Q^1$, $Q^2$ and $Q^3$ are N.
In some embodiments, all of $Q^1$, $Q^2$ and $Q^3$ are $CR^Q$.

In some embodiments, $R^Q$ is independently selected from H, halo, $C_{1-6}$ alkyl, $C_{1-6}$ haloalkyl, halosulfanyl, Cy, $NR^{c1}R^{d1}$, $C(O)R^{b1}$, and $C(O)NR^{c1}R^{d1}$.

In some embodiments, $Cy^a$ is a substituted aryl or substituted heteroaryl ring according to Formula IC:

and the point of attachment on the right hand side of the ring of Formula IC is attached to L.

In some embodiments, $Cy^a$ is a substituted aryl or substituted heteroaryl ring according to Formula ID:

and the point of attachment on the right hand side of the ring of Formula ID is attached to L.

In some embodiments, $Cy^b$ is aryl or heteroaryl, each optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$.

In some embodiments, $Cy^b$ is aryl or heteroaryl, each optionally substituted by 1, 2, 3, 4 or 5 substituents independently selected from halo, $C_{1-6}$ alkyl, Cy, $C_{1-6}$ haloalkyl, halosulfanyl, CN, $NO_2$, $OR^{a2}$, and $NR^{c2}R^{d2}$.

In some embodiments, $Cy^b$ is aryl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, or $S(O)_2NR^{c2}R^{d2}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$.

In some embodiments, $Cy^b$ is phenyl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^aC(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^aS(O)R^{b2}$, $NR^{c2}S(O)_2R^{b2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$.

In some embodiments, $Cy^b$ is heteroaryl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$.

In some embodiments, $Cy^b$ is cycloalkyl, optionally substituted by 1, 2, 3, 4 or 5 substituents independently selected from halo, $C_{1-6}$ alkyl, $C_{2-6}$ alkenyl, $C_{2-6}$ alkynyl, Cy, $C_{1-6}$ haloalkyl, halosulfanyl, CN, NO$_2$, OR$^2$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$)NR$^{c2}$R$^{d2}$, NR$^{c2}$C(=NR$^i$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, or C$_{2-6}$ alkynyl is optionally substituted with 1, 2, 3, 4, or 5 substituents selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$)NR$^{c2}$R$^{d2}$, NR$^{c2}$C(=NR$^i$)NR$^{c2}$R$^{d2}$, NR$^{c2}$R$^{d2}$, NR$^{c2}$C(O)OR$^{b2}$, NR$^{c2}$C(O)NR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$C(O)NR$^{c2}$R$^{d2}$, NR$^{c2}$S(O)R$^{b2}$, NR$^{c2}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, Cy$^b$ is heterocycloalkyl, optionally substituted by 1, 2, 3, 4 or 5 substituents independently selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^2$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$)NR$^{c2}$R$^{d2}$, NR$^{c2}$C(=NR$^i$)NR$^{c2}$R$^{d2}$, NR$^{c2}$R$^{d2}$, NR$^{a}$C(O)R$^{b2}$, NR$^{c2}$C(O)OR$^{a2}$ NR$^{a}$C(O)NR$^{c2}$R$^{d2}$, NR$^{c2}$S(O)R$^{b2}$, NR$^{a}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, or C$_{2-6}$ alkynyl is optionally substituted with 1, 2, 3, 4, or 5 substituents selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$)NR$^{c2}$R$^{d2}$, NR$^{c2}$C(=NR$^i$) NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$C(O)NR$^{c2}$R$^{d2}$, NR$^{c2}$S(O)R$^{b2}$, NR$^{c2}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, Cy$^b$ is a substituted aryl or substituted heteroaryl ring according to Formula IE:

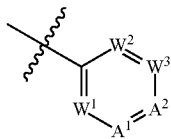

IE wherein:

W$^1$, W$^2$ and W$^3$ are independently selected from CR$^W$ and N;

A$^1$ and A$^2$ are independently selected from CR$^W$ and N; or the group, A$^1$=A$^2$, is S, O, or NH; and each R$^W$ is independently selected from H, halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$) NR$^{c2}$R$^{d2}$, NR$^{c2}$C(=NR$^i$)NR$^{c2}$R$^{d2}$, NR$^{c2}$R$^{d2}$, NR$^{c2}$C (O)R$^{b2}$, NR$^{c2}$C(O)OR$^{a2}$, NR$^{c2}$C(O)NR$^{c2}$R$^{d2}$, NR$^{c2}$S (O)R$^{b2}$, NR$^{c2}$S(O)$_2$R$^{b2}$, S(O)R$^{b2}$, S(O)NR$^{c2}$R$^{d2}$, S(O)$_2$ R$^{b2}$, and S(O)$_2$NR$^{c2}$R$^{d2}$; wherein said C$_{1-6}$ alkyl, C$_{2-6}$ alkenyl, or C$_{2-6}$ alkynyl is optionally substituted with 1, 2, 3, 4, or 5 substituents selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$) NR$^{c2}$R$^{d2}$, NR$^{c2}$C(=NR$^i$)NR$^{c2}$R$^{d2}$, NR$^{c2}$R$^{d2}$, NR$^{c2}$C (O)R$^{b2}$, NR$^{c2}$C(O)OR$^{a2}$ NR$^{c2}$C(O)NR$^{c2}$R$^{d2}$, NR$^{c2}$S(O) R$^{b2}$, NR$^{c2}$S(O)$_2$R$^{b2}$, NR$^{c2}$C(O)NR$^{c2}$R$^{d2}$, NR$^{c2}$S(O) R$^{b2}$, NR$^{c2}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$;

provided that, when A$^1$ and A$^2$ are independently selected from CR$^W$ and N; then at least three of W$^1$, W$^2$, W$^3$, A$^1$ and A$^2$ are CR$^W$.

In some embodiments, Cy$^b$ is a substituted aryl or substituted heteroaryl ring according to Formula IF:

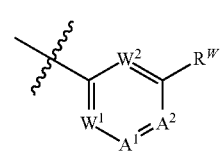

IF wherein:

W$^1$ and W$^2$ are independently selected from CR$^W$ and N;

A$^1$ and A$^2$ are independently selected from CR$^W$ and N; or the group, A$^1$=A$^2$, is S, O, or NH; and each R$^W$ is independently selected from H, halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$)NR$^{c2}$R$^{d2}$, NR$^{c2}$C (=NR$^i$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$R$^{b2}$, S(O) R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, or C$_{2-6}$ alkynyl is optionally substituted with 1, 2, 3, 4, or 5 substituents selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$) NR$^{c2}$R$^{d2}$, NR$^{c2}$C(=NR$^i$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S (O)$_2$R$^{b2}$, NR$^{c2}$C(O)NR$^{c2}$R$^{d2}$, NR$^{c2}$S(O)R$^{b2}$, NR$^{c2}$S(O)$_2$R$^{b2}$, S(O)R$^{b2}$, S(O)NR$^{c2}$R$^{d2}$, S(O)$_2$R$^{b2}$, or S(O)$_2$NR$^{c2}$R$^{d2}$.

In some embodiments, Q$^1$ is CR$^Q$.

In some embodiments, W$^1$ is N.

In some embodiments, W$^1$ is CR$^W$.

In some embodiments, W$^2$ is N.

In some embodiments, W$^2$ is CR$^W$.

In some embodiments, at least one of W$^1$ and W$^2$ is N.

In some embodiments, both of W$^1$ and W$^2$ are N.

In some embodiments, both of W$^1$ and W$^2$ are CR$^W$.

In some embodiments, A$^1$ is N.

In some embodiments, A$^1$ is CR$^W$.

In some embodiments, A$^2$ is N.

In some embodiments, A$^2$ is CR$^W$.

In some embodiments, at least one of W$^1$ and W$^2$ is N.

In some embodiments, both of W$^1$ and W$^2$ are N.

In some embodiments, both of W$^1$ and W$^2$ are CR$^W$.

In some embodiments, the group A$^1$=A$^2$ is S.

In some embodiments, the group A$^1$=A$^2$ is O.

In some embodiments, the group A$^1$=A$^2$ is NH.

In some embodiments, R$^W$ is independently selected from H, halo, C$_{1-6}$ alkyl, C$_{1-6}$ haloalkyl, OR$^{a1}$, halosulfanyl, Cy, NR$^{c1}$R$^{d1}$, C(O)R$^{b1}$, x and C(O)NR$^{c1}$R$^{d1}$.

In some embodiments, Cy$^b$ is a substituted aryl or substituted heteroaryl ring according to Formula IG:

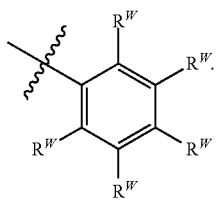

In some embodiments, L is a divalent moiety selected from C$_{1-6}$ alkylene, (C$_{1-6}$ alkylene)$_p$-O—(C$_{1-6}$ alkylene)$_q$, (C$_{1-6}$ alkylene)$_p$-S—(C$_{1-6}$ alkylene)$_q$, (C$_{1-6}$ alkylene)$_p$-NR$^6$—(C$_{1-6}$ alkylene)$_q$, (C$_{1-6}$ alkylene)$_p$-C(O)—(C$_{1-6}$ alkylene)$_q$, (C$_{1-6}$ alkylene)$_p$-OC(O)—(C$_{1-6}$ alkylene)$_q$, (C$_{1-6}$ alkylene)$_p$-C(O)NR$^{c3}$—(C$_{1-6}$ alkylene)$_q$, (C$_{1-6}$ alkylene)$_p$-OC(O)NR$^{e3}$—(C$_{1-6}$ alkylene)$_q$, (C$_{1-6}$ alkylene)$_p$-SO—(C$_{1-6}$ alkylene)$_q$, (C$_{1-6}$ alkylene)$_p$-SO$_2$—(C$_{1-6}$ alkylene)$_q$, (C$_{1-6}$ alkylene)$_p$-SONR$^6$—(C$_{1-6}$ alkylene)$_q$, (C$_{1-6}$ alkylene)$_p$-SO$_2$NR$^{c3}$—(C$_{1-6}$ alkylene)$_q$, (C$_{1-6}$ alkylene)$_p$-NR$^6$CONR$^{d3}$—(C$_{1-6}$ alkylene)$_q$, (C$_{1-6}$ alkylene)$_p$-NR$^{e3}$SONR$^{d3}$—(C$_{1-6}$ alkylene)$_q$, and (C$_{1-6}$ alkylene)$_p$-NR$^6$SO$_2$NR$^{d3}$—(C$_{1-6}$ alkylene)$_q$, wherein the C$_{1-6}$ alkylene is optionally substituted by 1, 2 or 3 substituents independently selected from C$_{1-4}$ alkyl, C$_{2-4}$ alkenyl, C$_{2-4}$ alkynyl, C$_{1-4}$ hydroxyalkyl, C$_{1-4}$ cyanoalkyl, aryl, heteroaryl, cycloalkyl, heterocycloalkyl, halo, CN, NO$_2$, SCN, OH, C$_{1-4}$ haloalkyl, halosulfanyl, C$_{1-4}$ alkoxy-C$_{1-4}$ alkyl, C$_{1-4}$ alkoxy, C$_{1-4}$ haloalkoxy, amino, C$_{1-4}$ alkylamino, and C$_{2-8}$ dialkylamino.

In some embodiments, L is a divalent moiety selected from (C$_{1-6}$ alkylene)$_p$-C(O)NR$^{e3}$—(C$_{1-6}$ alkylene)$_q$ and (C$_{1-6}$ alkylene)$_p$-NR$^{c3}$CONR$^{d3}$—(C$_{1-6}$ alkylene)$_q$, wherein the C$_{1-6}$ alkylene is optionally substituted by 1, 2 or 3 substituents independently selected from C$_{1-4}$ alkyl, C$_{2-4}$ alkenyl, C$_{2-4}$ alkynyl, C$_{1-4}$ hydroxyalkyl, C$_{1-4}$ cyanoalkyl, aryl, heteroaryl, cycloalkyl, heterocycloalkyl, halo, CN, NO$_2$, SCN, OH, C$_{1-4}$ haloalkyl, halosulfanyl, C$_{1-4}$ alkoxy-C$_{1-4}$ alkyl, C$_{1-4}$ alkoxy, C$_{1-4}$ haloalkoxy, amino, C$_{1-4}$ alkylamino, and C$_{2-8}$ dialkylamino.

In some embodiments, L is a divalent moiety selected from (C$_{1-6}$ alkylene)$_p$-C(O)NR$^{c3}$—(C$_{1-6}$ alkylene)$_q$ and (C$_{1-6}$ alkylene)$_p$-NR$^{c3}$CONR$^{d3}$—(C$_{1-6}$ alkylene)$_q$.

In some embodiments, L is a divalent moiety selected from C(O)NH, C(O)NH—(C$_{1-6}$ alkylene) and NHCONH.

In some embodiments, L is C(O)NH.
In some embodiments, L is C(O)NH—(C$_{1-6}$ alkylene).
In some embodiments, L is NHCONH.
In some embodiments, L is C$_{1-6}$ alkylene.
In some embodiments, L is (C$_{1-6}$ alkylene)$_p$-(C$_{3-10}$ cycloalkylene)-(C$_{1-6}$ alkylene)$_q$.
In some embodiments, L is (C$_{1-6}$ alkylene)$_p$-(C$_{3-10}$ heterocycloalkylene)-(C$_{1-6}$ alkylene)$_q$.
In some embodiments, L is (C$_{1-6}$ alkylene)$_p$-(C$_{6-10}$arylene)-(C$_{1-6}$ alkylene)$_q$.
In some embodiments, L is (C$_{1-6}$ alkylene)$_p$-(C$_{3-10}$ heteroarylene)-(C$_{1-6}$ alkylene)$_q$.
In some embodiments, L is (C$_{1-6}$ alkylene)$_p$-O—(C$_{1-6}$ alkylene)$_q$.
In some embodiments, L is (C$_{1-6}$ alkylene)$_p$-S—(C$_{1-6}$ alkylene)$_q$.
In some embodiments, L is (C$_{1-6}$ alkylene)$_p$-NR$^6$—(C$_{1-6}$ alkylene)$_q$.

In some embodiments, L is (C$_{1-6}$ alkylene)$_p$-C(O)—(C$_{1-6}$ alkylene)$_q$.
In some embodiments, L is (C$_{1-6}$ alkylene)$_p$-OC(O)—(C$_{1-6}$ alkylene)$_q$.
In some embodiments, L is (C$_{1-6}$ alkylene)$_p$-C(O)NR$^6$—(C$_{1-6}$ alkylene)$_q$.
In some embodiments, L is (C$_{1-6}$ alkylene)$_p$-OC(O)NR$^6$—(C$_{1-6}$ alkylene)$_q$.
In some embodiments, L is (C$_{1-6}$ alkylene)$_p$-SO—(C$_{1-6}$ alkylene)$_q$.
In some embodiments, L is (C$_{1-6}$ alkylene)$_p$-SO$_2$—(C$_{1-6}$ alkylene)$_q$.
In some embodiments, L is (C$_{1-6}$ alkylene)$_p$-SONR$^6$—(C$_{1-6}$ alkylene)$_q$.
In some embodiments, L is (C$_{1-6}$ alkylene)$_p$-SO$_2$NR$^6$—(C$_{1-6}$ alkylene)$_q$.
In some embodiments, L is (C$_{1-6}$ alkylene)$_p$-NR$^6$CONR$^{d3}$—(C$_{1-6}$ alkylene)$_q$.
In some embodiments, L is (C$_{1-6}$ alkylene)$_p$-NR$^6$SONR$^{c3}$—(C$_{1-6}$ alkylene)$_q$.
In some embodiments, L is (C$_{1-6}$ alkylene)$_p$-NR$^6$SO$_2$NR$^{d3}$—(C$_{1-6}$ alkylene)$_q$.

In some embodiments, each of the C$_{1-6}$ alkylene, cycloalkylene, arylene, heterocycloalkylene, and heteroarylene in the above embodiments of L is optionally substituted by 1, 2 or 3 substituents independently selected from C$_{1-4}$ alkyl, C$_{2-4}$ alkenyl, C$_{2-4}$ alkynyl, C$_{1-4}$ hydroxyalkyl, C$_{1-4}$ cyanoalkyl, aryl, heteroaryl, cycloalkyl, heterocycloalkyl, halo, CN, NO$_2$, SCN, OH, C$_{1-4}$ haloalkyl, halosulfanyl, C$_{1-4}$ alkoxy-C$_{1-4}$ alkyl, C$_{1-4}$ alkoxy, C$_{1-4}$ haloalkoxy, amino, C$_{1-4}$ alkylamino, and C$_{2-8}$ dialkylamino.

In some embodiments p is 0.
In some embodiments p is 1.
In some embodiments q is 0.
In some embodiments q is 1.
In some embodiments p and q are both 0.
In some embodiments p and q are both 1.
In some embodiments, L is 0.
In some embodiments, L is NR$^6$CONR$^{d3}$.
In some embodiments, L is NR$^6$SO$_2$NR$^{d3}$.
In some embodiments p is 0.
In some embodiments p is 1.
In some embodiments q is 0.
In some embodiments q is 1.
In some embodiments p and q are both 0.
In some embodiments p and q are both 1.
In some embodiments p and q, when added together, total 1.

In some embodiments, R$^1$ is selected from H, C$_{1-6}$ alkyl, or C(O)C$_{1-6}$ alkyl.
In some embodiments, R$^1$ is H.
In some embodiments, R$^1$ is C$_{1-6}$ alkyl.
In some embodiments, R$^1$ is C(O)C$_{1-6}$ alkyl.
In some embodiments, R$^2$, R$^3$, R$^4$, R$^5$, R$^6$, and R$^7$ are independently selected from H, halo, C$_{1-6}$ alkyl, Cy, C$_{1-6}$ haloalkyl, halosulfanyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl is optionally substituted with 1, 2, 3, 4, or 5 substituents selected from CN, NO$_2$, Cy, Cy-(C$_{1-6}$ alkyl)-, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, C(=NR$^i$)NR$^{c4}$R$^{d4}$, NR$^{c4}$C(=NR$^i$)NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, $R^2$, $R^3$, $R^4$, $R^5$, $R^6$, and $R^7$ are independently selected from H, halo, $C_{1-6}$ alkyl, Cy, $C_{1-6}$ haloalkyl, halosulfanyl, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)R^{b4}$, $S(O)_2R^{b4}$, and $S(O)_2NR^{c4}R^{d4}$; wherein said $C_{1-6}$ alkyl is optionally substituted with 1, 2, 3, 4, or 5 substituents selected from CN, $NO_2$, Cy, Cy-($C_{1-6}$ alkyl)-, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $C(=NR^i)NR^{c4}R^{d4}$, $NR^{c4}C(=NR^i)NR^{c4}R^{d4}$, $S(O)R^{b4}$, $S(O)NR^{c4}R^{d4}$, $S(O)_2R^{b4}$, and $S(O)_2NR^{c4}R^{d4}$.

In some embodiments, $R^2$, $R^3$, $R^4$, $R^5$, $R^6$, and $R^7$ are independently selected from H, halo, $C_{1-6}$ alkyl, Cy, $C_{1-6}$ haloalkyl, halosulfanyl, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)OR^{a4}$, $NR^{c4}S(O)_2R^{b4}$, $S(O)_2R^{b4}$, and $S(O)_2NR^{c4}R^{d4}$; wherein said $C_{1-6}$ alkyl is optionally substituted with 1, 2, 3, 4, or 5 substituents selected from CN, $NO_2$, Cy, Cy-($C_{1-6}$ alkyl)-, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $C(=NR^i)NR^{c4}R^{d4}$, $NR^{c4}C(=NR^i)NR^{c4}R^{d4}$, $S(O)R^{b4}$, $S(O)NR^{c4}R^{d4}$, $S(O)_2R^{b4}$, and $S(O)_2NR^{c4}R^{d4}$.

In some embodiments, $R^2$, $R^3$, $R^4$, $R^5$, $R^6$, and $R^7$ are independently selected from H, halo, $C_{1-6}$ alkyl, Cy, $C_{1-6}$ haloalkyl, halosulfanyl, CN, $NO_2$, $OC_{1-6}$ alkyl, $SC_{1-6}$ alkyl, $C(O)C_{1-6}$ alkyl, $NH_2$, $NR^{c4}C(O)C_{1-6}$ alkyl, $NR^{c4}S(O)_2C_{1-6}$ alkyl, $S(O)_2C_{1-6}$ alkyl; wherein said $C_{1-6}$ alkyl is optionally substituted with 1, 2, 3, 4, or 5 substituents selected from CN, $NO_2$, Cy, Cy-($C_{1-6}$ alkyl)-, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $C(=NR^i)NR^{c4}R^{d4}$, $NR^{c4}C(=NR^i)NR^{c4}R^{d4}$, $S(O)R^{b4}$, $S(O)NR^{c4}R^{d4}$, $S(O)_2R^{b4}$, and $S(O)_2NR^{c4}R^{d4}$.

In some embodiments, at least one of $R^2$, $R^3$, $R^4$, $R^5$, $R^6$, and $R^7$ is H.

In some embodiments, at least two of $R^2$, $R^3$, $R^4$, $R^5$, $R^6$, and $R^7$ is H.

In some embodiments, at least three of $R^2$, $R^3$, $R^4$, $R^5$, $R^6$, and $R^7$ is H.

In some embodiments, at least four of $R^2$, $R^3$, $R^4$, $R^5$, $R^6$, and $R^7$ is H.

In some embodiments, at least one of $R^1$ and $R^2$ is H.

In some embodiments, $R^1$ and $R^2$ are both H.

In some embodiments, $R^i$ is H.

In some embodiments, $R^i$ is CN.

In some embodiments, $R^i$ is $C(O)NH_2$.

In some embodiments, $R^i$ is $C_{1-6}$ alkyl.

In some embodiments, $R^i$ is H or $C_{1-6}$ alkyl.

In some embodiments, the compound has Formula II:

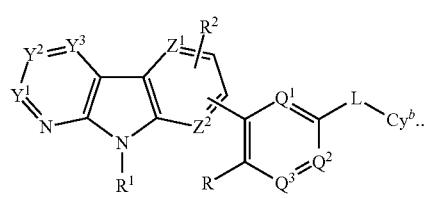

II

In some embodiments, the compound has Formula IIA:

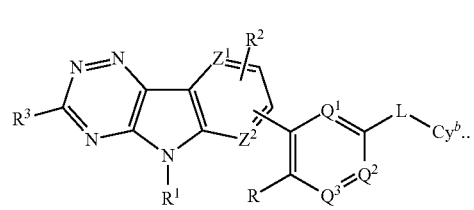

IIA

In some embodiments, the compound has Formula IIB:

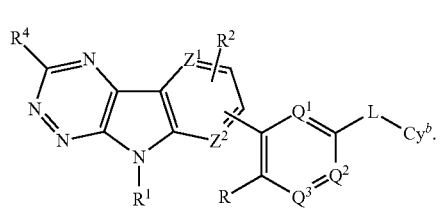

IIB

In some embodiments, the compound has Formula IIC:

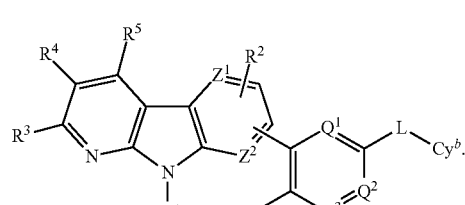

IIC

In some embodiments, the compound has Formula IID:

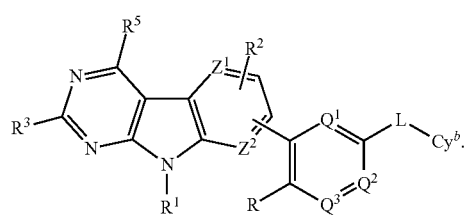

IID

In some embodiments, the compound has Formula IIE:

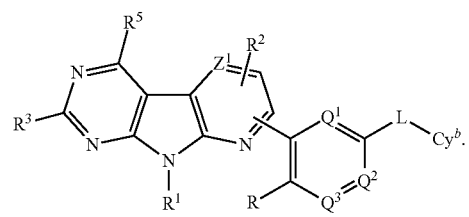

IIE

In some embodiments, the compound has Formula IIF:

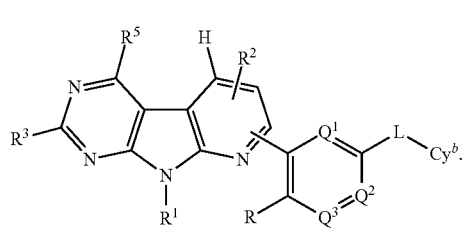

IIF

In some embodiments, the compound has Formula IIG:

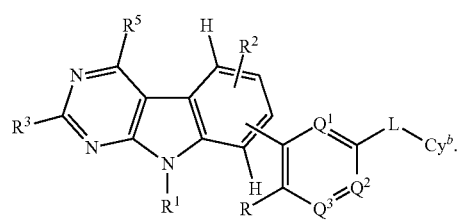

IIG

In some embodiments, the compound has Formula IIH:

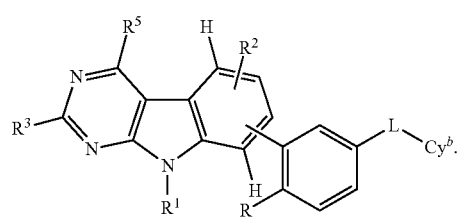

IIH

In some embodiments, the compound has Formula III:

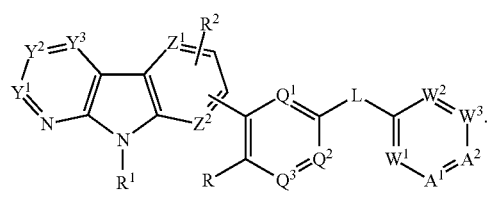

III

In some embodiments, the compound has Formula IIIA:

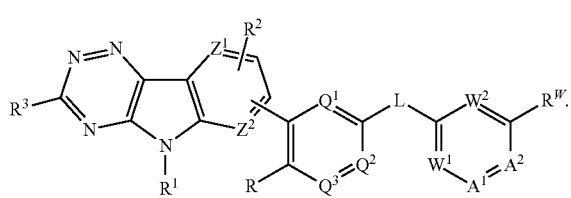

IIIA

In some embodiments, the compound has Formula IIIB:

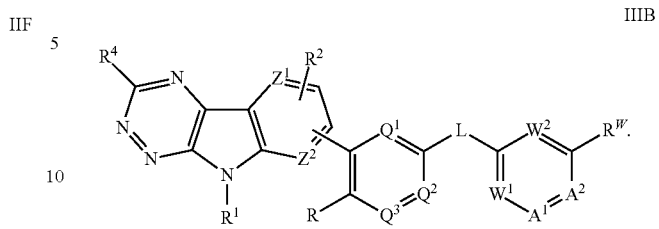

IIIB

In some embodiments, the compound has Formula IIIC:

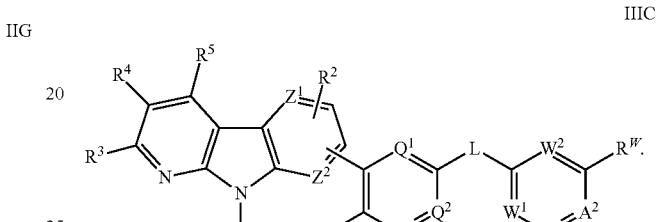

IIIC

In some embodiments, the compound has Formula IIID:

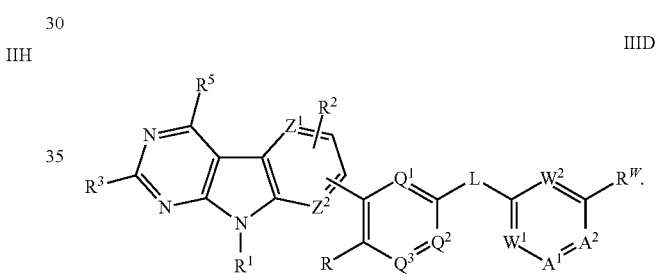

IIID

In some embodiments, the compound has Formula IIIE:

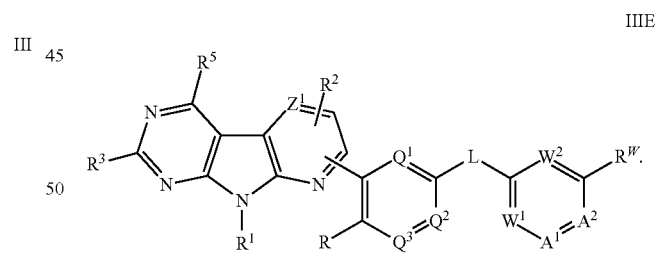

IIIE

In some embodiments, the compound has Formula IIIF:

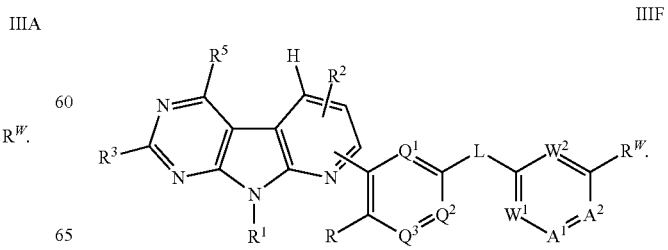

IIIF

In some embodiments, the compound has Formula IIIG:

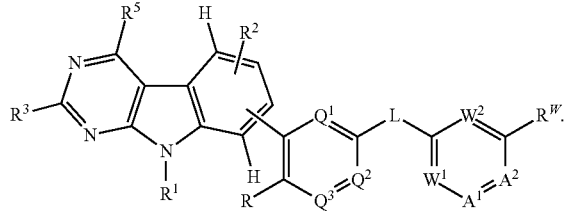

IIIG

In some embodiments, the compound has Formula IIIH:

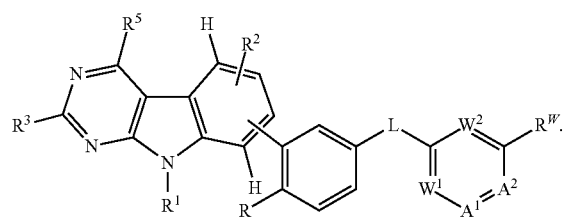

IIIH

In some embodiments, the compound has Formula IIIJ:

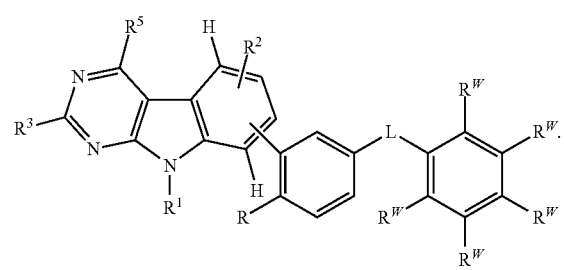

IIIJ

In some embodiments, the compound has Formula IIIK:

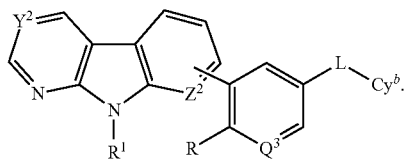

III K

In some embodiments, the compound has Formula IVA or IVB:

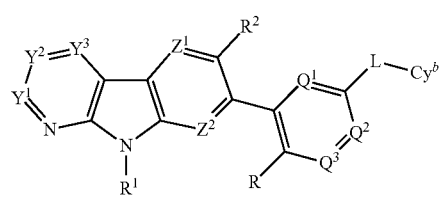

IVA

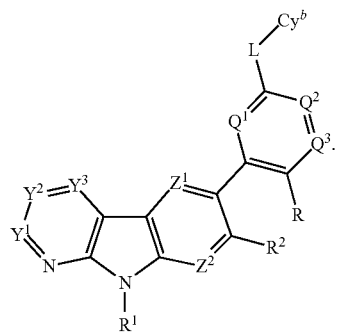

IVB

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, sec-butyl, t-butyl), pentyl (e.g., n-pentyl, isopentyl, sec-pentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. A linking alkyl group is referred to herein as "alkylene."

As used herein, "alkenyl" refers to an alkyl group having one or more carbon-carbon double bonds. Example alkenyl groups include ethenyl, propenyl, cyclohexenyl, and the like. A linking alkenyl group is referred to herein as "alkenylene."

As used herein, "alkynyl" refers to an alkyl group having one or more carbon-carbon triple bonds. Example alkynyl groups include ethynyl, propynyl, and the like. A linking alkynyl group is referred to herein as "alkynylene."

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "halosulfanyl" refers to a sulfur group having one or more halogen substituents. Example halosulfanyl groups include pentahalosulfanyl groups such as $SF_5$.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. A linking aryl group is referred to herein as "arylene."

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of cyclopentane, cyclopentene, cyclohexane, and the like. A cycloalkyl group containing a fused aromatic ring can be attached through any ring-forming atom including a ring-forming atom of the fused aromatic ring. A linking cycloalkyl group is referred to herein as "cycloalkylene."

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, any ring-forming N in a heteroaryl moiety can be substituted by oxo. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. A linking heteroaryl group is referred to herein as "heteroarylene."

As used herein, "heterocycloalkyl" refers to non-aromatic heterocycles having one or more ring-forming heteroatoms such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. The heterocycloalkyl group can be attached through a ring-forming carbon atom or a ring-forming heteroatom. The heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds. A linking heterocycloalkyl group is referred to herein as "heterocycloalkylene."

As used herein, "hydrocarbyl" refers to any moiety comprising only hydrogen and carbon atoms. Example "hydrocarbyl" groups include alkyl, alkenyl, alkynyl, cycloalkyl, cycloalkenyl, aryl, arylalkyl and arylalkenyl groups.

As used herein, "halo" or "halogen" includes fluoro, chloro, bromo, and iodo.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "alkoxy" refers to an —O-alkyl group. Example alkoxy groups include methoxy, ethoxy, propoxy (e.g., n-propoxy, isopropoxy),t-butoxy, and the like.

As used herein, "haloalkoxy" refers to an —O-(haloalkyl) group.

As used herein, "hydroxylalkyl" refers to an alkyl group substituted by hydroxyl.

As used herein, "cyanoalkyl" refers to an alkyl group substituted by cyano. The carbon of the cyano group is typically not counted if a carbon count precedes the term. For example, cyanomethyl is considered herein to be a $C_1$ cyanoalkyl group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereos elective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methyl-benzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1, 2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

The term, "compound," as used herein is meant to include all stereoisomers, geometric isomers, tautomers, and isotopes of the structures depicted.

All compounds, and pharmaceutically acceptable salts thereof, can be found together with other substances such as water and solvents (e.g. hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which is was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Compounds of the invention can be prepared according to numerous preparatory routes known in the literature. Example synthetic methods for preparing compounds of the invention are provided in the Schemes below.

Certain compounds of the invention where L is NHCO and N is attached to Cy$^a$, may be synthesized, for example, by following the synthetic sequence described in Scheme 1

According to Scheme 1, a substituted aniline 1-1 can be treated with an acid chloride 1-2 (Y=Cl) in the presence of a base, or with a carboxylic acid 1-2 (Y=OH) in the presence of a coupling agent such as HATU, to give the corresponding diarylamide 1-3.

Amide 1-3 can be coupled with the appropriate meta- or para-nitrophenyl boronic acid or boronic ester 1-4 in the presence of a palladium catalyst under, for example, Suzuki coupling conditions to give the biaryl 1-5. The nitro group can be reduced, for example, by the use of a reducing agent such as iron, SnCl$_2$, or Na$_2$S$_2$O$_4$. Alternatively the nitro group can be reduced with H$_2$ and a catalyst to give the corresponding aniline. The reduction step may be eliminated if an aminophenyl boronic acid is used in place of 1-4.

The aniline intermediate can be coupled with 4-chloro-5-iodopyrimidine under thermal, acidic or basic conditions to give the anilinopyrimidine 1-6. Intermediate 1-6 can be cyclized, for example, under Heck reaction conditions, such as, for example in the presence of palladium acetate, a triarylphoshine and a base such as sodium acetate, in a polar aprotic solvent such as dimethylformamide (DMF) to give pyrimido[4,5-b]indoles of formula I-7, wherein the orientation of the moiety bonded to the pyrimidoindole ring depends on the substitution pattern of the nitro boronic acid or boronic ester 1-4.

Scheme 1

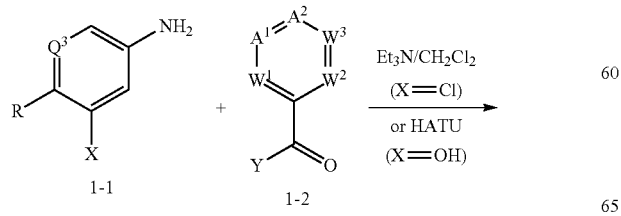

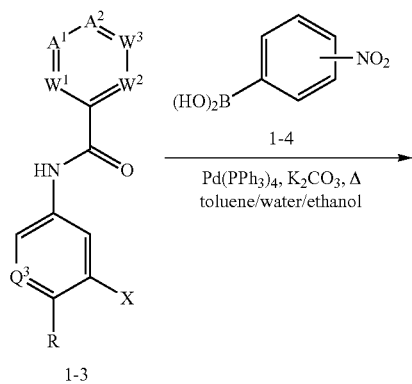

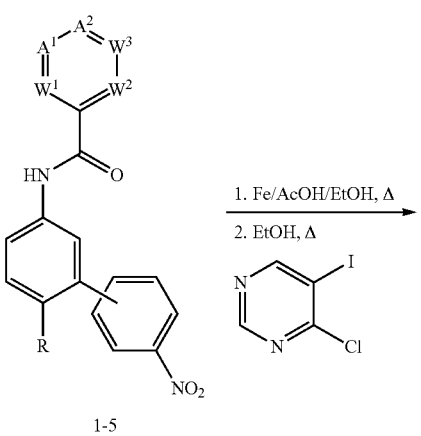

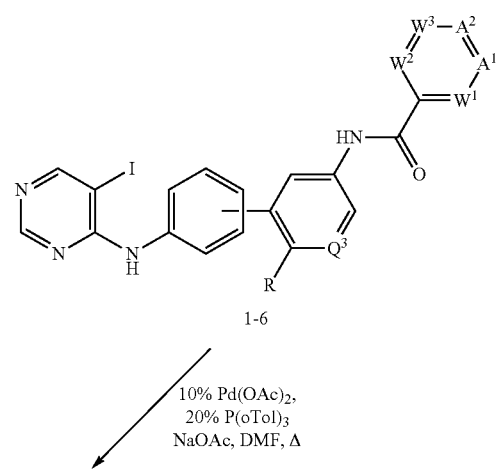

-continued

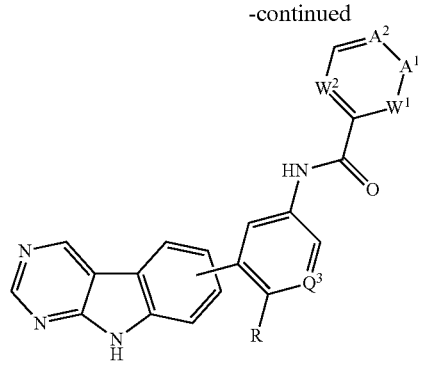

1-7

Compounds with alternative substitution on the aromatic ring moiety (Cy$^b$ in Formula I) derived from intermediate 1-2 in Scheme 1 can be synthesized directly, for example, by following synthetic Scheme 2

According to Scheme 2, reaction of the 3-fluoro-5-trifluoromethyl aromatic amide 2-1a derivative with any of a variety of aliphatic, heterocyclic, and heteroaromatic amines such as morpholine, piperidine, piparazine, 3-dimethylamino propylamine, imidazole, triazole and their substituted analogs gave the corresponding 3-amino-5-trifluoromethyl aromatic amide analogs 2-2a. Alternatively the 3-bromo-5-trifluoromethyl aromatic amide 2-1b derivative can undergo Suzuki or Negishi or Buchwald coupling to give the corresponding 3-aryl or heteroaryl analogs 2-2b.

Scheme 2

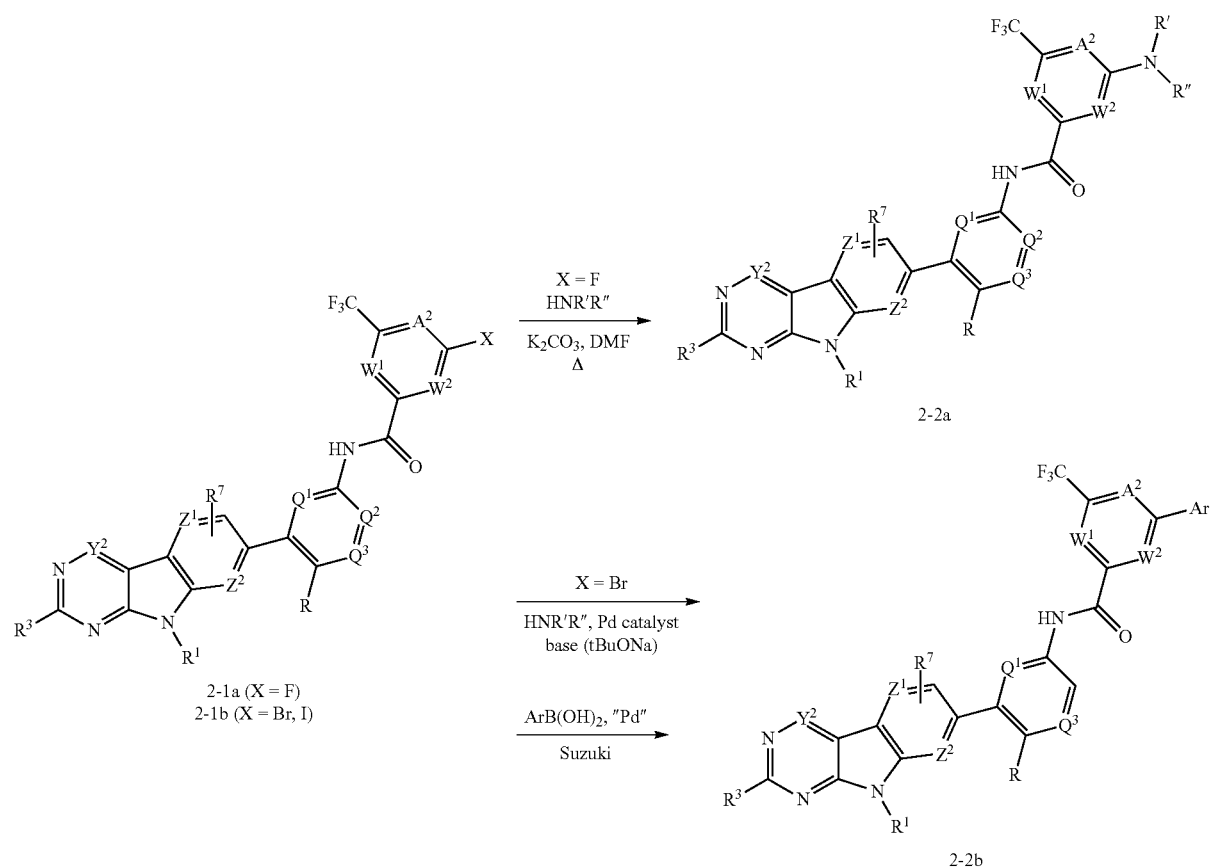

The aromatic amides, such as those prepared according to Scheme 2, can be hydrolyzed, for example, using a base such as LiOH, NaOH or KOH, to provide the corresponding aromatic amine. The formed amide (e.g., 2-2a and 2-2b) can be converted, for example, via Scheme 3, to a different amide 3-1, or a urea 3-1 using a benzoic acid, an acid chloride or an isocyanate.

Scheme 3

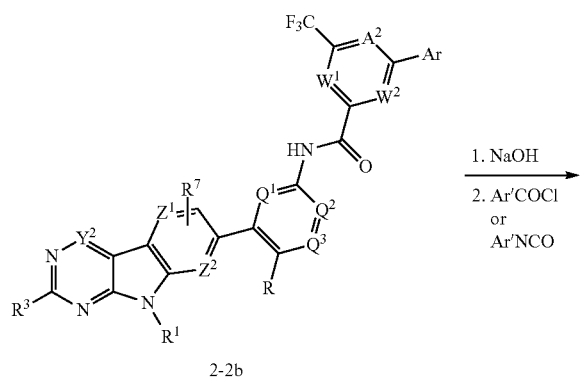

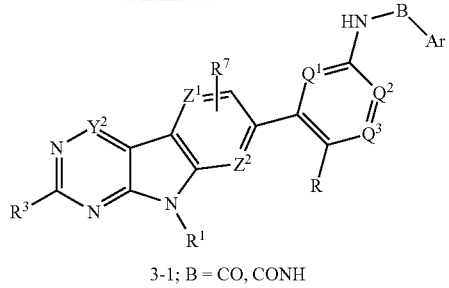

3-1; B = CO, CONH

The regioisomeric amides 1-7 (L is CONH, where the C of the CONH is attached to $Cy^a$) can be synthesized according to the synthetic sequence in Scheme 4.

According to Scheme 4, a carboxylic acid or an acid chloride 4-1 (Y=Cl, OH) may be coupled with an amine 4-2 under conditions described in Scheme 1 to give the amide 4-3. This amide may be coupled with a meta- or para-nitrophenyl boronic acid or boronic ester 4-4, similarly to Scheme 1, under, for example, Suzuki coupling conditions to give the corresponding biphenyl compound 4-5. The nitro group of 4-5 may be reduced, for example, under catalytic hydrogenation conditions, e.g., Fe and acid, or $Na_2S_2O_4$ to give the amine analogs 4-6, which may be coupled with 4-chloro-5-iodopyrimidine to give the anilinopyrimidine 4-7. The anilinopyrimidine 4-7 may be subjected to Heck cyclization similarly to Scheme 1 to provide 4-8, wherein the substitution position on the pyrimidoindole ring system is determined by the substitution pattern of intermediate 4-4.

Scheme 4

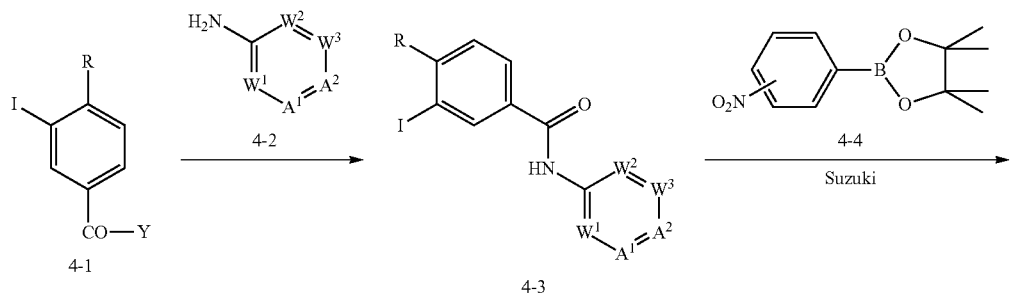

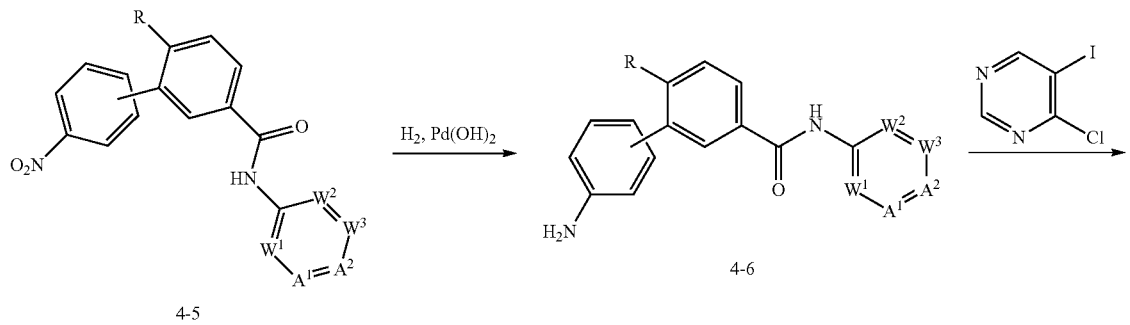

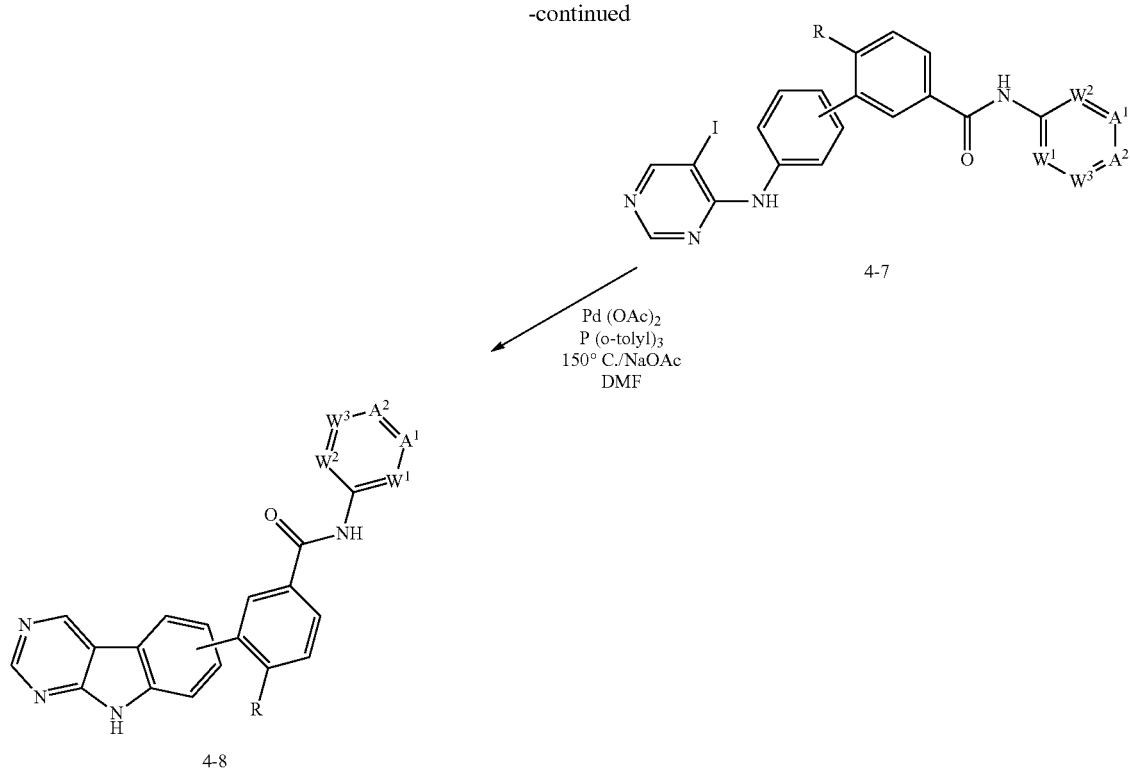

An alternative route to amide 4-8 is shown in Scheme 5. According to Scheme 5, a halogen substituted benzoic acid 5-2, was coupled with a boronic acid or boronic ester 5-1 under, for example, Suzuki coupling conditions to give the corresponding biphenyl 5-3. This biphenyl compound was converted to the aniline biphenyl 5-4 by reduction of the nitro group under, for example, conditions describe in Scheme 1. Intermediate 5-4 could be coupled with 4-chloro-5-iodopyrimidine to give the anilinopyrimidine 5-5, which could be subjected to intramolecular Heck reaction conditions to give the corresponding carboxylic acid 5-6. Carboxylic acid 5-6 can be coupled with any of a variety of aromatic amines to provide compounds of Formula 4-8.

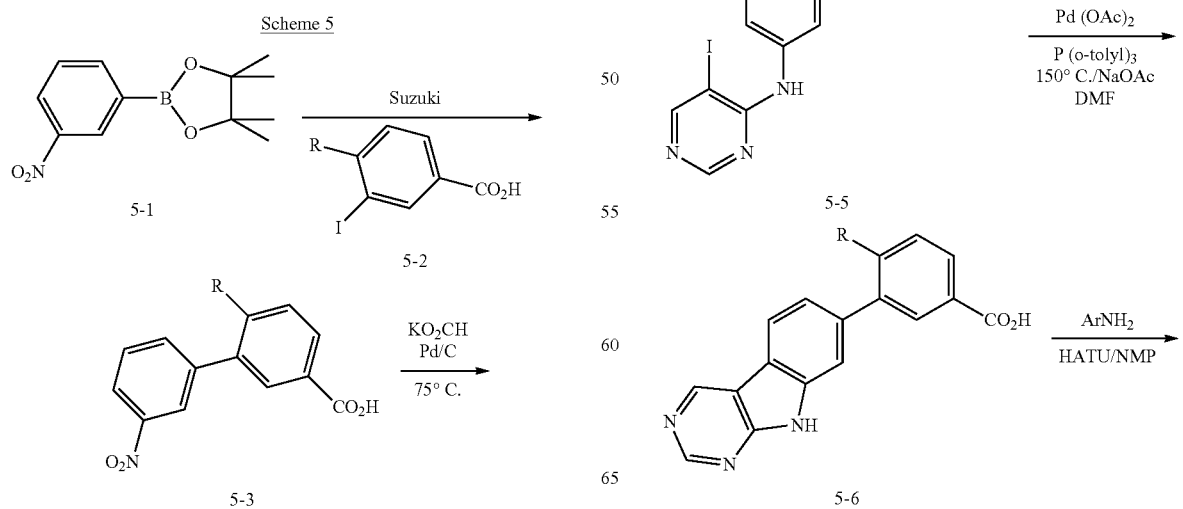

-continued

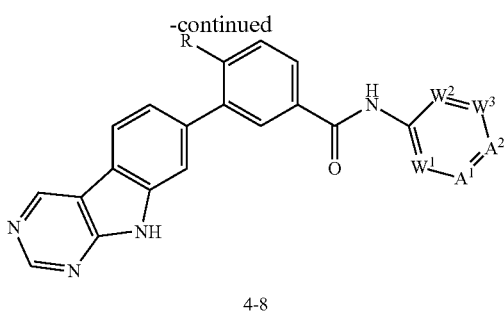

4-8

Compounds with 2-aminopyrimidine substitution can be synthesized, for example, following synthetic Scheme 6. The intermediate 6-1, wherein the nitro group is meta- or para-, may be coupled with 2,4-dichloro-5-iodopyrimidine to give the corresponding 4-anilino-2-chloro-5-iodopyrimidine 6-2. The 2-chloro substituent may be displaced with thiomethyl by treatment with a thiol salt such as sodium thiomethoxide in a solvent such as isopropanol to provide the thioether, 6-4. The 2-thiomethyl group may be oxidized to the corresponding sulfone by treatment with an oxidizing agent such as m-chloroperbenzoic acid (mCPBA), oxone, $H_2O_2$, $KMnO_4$ or other known oxidizing agent. The sulfone group may then be displaced with an amine or ammonia by heating with a solution of the desired amine to provide compounds of Formula 6-3; wherein the substitution position on the pyrimido-indole ring system is determined by the substitution position of the nitro group on 6-1.

Scheme 6

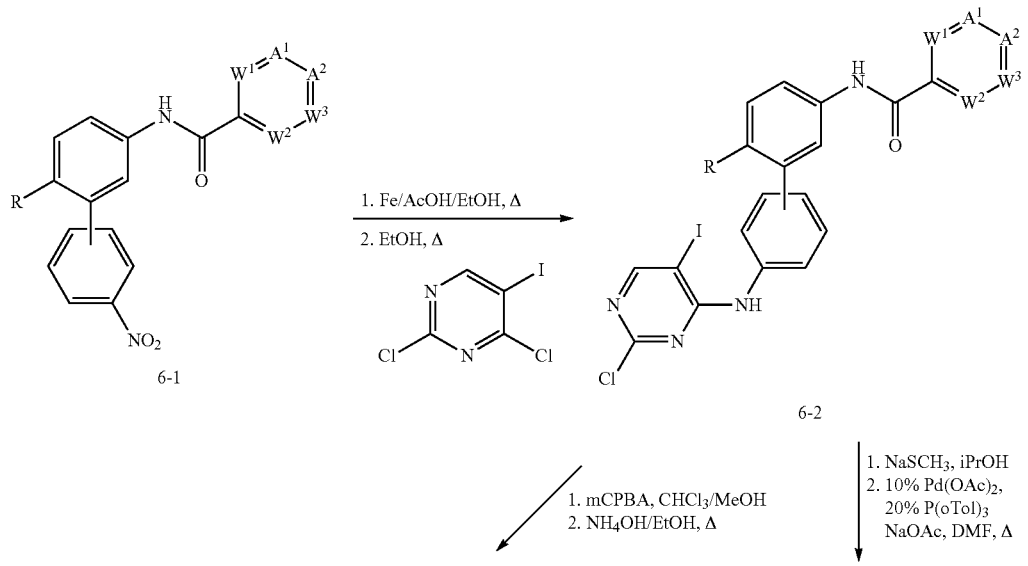

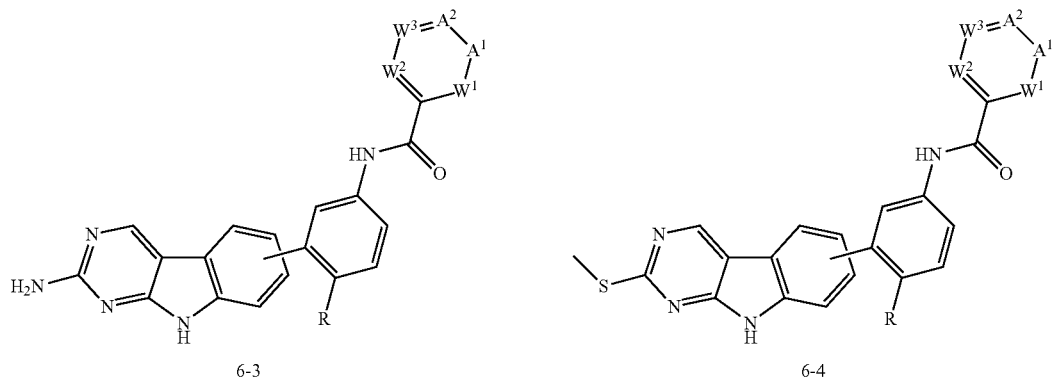

Certain pyrido[4,5-b]indoles where L is CONH, may be synthesized, for example, by following the synthetic sequence described in Scheme 7.

According to Scheme 7, a substituted benzoic acid 7-1 can be converted to the corresponding acid chloride which may then be treated with a substituted aniline 7-2, in the presence of a base, to give the corresponding diarylamide 7-3.

Amide 7-3 can be coupled with the appropriate meta- or para-nitrophenyl boronic acid or boronic ester 7-4 in the presence of a palladium catalyst under, for example, Suzuki coupling conditions to give the biaryl 7-5. The nitro group can be reduced, for example, by the use of a reducing agent such as iron, $SnCl_2$, or $Na_2S_2O_4$. Alternatively the nitro group can be reduced with $H_2$ and a catalyst to give the corresponding aniline 7-6. The reduction step is eliminated if an aminoboronic acid is used in place of nitrophenylboronic acid 7-4.

The aniline intermediate can be coupled with 2-chloro-3-bromopyridine under thermal, acidic or basic conditions to give the anilinopyridine 7-7. Intermediate 7-7 can be cyclized, for example, under Heck reaction conditions, such as, for example in the presence of palladium acetate, a tri-arylphoshine and a base such as sodium acetate, in a polar aprotic solvent such as DMF to give pyrido[4,5-b]indoles of formula 7-8, wherein the orientation of the moiety bonded to the pyridinoindole ring depends on the substitution pattern of the nitro boronic acid or boronic ester 7-4.

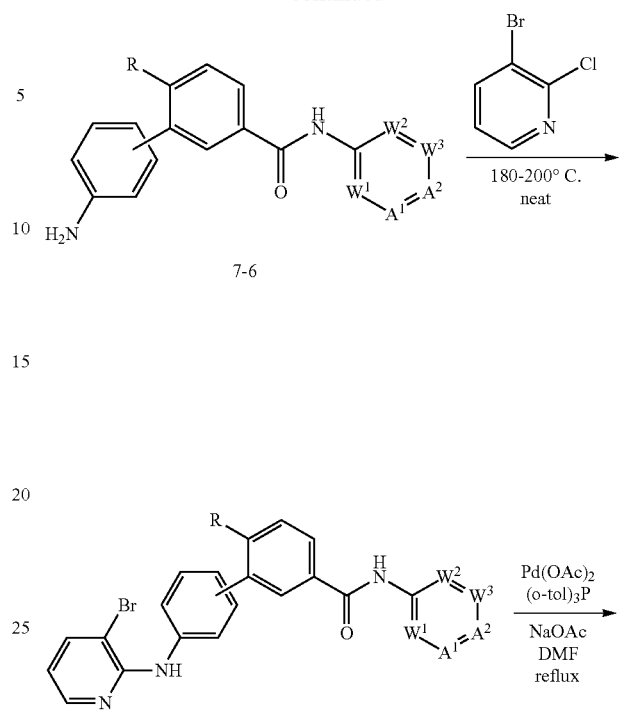

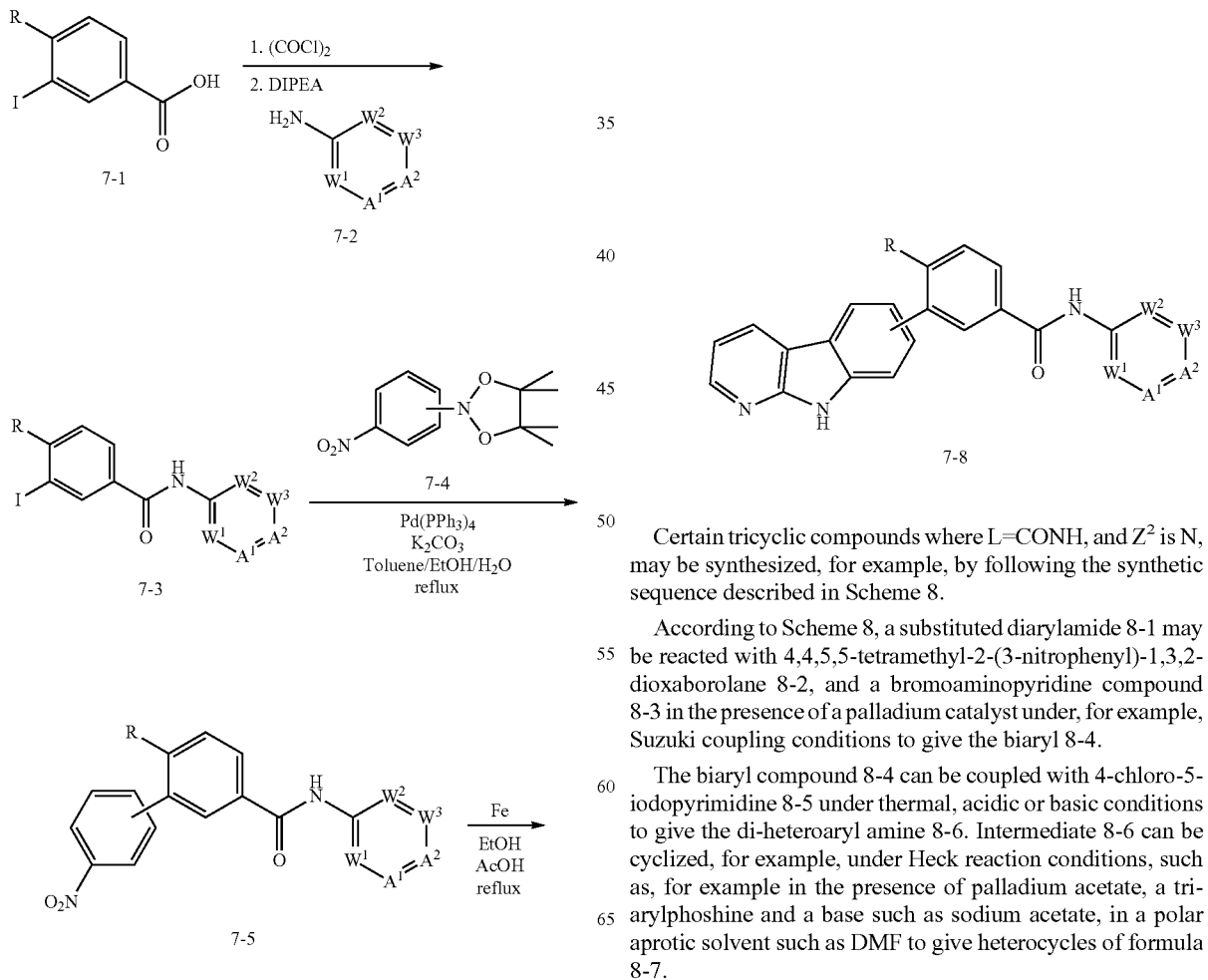

Certain tricyclic compounds where L=CONH, and $Z^2$ is N, may be synthesized, for example, by following the synthetic sequence described in Scheme 8.

According to Scheme 8, a substituted diarylamide 8-1 may be reacted with 4,4,5,5-tetramethyl-2-(3-nitrophenyl)-1,3,2-dioxaborolane 8-2, and a bromoaminopyridine compound 8-3 in the presence of a palladium catalyst under, for example, Suzuki coupling conditions to give the biaryl 8-4.

The biaryl compound 8-4 can be coupled with 4-chloro-5-iodopyrimidine 8-5 under thermal, acidic or basic conditions to give the di-heteroaryl amine 8-6. Intermediate 8-6 can be cyclized, for example, under Heck reaction conditions, such as, for example in the presence of palladium acetate, a tri-arylphoshine and a base such as sodium acetate, in a polar aprotic solvent such as DMF to give heterocycles of formula 8-7.

Scheme 8

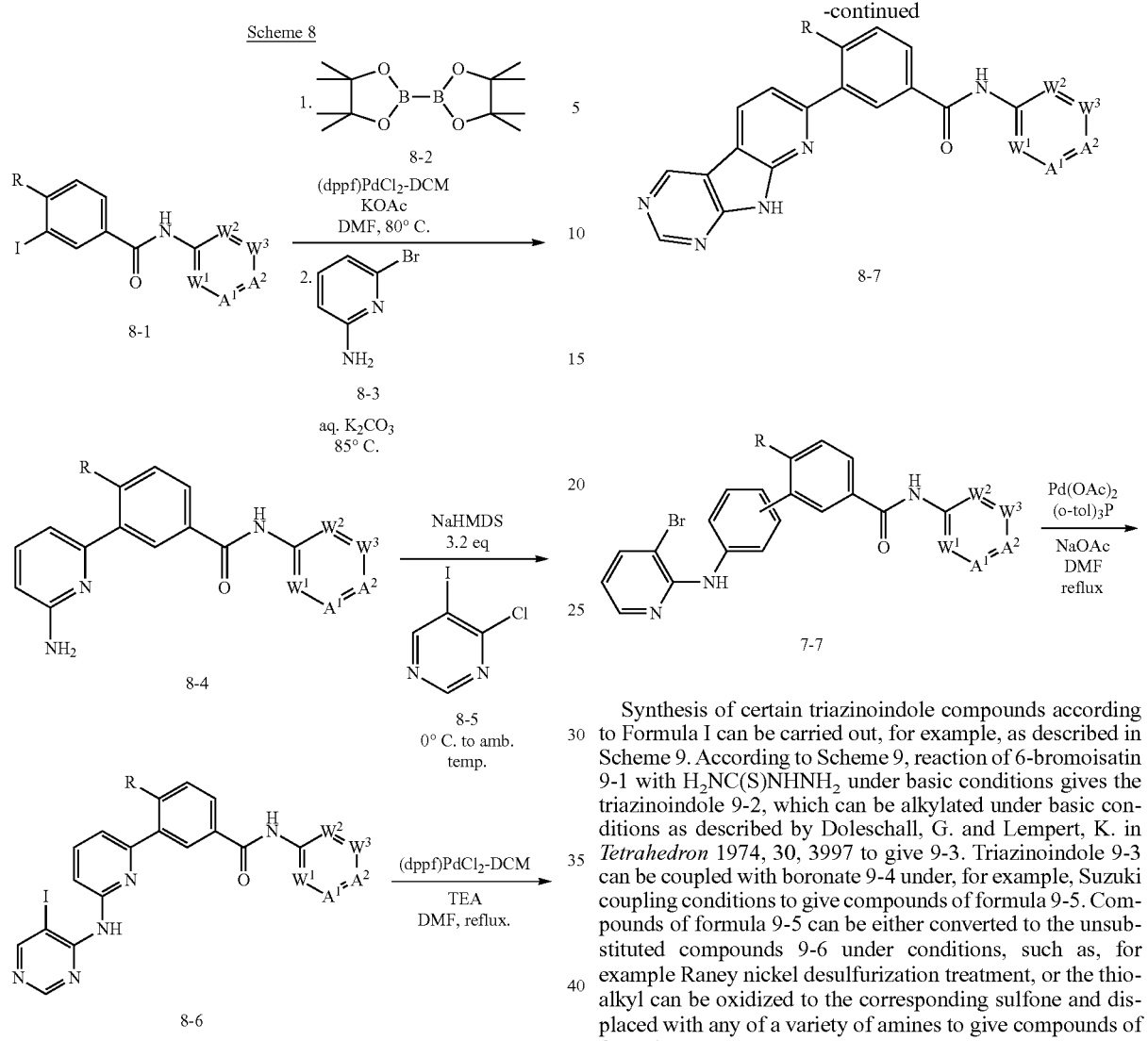

Synthesis of certain triazinoindole compounds according to Formula I can be carried out, for example, as described in Scheme 9. According to Scheme 9, reaction of 6-bromoisatin 9-1 with $H_2NC(S)NHNH_2$ under basic conditions gives the triazinoindole 9-2, which can be alkylated under basic conditions as described by Doleschall, G. and Lempert, K. in *Tetrahedron* 1974, 30, 3997 to give 9-3. Triazinoindole 9-3 can be coupled with boronate 9-4 under, for example, Suzuki coupling conditions to give compounds of formula 9-5. Compounds of formula 9-5 can be either converted to the unsubstituted compounds 9-6 under conditions, such as, for example Raney nickel desulfurization treatment, or the thioalkyl can be oxidized to the corresponding sulfone and displaced with any of a variety of amines to give compounds of formula 9-7.

Scheme 9

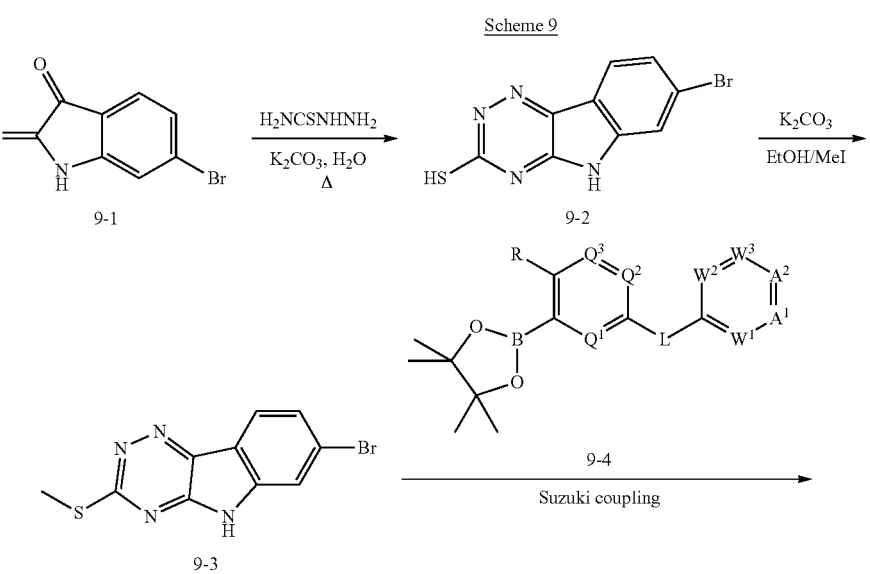

-continued

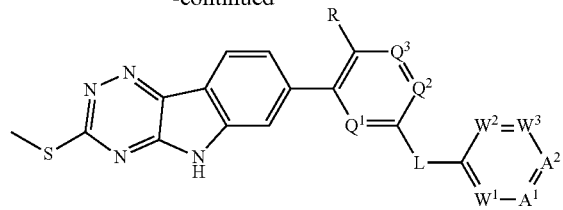

9-5

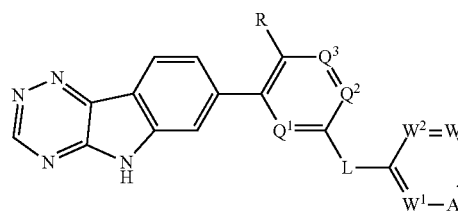

9-6

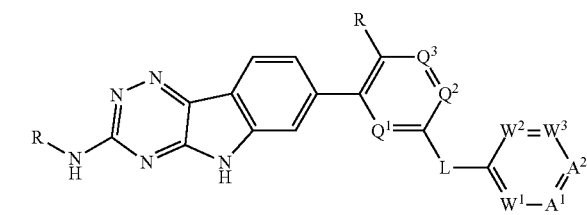

9-7

Synthesis of certain, other triazinoindole compounds according to Formula I can be carried out, for example, as described in Scheme 10. According to Scheme 10, reaction of 6-bromoisatin 10-1 with POCl₃, followed by H₂NC(S)NHNH₂ and cyclization gives the triazinoindole 10-2, according to the procedure of Bell, Malcolm R.; Zalay, Andrew W. *Journal of Heterocyclic Chemistry* 1975, 12, 1001. Compound 10-2 can be S-alkylated under basic conditions as described by Doleschall, G. and Lempert, K. in *Tetrahedron* 1974, 30, 3997 to give 10-3. Triazinoindole 10-3 can be coupled with boronate 10-4 under, for example, Suzuki coupling conditions to give triazinoindole compounds of formula 10-5. Compounds of formula 10-5 can be can be converted to the triazinoindoles 10-6 by removal of the thioalkyl group under a variety of conditions such as Raney Ni. Alternatively the thioalkyl group of 10-5 can be displaced with an alkylamine to produce 10-7, for example, by direct displacement, or by following the oxidation to the corresponding sulfone and displacement protocol.

Scheme 10

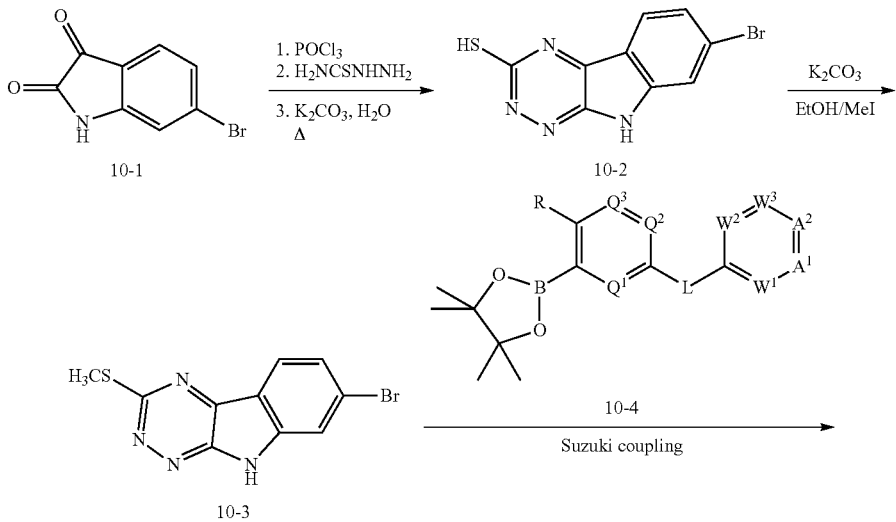

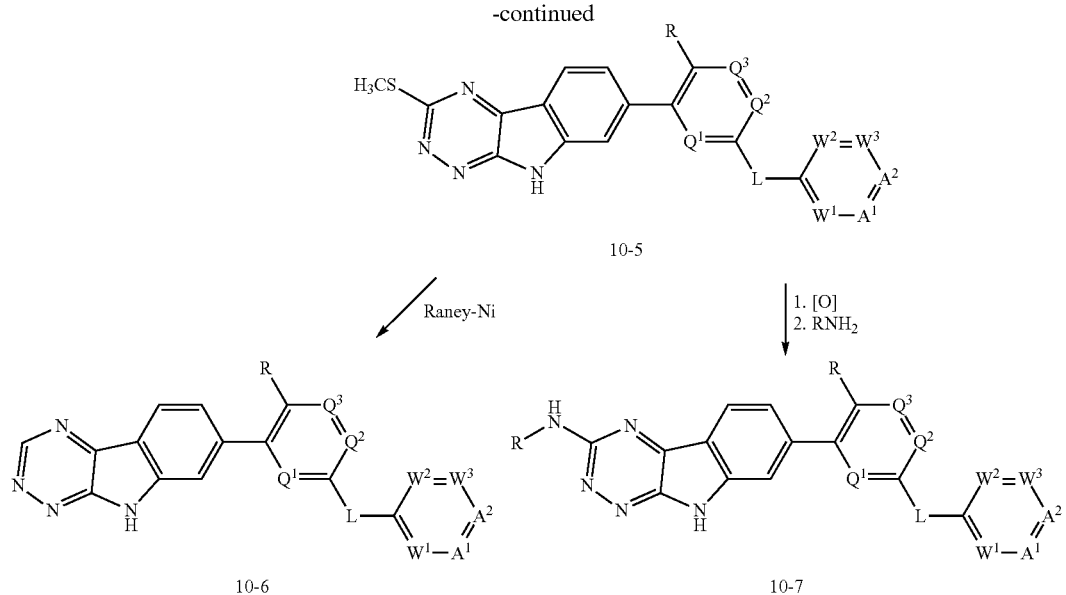

In all of the Schemes described herein, if there are functional groups present on a substituent group such as $Y^1$, $Y^2$, $W^1$, $A^1$, R, $R^1$, $R^5$, etc., further modification can be made if appropriate and desired. For example, a CN group can be hydrolyzed to afford an amide group; a carboxylic acid can be converted to a ester, which in turn can be reduced to an alcohol, which in turn can be further modified. In another example, an OH group can be converted into a better leaving group such as mesylate, which in turn is suitable for nucleophilic substitution, such as by CN. One skilled in the art will recognize such further modifications.

Methods

Compounds of the invention can modulate activity of one or more various kinases including, for example, Janus kinases (JAKs) and ABL or variants thereof (e.g. JAK2 V617F and ABL1 T315I). The term "modulate" is meant to refer to an ability to increase or decrease the activity of the kinase. Accordingly, compounds of the invention can be used in methods of modulating kinases, such as a JAK kinase or ABL, by contacting the kinase with any one or more of the compounds or compositions described herein. In some embodiments, compounds of the present invention can act as inhibitors of one or more kinses. In further embodiments, the compounds of the invention can be used to modulate activity of a kinase in an individual in need of modulation of the receptor by administering a modulating amount of a compound of the invention.

In some embodiments, the compounds of the invention can modulate both JAK and ABL. The potential advantages of a dual kinase inhibitors include the following. Cancer cell growth and survival are impacted by multiple signaling pathways. As an example, the transformative effects of murine v-Abl and BCR/ABL1 have been blocked or inhibited by disabling multiple pathways (Ras, Rac, INK, PI3K, PKC, and mTOR). Although constitutive STAT activation has been observed in ABL transformed cells, this may occur independently of the JAK kinases illustrating how multiple signaling pathways may contribute to a disease state (M G Karas et al., Blood, 2004, 103:4268-4275; X. Zou and K. Calame, JBC, 274(26):18141-18144; MG Kharas and DA Fruman, Cancer Research, 65:2047-2053). Accordingly, having a single compound that targets two kinases with effecting different signaling pathways may improve the efficacy of treatment and reduce the odds that a drug resistant cell will arise and expand clonally.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate include receptor and non-receptor Ser/Thr kinases such as TGF-βR, PKA, PKG, PKC, CaM-kinase, phosphorylase kinase, MEKK, ERK, MAPK, Akt, and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK, or ABL. Certain JAKs include JAK1, JAK2, JAK3 or TYK2. In some embodiments, the JAK is JAK1 or JAK2. In some embodiments, the JAK is JAK2. In some embodiments, the JAK is mutant. In some embodiments, the mutant JAK carries the V617F, F537-K539delinsL, H538QK539L, K539L, or N542-E543del in mutations in JAK2. In some embodiments, the non-receptor Tyr kinase is ABL such as ABL1 or ARG (ABL2). In some embodiments, the ABL is mutant. In some embodiments, the mutant ABL carries the T315I mutation. In some embodiments, the mutant ABL carries the T315D, F359D, D276G, E255K, M351T, G250E, H396R, Q252H, Y253H, E355G, F317L, G250E, Y253F, F359V, Q252R, L387M, M244V, M343T/F382L, or V379I mutation. In some embodiments, both JAK and ABL kinase activities are modulated. In some embodiments, the kinase results from the fusion of multiple genes such as where the fusion occurs between two genes as follows: BCR/ABL1, TEL/ABL1, NUP214/ABL1, EMS/ABL1, SFQ/ABL1, BCR/ARG, TEL/ARG, TEL/PDGFβR, HIP1/PDGFβR, RAB5/PDGFβR, H4/PDGFβR, Myomegalin/PDGFβR, CEV14/PDGFβR, NIN1/PDGFβR, HCMOGT/PDGFβR, KIAA1509/PDGFβR, TP53BP1/PDGFβR, FIIP1L1/PDGFαR, BCR/PDGFαR, BCR/JAK2, TEL/JAK2, PCM1/JAK2, TEL/SYK, TEL/TRKC, ZNF198/FGFR1, FOP/FGFR1, CEP110/FGFR1, HERVK/FGFR1, BCR/FGFR1, FGFR1OP2/FGFR1, TIF1/FGFR1, TEL/FGFR3, TEL/FLT3, TEL/FRK, NPM/ALK, TPM3/ALK, TFG/ALK, ATIC/ALK, CLTC/ALK, MSN/ALK, TPM4/ALK, ALO17/ALK, RANBP2/ALK, MYH9/ALK, CARS/ALK Kinases to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3. Kinases to which the present compounds bind and/or modulate include any member of the ABL family. In some embodiments, the ABL is ABL1 or ARG (ABL2). In some embodiments, the ABL is ABL1.

In some embodiments, the compound is a dual inhibitor and inhibits both ABL1 and JAK2

In some embodiments, more than one compound of Formula I is used to inhibit the activity of one kinase.

In some embodiments, more than one compound of Formula I is used to inhibit more than one kinase, such as at least two kinases (e.g., ABL1 and JAK2).

In some embodiments, the compound is used in combination with another kinase inhibitor to inhibit the activity of one kinase.

In some embodiments, the compound is used in combination with another kinase inhibitor to inhibit the activities of more than one kinase.

The compounds of the invention can be selective. By "selective" is meant that the compound binds to or inhibits a kinase with greater affinity or potency, respectively, compared to at least one other kinase. In some embodiments, the compounds of the invention are selective inhibitors of JAK1 or JAK2 over JAK3 and/or TYK2. In some embodiments, the compounds of the invention are selective inhibitors of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity can be at least about 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the Km ATP concentration of each enzyme. In some embodiments, selectivity of compounds of the invention for JAK2 over JAK3 can be determined at the cellular ATP concentration. In some embodiments, the selectivity of compounds of the invention can be determined by cellular assays associated with particular JAK kinase activity.

In some embodiments, compound is a selective inhibitor of ABL1 over ARG (ABL2).

Another aspect of the present invention pertains to methods of treating a kinase-associated disease or disorder in an individual (e.g., patient) by administering to the individual in need of such treatment a therapeutically effective amount or dose of a compound of the present invention or a pharmaceutical composition thereof. A kinase-associated disease can include any disease, disorder or condition that is directly or indirectly linked to expression or activity of the kinase, including over-expression and/or abnormal activity levels. Abnormal activity levels can be determined by comparing activity level in normal, healthy tissue or cells with activity level in diseased cells. A kinase-associated disease can also include any disease, disorder or condition that can be prevented, ameliorated, or cured by modulating kinase activity. In some embodiments, the disease is characterized by the abnormal activity of JAK, ABL, or both. In some embodiments, the disease is characterized by mutant JAK2, such as where the mutation resides in the pseudo-kinase domain. In some embodiments, the disease is characterized by mutant ABL, such as where the mutation resides in the kinase domain.

Examples of kinase-associated diseases include diseases involving the immune system including, for example, organ transplant rejection (e.g., allograft rejection and graft versus host disease).

Further examples of kinase-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of kinase-associated diseases include allergic conditions such as asthma, food allergies, atopic dermatitis and rhinitis. Further examples of kinase-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of kinase-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one kinase inhibitor of the invention together with the agent causing unwanted sensitization can be helpful in treating such unwanted sensitization or dermatitis. In some embodiments, the skin disorder is treated by topical administration of at least one kinase inhibitor of the invention.

In further embodiments, the kinase-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma. Examples of cutaneous T-cell lymphomas include Sezary syndrome and mycosis fungoides. In further embodiments, the kinase-associated disease is endometrial and cervical cancer.

Kinase-associated diseases can further include those characterized by the presence of a mutation (genetic or epi-genetic) resulting in increased signaling from JAK kinases. These include diseases with mutated cytokine and growth factor receptors (e.g. mutant EpoR or MPL). Further, mutations downstream of JAKs which may result in a net increase in JAK pathway activation (e.g. SOCS or PIAS proteins) should also be considered kinase-associated.

Kinase-associated diseases can further include those characterized by expression of a mutant kinase. These include diseases characterized by expression of a mutant JAK2 such as those having at least one mutation in the pseudo-kinase domain (e.g., JAK2V617F) or near the pseudo-kinase domain (exon 12) (NEJM, 356:459-468; 2007)) and diseases characterized by expression of mutant ABL1 (e.g. BCR-ABL or ABL1T315I).

Kinase-associated diseases can further include myeloproliferative disorders (MPDs) such as polycythemia vera (PV), essential thrombocythemia (ET), myeloid metaplasia with myelofibrosis (MMM), chronic myelogenous leukemia (CIVIL), chronic myelomonocytic leukemia (CMML), hypereosinophilic syndrome (HES), systemic mast cell disease (SMCD), and the like.

Further kinase-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The kinase inhibitors described herein can further be used to treat ischemia reperfusion injuries or a disease or condition related to an inflammatory ischemic event such as stroke or cardiac arrest. The kinase inhibitors described herein can further be used to treat anorexia, cachexia, or fatigue such as that resulting from or associated with cancer. The kinase inhibitors described herein can further be used to treat restenosis, sclerodermitis, or fibrosis. Examples of fibrosis are renal fibrogenesis and pulmonary fibrosis. The kinase inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2.

As used herein, the term "contacting" refers to the bringing together of indicated moieties in an in vitro system or an in vivo system. For example, "contacting" a kinase with a compound of the invention includes the administration of a compound of the present invention to an individual or patient, such as a human, having a kinase, as well as, for example, introducing a compound of the invention into a sample containing a cellular or purified preparation containing the kinase.

As used herein, the term "individual" or "patient," used interchangeably, refers to any animal, including mammals, preferably mice, rats, other rodents, rabbits, dogs, cats, swine, cattle, sheep, horses, or primates, and most preferably humans. As used herein, the term "juvenile" refers to a human patient in which onset of the disease state or disorder occurs prior to the age of 18.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapies

One or more additional pharmaceutical agents such as, for example, chemotherapeutics, anti-inflammatory agents, steroids, immunosuppressants, as well as BCR-ABL1, Flt-3, EGFR, HER2, c-MET, VEGFR, PDGFR, cKit, IGF-1R, RAF and FAK kinase inhibitors such as, for example, those described in WO 2006/056399, or other agents can be used in combination with the compounds of the present invention for treatment of kinase-associated diseases, disorders or conditions. The one or more additional pharmaceutical agents can be administered to a patient simultaneously or sequentially. Therapeutic antibodies may be used in combination with the compounds of the present invention for treatment of kinase-associated diseases, disorders or conditions.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), and antibodies directed to c-MET.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec, intron, ara-C, adriamycin, Cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sm11, fludarabine, pentostatin, triapine, didox, trimidox, amidox, 3-AP, and MDL-101,731.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-ABL1 inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more kinase inhibitors of the invention can be used in combination with a chemotherapeutic in the treatment of cancer and may improve the treatment response as compared to the response to the chemotherapeutic agent alone, without exacerbation of its toxic effects. Examples of additional pharmaceutical agents used in the treatment of cancers such as multiple myeloma, for example, can include without limitation, melphalan, melphalan plus prednisone [MP], doxorubicin, dexamethasone, and Velcade (bortezomib). Further additional agents used in the treatment of multiple myeloma include Bcr-ABL1, Flt-3, RAF and FAK kinase inhibitors. Additive or synergistic effects are desirable outcomes of combining a kinase inhibitor of the present invention with an additional agent. Furthermore, resistance of cancer cells (e.g. multiple myeloma, lung cancer, etc) to therapeutic agents (e.g. dexamethasone, melphalan, erlotinib/Tarceva, imatinib, dasatinib, etc.) may be reversible upon treatment with a kinase inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one kinase inhibitor where the dexamethasone, or other therapeutic, is administered intermittently as opposed to continuously.

In some further embodiments, combinations of one or more kinase inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Pub. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating a kinase in tissue samples, including human, and for identifying kinase ligands by inhibition of binding of a labeled compound. Accordingly, the present invention includes kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$ $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro metalloprotease labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a kinase by monitoring its concentration variation when contacting with the kinase, through tracking of the labeling. For example, a test compound (labeled) can be evaluated for its ability to reduce binding of another compound which is known to bind to a kinase (i.e., standard compound). Accordingly, the ability of a test compound to compete with the standard compound for binding to the kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of kinase-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples have been found to be JAK inhibitors according to at least one assay described herein.

EXAMPLES

Example 1

N-[4-Methyl-3-(9H-pyrimido[4,5-b]indol-7-yl)phenyl]-3-(trifluoromethyl)benzamide trifluoroacetate

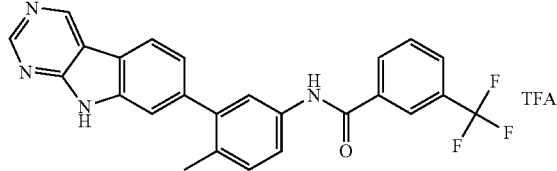 [SMILES: Cc1ccc(NC(=O)c2cccc(C(F)(F)F)c2)cc1-c1ccc2c(c1)[nH]c1ncncc12]

Step 1: N-(3-Iodo-4-methylphenyl)-3-(trifluoromethyl)benzamide

To 3-iodo-4-methylaniline (500.0 mg, 2.145 mmol) was added dichloromethane (DCM) (10 mL) followed by N,N-diisopropylethylamine (DIPEA)(520 µL, 3.0 mmol) and 3-(trifluoromethyl)-benzoyl chloride (0.36 mL, 2.4 mmol). The reaction was stirred at 25° C. for 16 hours and was transferred to a separatory funnel and partitioned between water and dichloromethane (DCM). The organic phase was sequentially washed with 0.1N HCl, saturated aqueous NaHCO$_3$, water, then saturated aqueous NaCl. The washed organic phase was then dried over MgSO$_4$ and filtered and concentrated to leave the crude product. The crude product was triturated with hexanes to leave the product as an off-white solid, (797 mg, 92%). $^1$H NMR (400 MHz, CDCl$_3$): δ 8.10 (m, 2H), 8.04 (d, 1H), 7.84 (bs, 1H), 7.81 (d, 1H), 7.63 (m, 1H), 7.58 (dd, 1H), 7.22 (d, 1H), 2.42 (s, 3H). MS (EI) m/z=274 (M+H).

Step 2: N-(6-Methyl-3'-nitrobiphenyl-3-yl)-3-(trifluoromethyl)benzamide

To N-(3-iodo-4-methylphenyl)-3-(trifluoromethyl)benzamide (400 mg, 0.99 mmol) was added (3-nitrophenyl)boronic acid (180 mg, 1.1 mmol) followed by toluene (8.2 mL), ethanol (1.1 mL), and K$_2$CO$_3$ (270 mg, 2.0 mmol in 1.1 mL water). The resulting mixture was degassed with N$_2$, then tetrakis(triphenylphosphine)palladium(0) (60 mg, 0.05 mmol) was added. The mixture was degassed again, then heated under reflux condenser and N$_2$ atmosphere at 90° C. until LCMS and TLC indicated complete reaction, typically 16 hours. The reaction was then cooled to ambient temperature and transferred to a separatory funnel and partitioned between water and EtOAc. The phases were separated and the organic phase was washed with water, then saturated aqueous NaCl. The washed organic phase was then dried (MgSO$_4$) and evaporated to dryness to leave the crude product, which was purified by column chromatography to give the product (402 mg, 102%). $^1$H NMR (400 MHz, CDCl$_3$): δ 8.23 (m, 2H), 8.12 (s, 1H), 8.07 (d, 1H), 7.88 (bs, 1H), 7.82 (d, 1H), 7.6 (m, 4H), 7.32 (d, 1H), 2.27 (s, 3H). MS (EI) m/z=401 (M+H).

Step 3: N-(3'-Amino-6-methylbiphenyl-3-yl)-3-(trifluoromethyl)benzamide

To N-(6-methyl-3'-nitrobiphenyl-3-yl)-3-(trifluoromethyl)benzamide (1.00 g, 2.50 mmol) was added ethanol (18 mL) and acetic acid (1.7 mL) and iron (770 mg). The resulting mixture was heated to reflux until LCMS indicated complete reduction, typically 2-4 hours. The reaction was cooled to ambient temperature, and the unreacted iron was removed by filtration. The ethanolic filtrate was evaporated to dryness and EtOAc was added to the residue. The resulting rust-like particulates were removed by filtration through a small pad of diatomaceous earth, and the filtrate was evaporated to dryness to leave the crude aniline. The compound was recovered in quantitative yield and was used without further purification in the subsequent reaction. MS (EI) m/z=371 (M+H).

Step 4: N-3'-[(5-Iodopyrimidin-4-yl)amino]-6-methylbiphenyl-3-yl-3-(trifluoromethyl)benzamide To N-(3'-amino-6-methylbiphenyl-3-yl)-3-(trifluoromethyl)benzamide (61.0 mg, 0.135 mmol) was added 4-chloro-5-iodopyrimidine (32 mg, 0.14 mmol) and ethanol (0.4 mL). The resulting mixture was heated to 80° C. in a sealed tube until LCMS indicated complete reaction, typically 1-2 hours. The reaction was cooled to ambient temperature and the solvent was evaporated. The residue was partitioned between saturated aqueous NaHCO$_3$ and EtOAc. The organic phase was washed with brine, dried (MgSO$_4$) and evaporated to leave the crude product, which was then purified by column chromatography to give the final compound (52.9 mg, 68.2%). $^1$H NMR (300 MHz, CDCl$_3$): δ 8.61 (s, 2H), 8.10 (m, 3H), 7.80 (d, 1H), 7.71 (s, 1H), 7.4-7.7 (m, 6H), 7.29 (d, 1H), 2.29 (s, 3H). MS (EI) m/z=575 (M+H).

Step: N-[4-Methyl-3-(9H-pyrimido[4,5-b]indol-7-yl)phenyl]-3-(trifluoromethyl)benzamide trifluoroacetate To [N-3'-[(5-iodopyrimidin-4-yl)amino]-6-methylbiphenyl-3-yl-3-(trifluoromethyl)benzamide (1.85 g, 3.22 mmol) was added tri-o-tolylphosphine (200 mg, 0.64 mmol), and sodium acetate (400 mg, 4.8 mmol) followed by DMF (36 mL). The reaction was degassed with N$_2$, then palladium acetate (68 mg, 0.30 mmol) was added. The reaction was degassed again, then heated to reflux under N$_2$ until LCMS indicated complete reaction, typically 16 hours. The reaction was cooled to ambient temperature and partitioned between water and EtOAc. The organic phase was washed with water and saturated aqueous NaCl, then dried (MgSO$_4$) and filtered and concentrated to dryness to leave the crude product. The tan solid was triturated successively with ether and 1:1 ether:CH$_2$Cl$_2$ to give the desired product (800 mg, 60%). A portion of this material was further purified by preparative LCMS, and upon lyophilization the product was recovered as a TFA salt. $^1$H NMR (300 MHz, DMSO, TFA salt): δ 13.0 (bs, 1H), 10.5 (s, 1H), 9.64 (s, 1H), 9.13 (s, 1H), 8.38 (d, 1H), 8.29 (s, 1H), 8.26 (d, 1H), 7.96 (d, 1H), 7.7-7.8 (m, 3H), 7.56 (s, 1H), 7.43 (dd, 1H), 7.34 (d, 1H), 2.26 (s, 3H). MS (EI) m/z=447 (M+H).

Example 2

3-(4-Methyl-1H-imidazol-1-yl)-N-[4-methyl-3-(9H-pyrimido[4,5-b]indol-7-yl)-phenyl]-5-(trifluoromethyl)benzamide bis(trifluoroacetate)

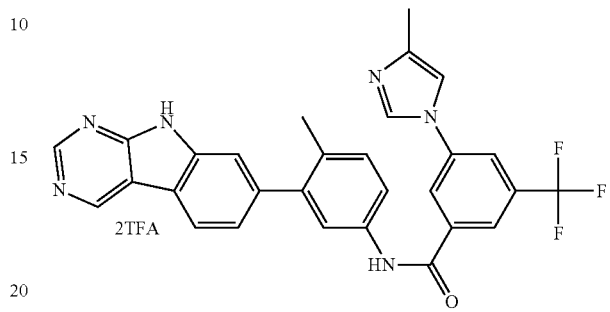

Step 1:
4-Methyl-3-(9H-pyrimido[4,5-b]indol-7-yl)aniline

To N-[4-methyl-3-(9H-pyrimido[4,5-b]indol-7-yl)phenyl]-3-(trifluoromethyl)benzamide (442 mg, 0.990 mmol) was added 1,4-dioxane (2.0 mL) and water (2.0 mL) and sodium hydroxide (790 mg, 19.8 mmol). The resulting mixture was heated to 100° C. until LCMS indicated complete hydrolysis, typically 14-16 hours. The reaction was cooled to ambient temperature and the solvents were removed by evaporation. The residue was washed with water and the remaining solid was recovered by filtration, washed with additional water, and dried under reduced pressure to give the product (207 mg, 76%). $^1$H NMR (300 MHz, DMSO): δ 9.42 (s, 1H), 8.90 (s, 1H), 8.22 (d, 1H), 7.39 (s, 1H), 7.23 (d, 1H), 6.94 (d, 1H), 6.52 (m, 2H), 4.95 (s, 2H), 2.08 (s, 3H). MS (EI) m/z=275 (M+H).

Step 2: 3-(4-Methyl-1H-imidazol-1-yl)-N-[4-methyl-3-(9H-pyrimido[4,5-b]indol-7-yl)phenyl]-5-(trifluoromethyl)benzamide bis(trifluoroacetate)

To 3-(4-methyl-1H-imidazol-1-yl)-5-(trifluoromethyl) benzoic acid (39 mg, 0.14 mmol, prepared according to WO2004005281) was added DMF (0.93 mL) followed by N,N,N',N'-tetramethyl-O-(7-azabenzotriazol-1-yl)uronium hexafluorophosphate (66.5 mg, 0.175 mmol) and N,N-diisopropylethylamine (DIPEA) (30.5 μL, 0.175 mmol). This solution was stirred at ambient temperature for 15 minutes, then 4-methyl-3-(9H-pyrimido[4,5-b]indol-7-yl)aniline (40.0 mg, 0.146 mmol) was added. The reaction was held at ambient temperature until LCMS indicated complete reaction, typically 1-2 hours. The reaction was partitioned between water and EtOAc and the organic phase was washed with water and saturated aqueous NaCl, then dried (MgSO$_4$) and evaporated to dryness to leave the crude product. This was purified by preparative LCMS to recover the product as a bis-TFA salt (60.3 mg, 55%). $^1$H NMR (400 MHz, DMSO): δ 13.0 (bs, 1H), 10.67 (s, 1H), 9.63 (s, 1H), 9.60 (s, 1H), 9.12 (s, 1H), 8.60 (s, 1H), 8.42 (m, 2H), 8.37 (d, 1H), 8.15 (s, 1H), 7.77 (m, 2H), 7.56 (s, 1H), 7.43 (dd, 1H), 7.37 (d, 1H), 2.33 (s, 3H), 2.26 (s, 3H). MS (EI) m/z=527 (M+H).

Example 19

3-Fluoro-N-[4-methyl-3-(9H-pyrimido[4,5-b]indol-7-yl)phenyl]-5-(trifluoro-methyl)benzamide

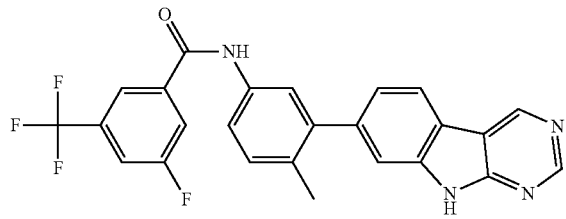 [SMILES: Cc1ccc(NC(=O)c2cc(F)cc(C(F)(F)F)c2)cc1-c1ccc2c(c1)[nH]c1ncncc12]

Step 1: 3-Fluoro-N-(3-iodo-4-methylphenyl)-5-(trifluoromethyl)benzamide

3-Iodo-4-methylaniline (2.42 g, 10.4 mmol) was dissolved in DCM (20.00 mL) and triethylamine (TEA) (1.70 mL, 12.2 mmol) was added and the resulting mixture was cooled to 0° C. To the mixture was added dropwise 3-fluoro-5-(trifluoromethyl)benzoyl chloride (1.60 mL, 10.5 mmol) and the resulting mixture was stirred at 0° C. for 45 minutes and at 25° C. for 16 hours. The reaction was extracted with ethyl acetate and the organic extracts were washed with water sat. $Na_2CO_3$, saturated NaCl, dried ($MgSO_4$) and concentrated in vacuo. The reaction product was used in the next reaction without purification. $^1$H NMR ($CDCl_3$): δ 8.98 (d, 1H), 7.78 (s, 1H), 7.72 (m, 2H), 7.55 (m, 2H), 7.23 (d, 1H), 2.42 (s, 3H). MS (EI) m/z=424 (M+H).

Step 2: 3-Fluoro-N-(6-methyl-3'-nitrobiphenyl-3-yl)-5-(trifluoromethyl)benzamide (3-Nitrophenyl)boronic acid (1.7 g, 10.0 mmol) was mixed with 3-fluoro-N-(3-iodo-4-methylphenyl)-5-(trifluoromethyl)benzamide (4.30 g, 10.2 mmol) and potassium carbonate (2.5 g, 18 mmol) in toluene (75.00 mL), ethanol (11.00 mL) and water (10.00 mL) and was degassed. To the mixture was added tetrakis(triphenylphosphine)palladium(0) (0.50 g, 0.43 mmol) and the resulting mixture was heated to reflux for 18 hours. The reaction was extracted with ethyl acetate and the organic extracts were washed with water, saturated NaCl, dried ($MgSO_4$) and then concentrated in vacuo. The residue was purified by column chromatography using 20% EtOAc/hexanes to give the product (4.09 g, 96% yield). MS (EI) m/z=419 (M+H).

Step 3: N-(3'-Amino-6-methylbiphenyl-3-yl)-3-fluoro-5-(trifluoromethyl)benzamide To 3-fluoro-N-(6-methyl-3'-nitrobiphenyl-3-yl)-5-(trifluoromethyl)benzamide (4.09 g, 9.78 mmol) was added ethanol (93.2 mL) followed by iron (3.0 g, 54 mmol) and acetic acid (9.32 mL, 164 mmol). The solution was heated at 92° C. for 2 h using the rotovap motor/heating bath. To the reaction mixture was added EtOAc and the mixture was then filtered and was concentrated in vacuo. The residue was used in the next reaction without purification. MS (EI) m/z=389 (M+H).

Step 4: 3-Fluoro-N-3'-[(5-iodopyrimidin-4-yl)amino]-6-methylbiphenyl-3-yl-5-(trifluoromethyl)-benzamide N-(3'-Amino-6-methylbiphenyl-3-yl)-3-fluoro-5-(trifluoromethyl)benzamide (3.80 g, 9.78 mmol) was mixed with 4-chloro-5-iodopyrimidine (2.35 g, 9.78 mmol) in ethanol (54.4 mL) and was heated to reflux for 2 hours. To the reaction was added sat. $Na_2CO_3$ solution and the resulting mixture was extracted with ethyl acetate. The organic extracts were washed with water, saturated NaCl, dried ($MgSO_4$) and concentrated in vacuo. The concentrate was chromatographed on silica gel using 30% EtOAc/hexanes to give the product 4.31 g, 74% yield. $^1$H NMR ($CDCl_3$): δ 8.46 (s, 1H), 8.57 (s, 1H), 7.90 (brs, 1H), 7.81 (m, 2H), 7.60 (m, 1H), 7.56 (m, 2H), 7.51 (m, 2H), 7.44 (t, 1H), 7.30 (d, 1H), 7.15 (m, 2H), 2.31 (s, 3H). MS (EI) m/z=593 (M+H).

Step 5: 3-Fluoro-N-[4-methyl-3-(9H-pyrimido[4,5-b]indol-7-yl)phenyl]-5-(trifluoromethyl)benzamide 3-Fluoro-N-3'-[(5-iodopyrimidin-4-yl)amino]-6-methylbiphenyl-3-yl-5-(trifluoromethyl)-benzamide (4.30 g, 7.26 mmol) was mixed with palladium acetate (0.16 g, 0.72 mmol), tri-o-tolylphosphine (0.44 g, 1.4 mmol) and sodium acetate in dimethylformamide (DMF) (42.0 mL) and was degassed and stirred for 5 minutes. The reaction was heated at 147° C. (oil bath temperature) for 16 hours and at 160° C. (oil bath temperature) for 8 hours at which time LCMS analysis showed no starting material present. The reaction was concentrated to a minimum volume (~2 mL) and the concentrate was triturated and was washed with ether to give the product 1.70 g, 50%. $^1$H NMR (DMSO-$d_6$): δ 12.40 (s, 1H), 10.52 (s, 1H), 9.47 (s, 1H), 8.93 (s, 1H), 8.30 (d, 1H), 8.29 (s, 1H), 8.00 (m, 1H), 7.95 (m, 1H), 7.73 (m, 2H), 7.48 (d, 1H), 7.34 (m, 2H), 2.26 (s, 3H). MS (EI) m/z=465 (M+H).

Example 20

3-(4-Formyl-1H-imidazol-1-yl)-N-[4-methyl-3-(9H-pyrimido[4,5-b]indol-7-yl)-phenyl]-5-(trifluoromethyl)benzamide trifluoroacetate

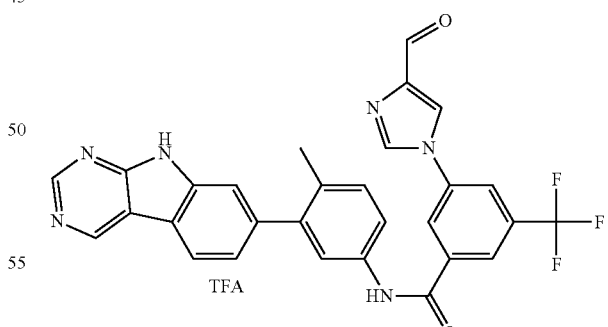

3-Fluoro-N-[4-methyl-3-(9H-pyrimido[4,5-b]indol-7-yl) phenyl]-5-(trifluoromethyl)-benzamide (0.030 g, 0.064 mmol) was mixed with 1H-imidazole-4-carbaldehyde (0.031 g, 0.32 mmol) and potassium carbonate (0.045 g, 0.32 mol) in DMF (0.7 mL) and was heated at 120° C. for 16 hours. The reaction was then diluted with THF and was filtered and the filtrate was concentrated in vacuo. The residue was purified by prep. LC to give the product (14 mg, 33% yield). $^1$H NMR (DMSO-d$_6$): δ 13.13 (brs, 1H), 10.57 (s, 1H), 9.84 (s, 1H), 9.67 (s, 1H), 9.16 (s, 1H), 8.88 (d, 1H), 8.71 (d, 1H), 8.62 (m, 1H), 8.44 (m, 1H), 8.40 (d, 1H), 8.29 (m, 1H), 7.75 (m, 2H), 7.58 (s, 1H), 7.47 (m, 1H), 7.39 (m, 1H), 2.27 (s, 3H). MS (EI) m/z=541 (M+H).

Example 21

3-[4-(Hydroxymethyl)-1H-imidazol-1-yl]-N-[4-methyl-3-(9H-pyrimido[4,5-b]indol-7-yl)phenyl]-5-(trifluoromethyl)benzamide bis(trifluoroacetate) (salt)

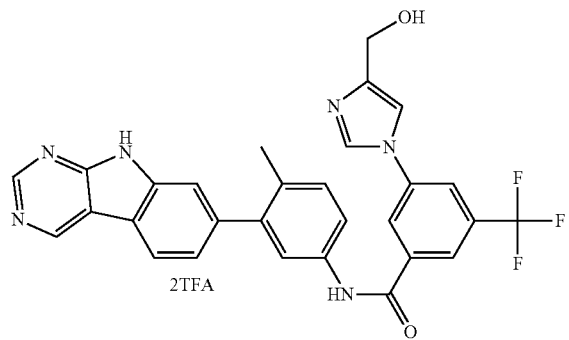 [SMILES: Cc1ccc(NC(=O)c2cc(-n3cnc(CO)c3)cc(C(F)(F)F)c2)cc1-c1ccc2c(c1)[nH]c1ncncc12]

3-(4-Formyl-1H-imidazol-1-yl)-N-[4-methyl-3-(9H-pyrimido[4,5-b]indol-7-yl)phenyl]-5-(trifluoromethyl)benzamide (20.00 mg, 0.037 mmol) was dissolved in methanol (1.00 mL) and was cooled at 0° C. To the reaction was added sodium tetrahydroborate (4.0 mg, 0.00010 mol) and the resulting mixture was stirred at 0° C. for 30 minutes and at 25° C. for 1 hour. The reaction mixture was concentrated in vacuo and was purified by prep. LC to give the product (6.8 mg, 24% yield). $^1$H NMR (DMSO-d$_6$): δ 12.84 (brs, 1H), 10.60 (s, 1H), 9.59 (s, 1H), 9.27 (brs, 1H), 9.07 (s, 1H), 8.57 (s, 1H), 8.40 (s, 1H), 8.36 (m, 2H), 8.15 (s, 1H), 7.76 (m, 2H), 7.54 (s, 1H), 7.42 (m, 2H), 4.52 (s, 2H), 2.27 (s, 3H). MS (EI) m/z=543 (M+H).

Example 22

3-4-[(Methylamino)methyl]-1H-imidazol-1-yl-N-[4-methyl-3-(9H-pyrimido[4,5-b]-indol-7-yl)phenyl]-5-(trifluoromethyl)benzamide tris(trifluoroacetate)

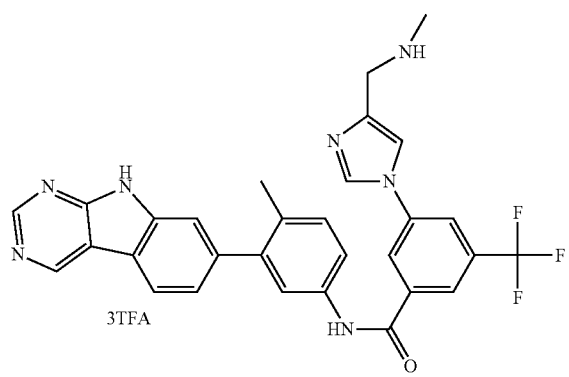 [SMILES: CNCc1cn(-c2cc(C(=O)Nc3ccc(C)c(-c4ccc5c(c4)[nH]c4ncncc45)c3)cc(C(F)(F)F)c2)cn1]

Sodium cyanoborohydride (7.0 mg, 0.11 mmol) was mixed with zinc dichloride (15 mg, 0.11 mmol) and the mixture was stirred for 5 minutes. To the mixture was added 3-(4-formyl-1H-imidazol-1-yl)-N-[4-methyl-3-(9H-pyrimido[4,5-b]indol-7-yl)phenyl]-5-(trifluoromethyl)benzamide (20.00 mg, 0.037 mmol) with methylammonium chloride (9.99 mg, 0.148 mmol) and the mixture was heated to 75° C. for 6 hours in a sealed vial. The reaction was then concentrated in vacuo and the product was purified by prep. LC (twice) (4 mg, 12% yield). $^1$H NMR (DMSO-d$_6$): δ 12.80 (brs, 1H), 10.57 (s, 1H), 9.58 (s, 1H), 9.06 (d, 1H), 8.82 (brs, 2H), 8.62 9d, 1H), 8.48 s, 1H), 8.35 (m, 2H), 8.29 (s, 2H), 8.08 (s, 1H), 7.75 (m, 2H), 7.54 (s, 1H), 7.39 (m, 2H), 4.10 m, 2H), 2.58 (m, 3H), 2.27 (s, 3H). MS (EI) m/z=556 (M+H).

Example 26

3-(4-Methylpiperazin-1-yl)-N-[4-methyl-3-(9H-pyrimido[4,5-b]indol-7-yl)phenyl]-5-(trifluoromethyl)benzamide bis(trifluoroacetate)

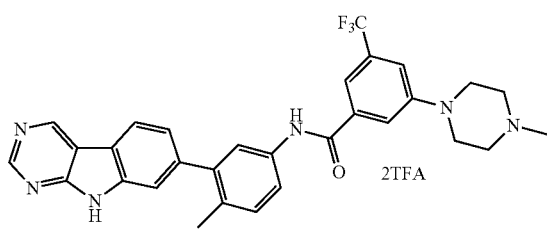 [SMILES: Cc1ccc(NC(=O)c2cc(N3CCN(C)CC3)cc(C(F)(F)F)c2)cc1-c1ccc2c(c1)[nH]c1ncncc12]

To 3-fluoro-N-[4-methyl-3-(9H-pyrimido[4,5-b]indol-7-yl)phenyl]-5-(trifluoromethyl)-benzamide (20.0 mg, 0.0431 mmol) was added 1-methylpiperazine (300.0 uL, 2.705 mmol) and potassium carbonate (7.1 mg, 0.052 mmol). The resulting mixture was sealed and heated to 140° C. for 48 hours. The reaction was allowed to cool, then diluted with THF and MeOH, and purified by pH 2 prep LCMS to recover the product as a bis-TFA salt (20.5 mg, 62% yield). $^1$H NMR (DMSO-d$_6$): 12.8 (brs, 1H), 10.40 (s, 1H), 9.81 (brs, 1H), 9.58 (s, 1H), 9.06 (s, 1H), 8.34 (d, 1H), 7.74 (m, 4H), 7.51 (d, 2H), 7.37 (dd, 2H), 4.10 (m, 2H), 3.53 (m, 2H), 3.12 (m, 4H), 2.86 (s, 3H), 2.25 (s, 3H). MS (EI) m/z=545 (M+H).

Example 40

N-[4-Methyl-3-(9H-pyrimido[4,5-b]indol-6-yl)phenyl]-3-(trifluoromethyl)benzamide

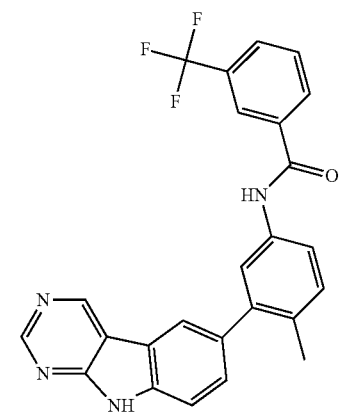 [SMILES: Cc1ccc(NC(=O)c2cccc(C(F)(F)F)c2)cc1-c1ccc2[nH]c3ncncc3c2c1]

Step 1: N-(6-Methyl-4'-nitrobiphenyl-3-yl)-3-(trifluoromethyl)benzamide

To N-(3-iodo-4-methylphenyl)-3-(trifluoromethyl)benzamide (400.0 mg, 0.99 mmol) was added 4,4,5,5-tetramethyl-2-(4-nitrophenyl)-1,3,2-dioxaborolane (270 mg, 1.1 mmol) followed by toluene (8.2 mL), then ethanol (1.15 mL), and K₂CO₃ (270 mg, 2.0 mmol in 1.1 mL water). The reaction was degassed with N₂, then tetrakis(triphenylphosphine)palladium(0) (60 mg, 0.05 mmol) was added. The reaction was degassed again, and then heated at reflux under N₂ atmosphere at 90° C. until LCMS and TLC indicated complete reaction, about 16 hours. The reaction was then cooled to ambient temperature, transferred to a separatory funnel and partitioned between water and EtOAc. The phases were separated and the organic phase was washed with water, then saturated aqueous NaCl, dried (MgSO₄) and then evaporated to dryness to leave the crude product, which was purified by column chromatography to give the product (379 mg, 95.79%). $^1$H NMR (400 MHz, CDCl₃): δ 8.29 (m, 2H), 8.12 (s, 1H), 8.07 (d, 1H), 7.82 (m, 2H), 7.5-7.7 (m, 5H), 7.33 (d, 1H), 2.26 (s, 3H). MS (EI) m/z=401 (M+H).

Step 2: N-(4'-Amino-6-methylbiphenyl-3-yl)-3-(trifluoromethyl)benzamide

To N-(6-methyl-4'-nitrobiphenyl-3-yl)-3-(trifluoromethyl)benzamide (375 mg, 0.937 mmol) was added 1,4-dioxane (12 mL) and water (6.2 mL), then ammonium hydroxide (220 μL, 5.6 mmol) followed by sodium dithionite (1.4 g, 7.9 mmol). The reaction was stirred at ambient temperature until LCMS indicated complete reduction, typically 30-60 minutes. The reaction is accompanied by a color change from yellow to colorless. The reaction was partitioned between water and EtOAc and the organic phase was washed with water and saturated aqueous NaCl, then dried (MgSO₄) and evaporated to leave the crude product (155 mg, 44.8%) which was used without further purification in the subsequent reaction. MS (EI) m/z=371 (M+H).

Step 3: N-4'-[(5-Iodopyrimidin-4-yl)amino]-6-methylbiphenyl-3-yl-3-(trifluoromethyl)benzamide To N-(4'-amino-6-methylbiphenyl-3-yl)-3-(trifluoromethyl)benzamide (60.0 mg, 0.162 mmol) was added 4-chloro-5-iodopyrimidine (39 mg, 0.16 mmol) followed by ethanol (0.47 mL). The reaction was heated to 80° C. in a sealed tube until LCMS indicated complete reaction, typically 1-2 hours. The reaction was cooled to ambient temperature and the solvent was evaporated. The residue was partitioned between saturated aqueous NaHCO₃ and EtOAc, the organic phase was washed with brine, dried (MgSO₄) and evaporated to leave the crude product, which was then purified by column chromatography to give the final compound (39.9 mg, 42.88%). $^1$H NMR (400 MHz, CDCl₃): δ 8.61 (s, 2H), 8.14 (s, 1H), 8.08 (d, 1H), 7.95 (s, 1H), 7.81 (d, 1H), 7.5-7.7 (m, 5H), 7.40 (m, 3H), 7.29 (d, 1H), 2.29 (s, 3H). MS (EI) m/z=575 (M+H).

Step 4: N-[4-Methyl-3-(9H-pyrimido[4,5-b]indol-6-yl)phenyl]-3-(trifluoromethyl)benzamide To N-4'-[(5-iodopyrimidin-4-yl)amino]-6-methylbiphenyl-3-yl-3-(trifluoromethyl)benzamide (35.0 mg, 0.061 mmol) was added tri-o-tolylphosphine (7.0 mg, 0.02 mmol), and sodium acetate (7.5 mg, 0.091 mmol) followed by DMF (0.42 mL). The reaction was degassed with N₂, then palladium acetate (3.0 mg, 0.01 mmol) was added. The reaction was degassed again, then heated to reflux under N₂ until LCMS indicated complete reaction, typically 16 hours. The reaction was cooled to ambient temperature and partitioned between water and EtOAc. The organic phase was washed with water and saturated aqueous NaCl, dried (MgSO₄) and filtered and the filtrate was concentrated to dryness to leave the crude product. The product was purified by reverse phase preparative LCMS to recover the product as a free base (2.50 mg, 9.2%). $^1$H NMR (500 MHz, CD₃OD): δ 9.36 (s, 1H), 8.90 (s, 1H), 8.26 (s, 1H), 8.21 (m, 2H), 7.87 (d, 1H), 7.5-7.8 (m, 5H), 7.33 (d, 1H), 2.30 (s, 3H). MS (EI) m/z=447 (M+H).

Example 41

4-Fluoro-N-[4-methyl-3-(9H-pyrimido[4,5-b]indol-6-yl)phenyl]-3-(trifluoromethyl)benzamide

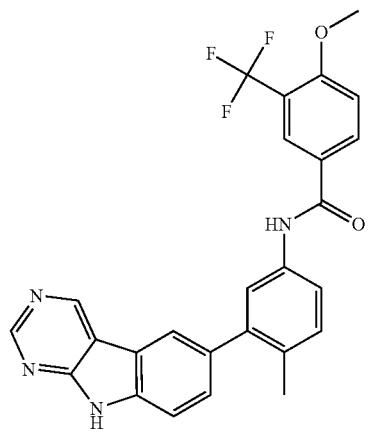 [SMILES: COc1ccc(C(=O)Nc2ccc(C)c(-c3ccc4[nH]c5ncncc5c4c3)c2)cc1C(F)(F)F]

Step 1: 4-Methyl-3-(9H-pyrimido[4,5-b]indol-6-yl)aniline

To 3-fluoro-N-[4-methyl-3-(9H-pyrimido[4,5-b]indol-6-yl)phenyl]benzamide (205 mg, 0.517 mmol) was added 1,4-dioxane (3.1 mL) and aqueous sodium hydroxide (3.8M, 2.72 mL, 10.0 mmol) followed by solid sodium hydroxide (1.67 g, 41.7 mmol). The reaction was heated to 100° C. until LCMS indicated complete hydrolysis, typically 16-24 hours. The reaction was cooled to ambient temperature and partitioned between water and EtOAc, which resulted in the formation of solids. These solids were dissolved through successive extractions with EtOAc and 3:1 CHCl₃:IPA. The organic phases were separately washed with water and saturated aqueous NaCl, then dried (MgSO₄), the dried solutions were combined and evaporated to dryness to leave the crude product (133 mg, 93.8%). $^1$H NMR (300 MHz, DMSO): δ 12.33 (bs, 1H), 9.46 (s, 1H), 8.91 (s, 1H), 8.16 (s, 1H), 7.57 (d, 1H), 7.44 (dd, 1H), 6.94 (d, 1H), 6.4-6.6 (m, 2H), 5.00 bs, 2H), 2.08 (s, 3H). MS (EI) m/z=275 (M+H).

Step 2: 4-Methoxy-N-[4-methyl-3-(9H-pyrimido[4,5-b]indol-6-yl)phenyl]-3-(trifluoromethyl)-benzamide To 4-methoxy-3-(trifluoromethyl)benzoyl chloride (11.0 μL, 0.070 mmol) was added a solution of 4-methyl-3-(9H-pyrimido[4,5-b]indol-6-yl)aniline (17.5 mg, 0.064 mmol)

and DIPEA (16 μL, 0.089 mmol) in tetrahydrofuran (THF) (0.4 mL). The reaction was stirred at ambient temperature until LCMS indicated complete reaction, typically 16 hours. The reaction mixture was diluted to a total of 2 mL with THF and MeOH and purified by preparative LCMS to recover the product as a TFA salt (18.6 mg, 49.4%). $^1$H NMR (300 MHz, DMSO): δ 13.0 (bs, 1H), 10.33 (s, 1H), 9.64 (s, 1H), 9.13 (s, 1H), 8.35 (s, 1H), 8.24 (m, 2H), 7.7-7.8 (m, 3H), 7.63 (dd, 1H), 7.41 (d, 1H), 7.32 (d, 1H), 2.25 (s, 3H). MS (EI) m/z=477 (M+H).

Example 47

N-[4-Methyl-3-(9H-pyrimido[4,5-b]indol-7-yl)phenyl]-N'-[3-(trifluoromethyl)-phenyl]urea

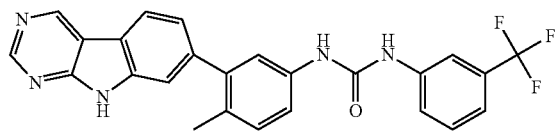 [SMILES: Cc1ccc(NC(=O)Nc2cccc(C(F)(F)F)c2)cc1-c1ccc2c(c1)[nH]c1ncncc12]

To 1-isocyanato-3-(trifluoromethyl)benzene (8.7 μl, 0.062 mmol) was added a solution of 4-methyl-3-(9H-pyrimido[4,5-b]indol-7-yl)aniline (17.0 mg, 0.062 mmol) and DIPEA (16 μL, 0.089 mmol) in THF (0.4 mL). The reaction was stirred at ambient temperature until LCMS indicated complete reaction, typically 3-4 hours. The reaction mixture was diluted to a total of 2 mL with THF and MeOH and purified by preparative LCMS to recover the product as a TFA salt (16.7 mg, 46.9%). $^1$H NMR (400 MHz, CDCl$_3$): δ 13.0 (bs, 1H), 9.65 (s, 1H), 9.15 (s, 2H), 8.93 (s, 1H), 8.37 (d, 1H), 8.01 (s, 1H), 7.4-7.6 (m, 5H), 7.2-7.4 (m, 3H), 2.21 (s, 3H). MS (EI) m/z=462 (M+H).

Example 48

N-[4-Methyl-3-(9H-pyrimido[4,5-b]indol-6-yl)phenyl]-N'-[3-(trifluoromethyl)-phenyl]urea

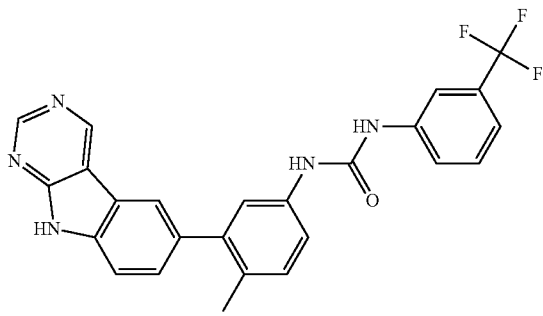 [SMILES: Cc1ccc(NC(=O)Nc2cccc(C(F)(F)F)c2)cc1-c1ccc2[nH]c3ncncc3c2c1]

To 1-isocyanato-3-(trifluoromethyl)benzene (9.8 μl, 0.070 mmol) was added a solution of 4-methyl-3-(9H-pyrimido[4,5-b]indol-6-yl)aniline (17.5 mg, 0.064 mmol) and DIPEA (16 μL, 0.089 mmol) in THF (0.4 mL). The reaction was stirred at ambient temperature until LCMS indicated complete reaction, typically 16 hours. The reaction mixture was diluted to a total of 2 mL with THF and MeOH and purified by preparative LCMS to recover the product as a TFA salt (17.1 mg, 46.6%). $^1$H NMR (300 MHz, DMSO): δ 13.1 (bs, 1H), 9.66 (s, 1H), 9.15 (s, 2H), 8.92 (s, 1H), 8.33 (s, 1H), 8.01 (s, 1H), 7.72 (d, 1H), 7.62 (dd, 1H), 7.4-7.6 (m, 3H), 7.2-7.4 (m, 3H), 2.21 (s, 3H). MS (EI) m/z=462 (M+H).

Example 49

4-Methyl-3-(9H-pyrimido[4,5-b]indol-6-yl)-N-[3-(trifluoromethyl)phenyl]-benzamide

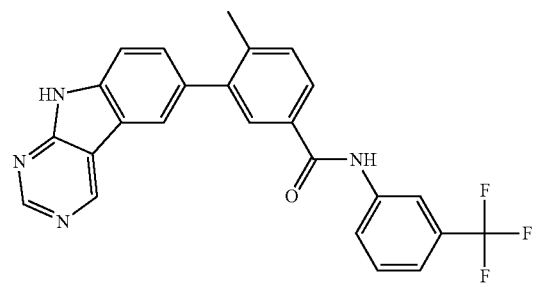 [SMILES: Cc1ccc(C(=O)Nc2cccc(C(F)(F)F)c2)cc1-c1ccc2[nH]c3ncncc3c2c1]

Step 1: 6-Methyl-4'-nitro-N-[3-(trifluoromethyl)phenyl]biphenyl-3-carboxamide 4,4,5,5-Tetramethyl-2-(4-nitrophenyl)-1,3,2-dioxaborolane (0.35 g, 0.0014 mol) was mixed with 3-iodo-4-methyl-N-[3-(trifluoromethyl)phenyl]benzamide (0.73 g, 0.0018 mol) and potassium carbonate (0.50 g, 0.0036 mol) in toluene (15.00 mL), ethanol (2.10 mL) and water (2.00 mL) and the mixture was degassed. To the reaction was added tetrakis(triphenylphosphine)palladium(0) (0.10 g, 0.000086 mol) and the mixture was heated to reflux for 8 hours. The reaction was extracted with ethyl acetate and the organic extracts were washed with water, saturated NaCl, dried (MgSO$_4$) and concentrated in vacuo. The concentrate was chromatographed on silica gel using 30% EtOAc/hexanes to give the product (0.32 g, 57% yield). $^1$H NMR (CDCl$_3$): δ 8.33 (dd, 2H), 7.76-7.93 (m, 5H), 7.43-7.54 (m, 5H), 2.35 (s, 3H). MS (EI) m/z=401 (M+H).

Step 2: 4'-Amino-6-methyl-N-[3-(trifluoromethyl)phenyl]biphenyl-3-carboxamide

6-Methyl-4'-nitro-N-[3-(trifluoromethyl)phenyl]biphenyl-3-carboxamide was dissolved in 1,4-dioxane (10.00 mL, 0.1281 mol) and water (5.00 mL, 0.278 mol), and ammonium hydroxide (0.18 mL, 0.0045 mol) was added. To the reaction was added sodium dithionite (1.10 g, 0.00632 mol) and this mixture was stirred at 25° C. for 2 hours at which time HPLC analysis showed aniline formation. The reaction was extracted with ethyl acetate and the organic extracts were washed with water, saturated NaCl, dried (MgSO$_4$) and concentrated in vacuo. MS (EI) m/z=371 (M+H).

Step 3: 4'-[(5-Iodopyrimidin-4-yl)amino]-6-methyl-N-[3-(trifluoromethyl)phenyl]biphenyl-3-carboxamide 4'-Amino-6-methyl-N-[3-(trifluoromethyl)phenyl]biphenyl-3-carboxamide (0.26 g, 0.00070 mol) was mixed with 4-chloro-5-iodopyrimidine (0.17 g, 0.00070 mol) in ethanol (3.00 mL, 0.0514 mol) and the mixture was heated to reflux for 2 hours at which time LCMS analysis showed mainly product. To the reaction was added sat. Na$_2$CO$_3$ solution and the mixture was extracted with ethyl acetate. The organic extracts were washed with water, saturated NaCl, dried (MgSO$_4$) and concentrated in vacuo. The concentrate was chromatographed on silica gel using 30% EtOAc/hexanes to give the product (178 mg, 44% yield). $^1$H NMR (CDCl$_3$): δ 8.66 (s, 1H), 8.62 (s, 1H), 7.96 (m, 2H), 7.70-7.89 (m, 5H), 7.37-7.50 (m, 5H), 7.20 (s, 1H), 2.38 (s, 3H). MS (EI) m/z=575 (M+H).

Step 4: 4-Methyl-3-(9H-pyrimido[4,5-b]indol-6-yl)-N-[3-(trifluoromethyl)phenyl]benzamide 4'-[(5-Iodopyrimidin-4-yl)amino]-6-methyl-N-[3-(trifluoromethyl)phenyl]biphenyl-3-carboxamide (0.168 g, 0.000292 mol) was mixed with palladium acetate (0.013 g, 0.000058 mol), tri-o-tolylphosphine (0.036 g, 0.00012 mol) and sodium acetate (0.036 g, 0.00044 mol) in DMF (2.0 mL, 0.026 mol) and the mixture was heated to reflux for 4 hours. Mass spectral analysis showed ~60% conversion. The reaction was continued for 2.5 hours at which time LCMS analysis showed ~75% conversion. The reaction was extracted with ethyl acetate and the organic extracts were washed with water, saturated NaCl, dried (MgSO$_4$) and concentrated in vacuo. The concentrate was chromatographed on silica gel using 2:1 EtOAc/hexanes to give the product (75 mg, 57% yield). $^1$H NMR (CDCl$_3$): δ 9.23 (s, 1H), 9.10 (brs, 1H), 9.06 (s, 1H), 8.08 (s, 1H), 7.80-8.00 (m, 5H), 7.39-7.84 (m, 5H), 2.39 (s, 3H). MS (EI) m/z=447 (M+H).

Example 50

4-Chloro-3-(9H-pyrimido[4,5-b]indol-7-yl)-N-[3-(trifluoromethyl)phenyl]-benzamide

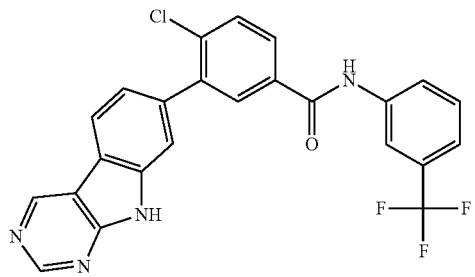 [SMILES: O=C(Nc1cccc(C(F)(F)F)c1)c1ccc(Cl)c(-c2ccc3c(c2)[nH]c2ncncc23)c1]

Step 1: 4-Chloro-3-iodo-N-[3-(trifluoromethyl)phenyl]benzamide

4-Chloro-3-iodobenzoic acid (1.00 g, 0.00354 mol) was slurried in DCM (9 mL) and was cooled at 0° C. To the mixture was added DMF (27 μL, 0.00035 mol) followed by oxalyl chloride (0.449 mL, 0.00531 mol). The resulting mixture was stirred at 0° C. for 30 minutes and then was warmed to 20° C. and was stirred for 60 minutes, by which time solution had occurred. LCMS of a sample quenched in methanol showed clean formation of the methyl ester (M+H 297/299, 3:1). The reaction mixture was concentrated to remove the excess oxalyl chloride providing acid chloride as a yellow solid acid. To the product was added DCM (10 mL), 3-(trifluoromethyl)benzenamine (0.484 mL, 0.00389 mol), then DIPEA (0.925 mL, 0.00531 mol). After 16 h, LCMS showed clean conversion to the expected M+H 426/428 (3:1). The reaction was quenched into 10% citric acid, and the resulting mixture was extracted with DCM. The organic layer was washed with water, then saturated NaHCO$_3$, and dried (Na$_2$SO$_4$). To the dried organic layer was added an equal volume of hexane and this mixture was concentrated using a rotary evaporator to remove most or all of the DCM. The resulting solid was filtered, rinsed with hexane and air dried to give 1.29 g off-white solid amide.

Step 2: 6-Chloro-3'-nitro-N-[3-(trifluoromethyl)phenyl]biphenyl-3-carboxamide 4,4,5,5-Tetramethyl-2-(3-nitrophenyl)-1,3,2-dioxaborolane (0.40 g, 0.0016 mol) was mixed with 4-chloro-3-iodo-N-[3-(trifluoromethyl)phenyl]benzamide (0.600 g, 0.00141 mol), potassium carbonate (0.39 g, 0.0028 mol), toluene (10 mL), ethanol (1.7 mL), and water (1.1 mL). The mixture was degassed by bubbling nitrogen through it. To the reaction was added tetrakis(triphenyl-phosphine)palladium(0) (0.078 g, 0.000068 mol). The reaction was heated to reflux for 16 hours. LCMS showed about 80% conversion to M+H 421/423 (3:1). The reaction was extracted with ethyl acetate and the organic extracts were washed with water, saturated NaCl, then dried (Na$_2$SO$_4$). Solvent was removed under vacuum to give 0.87 g oil. The product was purified by automatic flash chromatography on silica gel. Used a 40 g column; flow 40 mL/min; [A=hexane] [B=EtOAc]. A, 4 min; Gradient to 20% B in 30 min. The product eluted in 23-28 min (starting material at 16-18 min). Removal of solvent under vacuum gave 0.46 g white solid.

Step 3: 3'-Amino-6-chloro-N-[3-(trifluoromethyl)phenyl]biphenyl-3-carboxamide

6-Chloro-3'-nitro-N-[3-(trifluoromethyl)phenyl]biphenyl-3-carboxamide (0.46 g, 0.0011 mol) was dissolved in methanol (40 mL), and palladium hydroxide on carbon (20%; 88 mg; 50% wet; 0.000063 mol) was added. The resulting mixture was hydrogenated at 60 psi and 20° C. for 20 h, at which time LCMS showed near complete conversion to the aniline (accompanied by 3% de-chlorination). The reaction mixture was filtered; and rinsed thoroughly. The filtrate was concentrated in vacuo to give 0.33 g of product. The product was purified by prep HPLC/MS using a 30 mm×100 mm C18 column; 35% CH$_3$CN—H$_2$O (0.1% TFA), 1 min, to 55% at 6 min; 60 mL/min; detector set at m/z 391; retention time, 5.5 min. The resulting mixture was freeze dried to yield 258 mg white solid TFA salt. $^1$H NMR (DMSO-d$_6$) δ 10.62 (br s, 1H, amide NH); 8.20 (s, 1H); 8.04 (d, 1H); 8.00 (m, 2H); 7.75 (d, 1H); 7.59 (t, 1H); 7.45 (d, 1H); 7.35 (t, 1H); 7.00 (m, 3H).

Step 4: 6-Chloro-3'-[(5-iodopyrimidin-4-yl)amino]-N-[3-(trifluoromethyl)phenyl]biphenyl-3-carboxamide In a screw-capped vial, 3'-amino-6-chloro-N-[3-(trifluoromethyl)phenyl]biphenyl-3-carboxamide (240 mg TFA salt, 0.476 mmol) was mixed with 4-chloro-5-iodopyrimidine (0.131 g, 0.543 mmol) and isopropyl alcohol (2.0 mL), and the mixture was heated to 80° C. After 16 h, the reaction was complete by LCMS (M+H 595/597, 3:1). To the reaction mixture was added potassium carbonate solution. The resulting mixture was extracted with ethyl acetate and the organic extracts were washed with water, and then with saturated NaCl, and then dried (Na$_2$SO$_4$) and concentrated in vacuo to provide a residue (0.3 g). TLC (30% EtOAc-hexane) Rf 0.19. The residue was purified by automatic flash chromatography on silica gel using a 12 g column; flow 30 mL/min; [A=hexane] [B=EtOAc]. A, 4 min; Gradient to 30% B in 30 min. The product eluted in 26-32 min and the fractions were concentrated to give 0.19 g of the purified product.

Step 5: 4-Chloro-3-(9H-pyrimido[4,5-b]indol-7-yl)-N-[3-(trifluoromethyl)phenyl]benzamide tri-o-Tolylphosphine (2.0E1 mg, 0.064 mmol) was stirred in DMF (2 mL). The mixture was degassed by bubbling nitrogen through it until all additions were complete. To the mixture was added palladium acetate (7.2 mg, 0.032 mmol), and the resulting mixture was stirred at 20° C. for 5 min. To the resulting mixture was added sodium acetate (39.5 mg, 0.482 mmol) and 6-chloro-3'-[(5-iodopyrimidin-4-yl)amino]-N-[3-(trifluoromethyl)phenyl]biphenyl-3-carboxamide (0.191 g, 0.321 mmol). The resulting mixture was heated to reflux. After 4 h, LCMS showed complete reaction to give the desired product, M+H 467; and small amounts of reduction product (M+H 469) and de-chlorination product (M+H 433). The product was isolated by prep HPLC using a 30 mm×100 mm C18 column; 35% CH$_3$CN—H$_2$O (0.1% TFA), 1.5 min, to 55% at 6 min; 60 mL/min; detector set at 285 nm; retention time, 4.9 min; retention time of the de-chlorination product, 4.5 min. The HPLC fractions were freeze-dried to yield product TFA salt, a white solid; $^1$H NMR (DMSO-d$_6$) δ 13.0 (s, 1H, NH); 10.7 (s, 1H, amide NH); 9.63 (s, 1H, NH); 9.11 (s, 1H); 8.44 (d, 1H); 8.36 (s, 1H); 8.27 (s, 1H); 8.09 (d, 1H); 8.02 (t, 2H); 7.95 (s, 1H); 7.84 (d, 1H); 7.70 (t, 1H); 7.62 (t, 1H); 7.47 (d, 1H).

Example 51

4-Cyano-3-(9H-pyrimido[4,5-b]indol-7-yl)-N-[3-(trifluoromethyl)phenyl]-benzamide

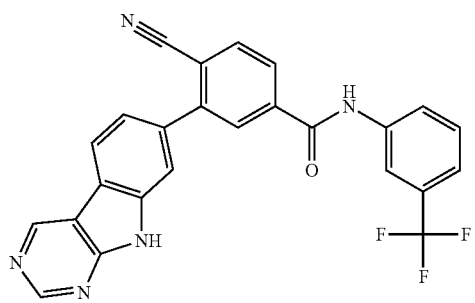 [SMILES: N#Cc1ccc(C(=O)Nc2cccc(C(F)(F)F)c2)cc1-c1ccc2c(c1)[nH]c1ncncc12]

4-Chloro-3-(9H-pyrimido[4,5-b]indol-7-yl)-N-[3-(trifluoromethyl)phenyl]benzamide (60 mg TFA salt, 0.103 mmol), zinc cyanide (121 mg, 1.03 mmol), and tetrakis(triphenylphosphine)-palladium(0) (59 mg, 0.051 mmol) were stirred in DMF (3 mL) and the mixture was flushed with nitrogen. The mixture was heated in a microwave reactor at 175° C. for 1 h. LCMS showed 65% conversion to the desired product, M+H 458. The product was isolated by prep LCMS using a 30 mm×100 mm C18 column; 35% CH$_3$CN—H$_2$O (0.1% TFA), 1 min, to 55% at 6 min; 60 mL/min; detector set at m/z 458. The HPLC fractions were rotovaped to give 23 mg of the produce as a TFA salt. The product was purified by prep HPLC using a 19 mm×100 mm C18 column; 50% CH$_3$CN—H$_2$O (0.1% AcOH), 1 min, to 75% at 6 min; 30 mL/min; detector set at 254 nm; retention time, 3.9 min. Fractions containing pure product were combined and freeze-dried. yield 4 mg. $^1$H NMR (DMSO-d$_6$) δ 12.88 (s, 1H, NH); 10.83 (s, 1H, amide NH); 9.61 (s, 1H, NH); 9.07 (s, 1H); 8.48 (d, 1H); 8.29 (d, 1H); 8.23 (s, 1H); 8.20 (d, 1H); 8.14 (dd, 1H); 8.06 (d, 1H); 7.89 (d, 1H); 7.68 (dd, 1H); 7.62 (t, 1H); 7.49 (d, 1H).

Example 66

4-Methyl-3-(9H-pyrimido[4,5-b]indol-7-yl)-N-[5-(trifluoromethyl)pyridin-3-yl]-benzamide

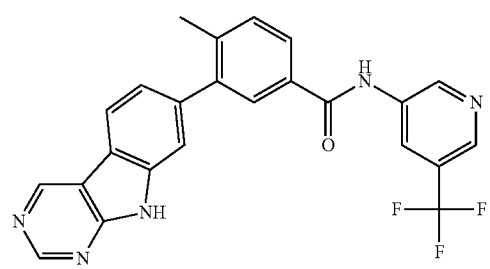 [SMILES: Cc1ccc(C(=O)Nc2cncc(C(F)(F)F)c2)cc1-c1ccc2c(c1)[nH]c1ncncc12]

Step 1: 6-Methyl-3'-nitrobiphenyl-3-carboxylic acid 4,4,5,5-Tetramethyl-2-(3-nitrophenyl)-1,3,2-dioxaborolane (5.16 g, 0.0207 mol) was mixed with 3-iodo-4-methylbenzoic acid (4.94 g, 0.0188 mol), and potassium carbonate (10.4 g, 0.0753 mol) in toluene (100 mL), 1-butanol (20 mL) and water (15 mL) and the resulting mixture was degassed by sparging nitrogen through it. To the reaction was added tetrakis(triphenylphosphine)palladium(0) (1.0 g, 0.00091 mol). The mixture was stirred rapidly and was heated to reflux for 1.5 hour. LCMS analysis showed the reaction to be complete, M+H 258. The mixture was then cooled to 20° C. The aqueous layer was discarded. To the organic layer was added saturated NaHCO$_3$. The toluene layer was extracted with aqueous sodium bicarbonate, then discarded. The aqueous sodium bicarbonate and alcohol layers were combined, then acidified to pH 2.5 with HCl. A white solid precipitated and was separated by filtration, rinsed with water, and air dried to give 4.3 g of the product. The filtrate contained only a trace of product.

Step 2: 3'-Amino-6-methylbiphenyl-3-carboxylic acid

6-Methyl-3'-nitrobiphenyl-3-carboxylic acid (4.30 g, 16.7 mmol) was dissolved in a mixture of water (12.0 mL), 1-butanol (100 mL), and potassium hydroxide (0.95 g, 14 mmol) by heating to 40° C. To this mixture was added potassium formate (14.1 g, 167 mmol) and 10% palladium on carbon (2.8 g, 50% wet, 1.34 mmol). The resulting mixture was stirred rapidly, and heated at 75° C. for 16 h, at which time LCMS showed complete conversion to the aniline (UVmax 205 & 230 nm). The mixture was filtered hot through diatomaceous earth to remove the catalyst and the filter pad was rinsed with hot BuOH. The layers were separated. The BuOH was rotovaped to give 5.0 g of a solid residue. The solid was dissolved in 50 mL of water at 20° C. (clear solution; pH 9-10). Conc. HCl was added dropwise to adjust the pH to 5.0 (used 1.45 mL). The zwitterion form of the product precipitated and was separated by filtration, then rinsed with a small amount of water; air dried, then dried under high vacuum to provide 3.1 g of the product as an off white powder. $^1$H NMR (DMSO-d$_6$) δ 7.78 (dd, 1H); 7.68 (d, 1H); 7.38 (d, 1H); 7.06 (t, 1H); 6.55 (ddd, 1H); 6.50 (t, 1H); 6.44 (dt, 1H); 2.27 (s, 3H).

Step 3: 3'-[(5-Iodopyrimidin-4-yl)amino]-6-methyl-biphenyl-3-carboxylic acid 3'-Amino-6-methylbiphenyl-3-carboxylic acid (3.00 g, 0.0132 mol) was mixed with 4-chloro-5-iodopyrimidine (3.30 g, 0.0137 mol) and isopropyl alcohol (60 mL). The resulting mixture was heated to 80° C., at which temperature solution occurred. A short time later, the product began to precipitate. After 2 h, HPLC showed 95% conversion of to product. HPLC Method: Zorbax SB C18, 5 μm, 15 cm, 35 C, flow 1.2 mL/min, 25% CH$_3$CN—H$_2$O (0.05% TFA), to 100% CH$_3$CN in 8.0 min; stop time 11 min; detector 254 & 220 nm; retention time starting material, 2.8 min (UVmax 205 & 230 nm); pyrimidine, 4.8 min (UVmax 240 & 270 nm); product, 4.9 min (UV max 204, 228, & 290 nm). The reaction was cooled to 20° C. The product was isolated by filtration, rinsed with iPrOH, then vacuum dried. Yield 5.35 g of a light tan powder. The product is believed to be the HCl salt or partial salt. $^1$H NMR (300 MHz, DMSO) δ 9.62 (br s, 1H, NH); 8.83 (s, 1H); 8.69 (s, 1H); 7.83 (dd, 1H); 7.76 (d, 1H); 7.42-7.58 (m, 4H); 7.25 (dt, 1H); 2.33 (s, 3H).

Step 4: 4-Methyl-3-(9H-pyrimido[4,5-b]indol-7-yl)benzoic acid tri-o-Tolylphosphine (18 mg, 0.060 mmol) was stirred in DMF (3 mL). The mixture was degassed by bubbling nitrogen through it until all additions were complete. To the mixture was added palladium acetate (6.8 mg, 0.030 mmol), and the resulting mixture was stirred at 20° C. for 5 min. To this mixture was added sodium acetate (37.1 mg, 0.452 mmol) and 3'-[(5-iodopyrimidin-4-yl)amino]-6-methylbiphenyl-3-carboxylic acid (0.13 g, 0.30 mmol). The resulting mixture was heated to reflux for 2 h. LCMS showed complete reaction to give the desired product, M+H 304; and a small amount of reduction product (M+H 306). The mixture was cooled to 20° C. The product was isolated by prep HPLC/MS using a 30 mm×100 mm C18 column; 25% CH$_3$CN—H$_2$O (0.1% TFA), 1.75 min, to 40% at 6 min; 60 mL/min; detector set at m/z 304; retention time, 3.2 min; reduction product, 4.3 min. The HPLC fractions were freeze dried to yield 45 mg of the TFA salt, a white solid. $^1$H NMR (d$_6$-DMSO) δ 13.0 (br s, 1H, NH); 9.6 (s, 1H); 9.1 (s, 1H); 8.3 (d, 1H); 7.8 (m, 2H); 7.5 (s, 1H); 7.4 (m, 2H); 2.3 (s, 3H).

Step 1a: 5-(Trifluoromethyl)pyridin-3-amine

2-Chloro-3-nitro-5-(trifluoromethyl)pyridine (0.850 g, 3.75 mmol) was dissolved in methanol (17 mL) and palladium on carbon (800 mg of 10%, 50% wet, 0.375 mmol) was added. The mixture was hydrogenated at 60 psi and 20° C. for 16 h. LCMS showed no remaining starting material or hydroxylamine (M+H 213/215, 3:1) intermediate, and showed a mixture of partially reduced product (M+H 163; UVmax 214, 258, & 332 nm) and the fully reduced product (M+H 169; no UV). The mixture was filtered; and the filtrate was rinsed thoroughly, and concentrated in vacuo to give 0.74 g, of the product as the HCl salt. The product was purified by prep HPLC/MS using a 30 mm×100 mm C18 column; 20% CH$_3$CN—H$_2$O (0.1% NH4OH), 1 min, to 40% at 6 min; 60 mL/min; detector set at m/z 163; retention time, 4.4 min. Fractions containing the pure product were combined and concentrated to give an oil, 52 mg, 8% yield. $^1$H NMR (CDCl$_3$) δ 8.26 (s, 1H); 8.24 (d, 1H); 7.15 (t, 1H); 4.00 (s, 2H).

Step 5: 4-Methyl-3-(9H-pyrimido[4,5-b]indol-7-yl)-N-[5-(trifluoromethyl)pyridin-3-yl]benzamide To a vial was added 4-methyl-3-(9H-pyrimido[4,5-b]indol-7-yl)benzoic acid (15.2 mg, 0.0501 mmol), DMF (0.32 mL), and N,N,N',N'-tetramethyl-O-(7-azabenzotriazol-1-yl) uronium hexafluorophosphate (22.9 mg, 0.0601 mmol). This mixture was stirred 15 min at RT. To the mixture was then added 5-(trifluoromethyl)pyridin-3-amine (10.6 mg, 0.0651 mmol). The resulting mixture was stirred at 70° C. for 18 h. LCMS indicated complete consumption of the activated ester (M+H 422) and showed product (M+H 448). The product was isolated by prep HPLC/MS using a 19 mm×100 mm C18 column; 28% CH$_3$CN—H$_2$O (0.1% TFA), 1 min, to 48% at 6 min; 30 mL/min. The HPLC fractions containing the product were freeze dried to yield a light yellow solid, 5.6 mg, 20% yield. FMR showed that it was the mono TFA salt; and contained some residual PF$_6$. $^1$H NMR (DMSO-d$_6$) δ 13.29 (s, 1H, NH); 10.76 (s, 1H, amide NH); 9.72 (s, 1H); 9.22 (s, 1H); 9.20 (s, 1H); 8.69 (s, 1H); 8.62 (s, 1H); 8.44 (d, 1H); 7.98 (m, 2H); 7.66 (s, 1H); 7.56 (d, 1H); 7.53 (d, 1H).

Example 67

N-[3-(2-Amino-9H-pyrimido[4,5-b]indol-7-yl)-4-methylphenyl]-3-(trifluoro-methyl)benzamide trifluoroacetate

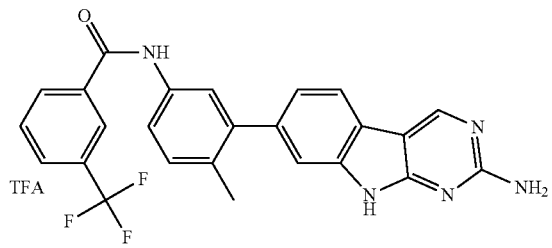 [SMILES: Cc1ccc(NC(=O)c2cccc(C(F)(F)F)c2)cc1-c1ccc2c(c1)[nH]c1nc(N)ncc12]

Step 1: N-3'-[(2-Chloro-5-iodopyrimidin-4-yl)amino]-6-methylbiphenyl-3-yl-3-(trifluoromethyl)-benzamide N-(3'-Amino-6-methylbiphenyl-3-yl)-3-(trifluoromethyl) benzamide (0.27 g, 0.73 mmol) was mixed with 2,4-dichloro-5-iodopyrimidine (0.22 g, 0.80 mmol) and sodium bicarbonate (0.067 g, 0.80 mmol) in ethanol (5.00 mL, 85.6 mmol) and the mixture was heated at 62° C. for 16 hours. The reaction was extracted with ethyl acetate and the organic extracts were washed with water, saturated NaCl, dried (MgSO$_4$) and concentrated in vacuo. The concentrate was chromatographed on silica gel using 33% EtOAc/hexanes to give the product (0.25 g, 57% yield). $^1$H NMR (CDCl$_3$): δ 8.45 (s, 1H), 8.13 (s, 1H), 8.06 (d, 1H), 7.87 (s, 1H), 7.81 (d, 1H), 7.64 (m, 5H), 7.46 (t, 1H), 7.32 (d, 1H), 7.17 (m, 1H), 2.35 (s, 3H). MS (EI) m/z=609 (M+H).

Step 2: N-(3'-[5-Iodo-2-(methylthio)pyrimidin-4-yl] amino-6-methylbiphenyl-3-yl)-3-(trifluoromethyl)-benzamide N-3'-[(2-Chloro-5-iodopyrimidin-4-yl)amino]-6-methyl-biphenyl-3-yl-3-(trifluoromethyl)-benzamide (250 mg, 0.41 mmol) was dissolved in isopropyl alcohol (2.00 mL) with sodium methyl mercaptide (34 mg, 0.49 mmol). The mixture was stirred at 70° C. for 2 hours at which time LCMS analysis showed mainly product. The reaction was extracted with ethyl acetate and the organic extracts were washed with water, saturated NaCl, dried (MgSO$_4$) and concentrated in vacuo. $^1$H NMR (CDCl$_3$): δ 8.39 (s, 1H), 8.13 (s, 1H), 8.06 (d, 1H), 7.81 (m, 2H), 7.53-7.66 (m, 5H), 7.42 (t, 1H), 7.30 (d, 1H), 7.14 (m, 2H), 2.44 (s, 3H), 2.31 (s, 3H). MS (EI) m/z=621 (M+H).

Step 3: N-4-Methyl-3-[2-(methylthio)-9H-pyrimido[4,5-b]indol-7-yl]phenyl-3-(trifluoromethyl)-benzamide N-(3'-[5-Iodo-2-(methylthio)pyrimidin-4-yl]amino-6-methylbiphenyl-3-yl)-3-(trifluoro-methyl)benzamide (0.215 g, 0.346 mmol) was mixed with palladium acetate (0.016 g, 0.069 mmol), tri-o-tolylphosphine (0.042 g, 0.14 mmol) and sodium acetate (0.043 g, 0.52 mmol) in DMF (2.00 mL, 25.9 mmol) and the mixture was heated to reflux for 4 hours. Mass spectral analysis showed ~40% conversion. The reaction was continued for 16 hours at which time LCMS analysis showed ~100% conversion. The reaction was extracted with ethyl acetate and the organic extracts were washed with water, saturated NaCl, dried (MgSO$_4$) and then concentrated in vacuo. The concentrate was chromatographed on silica gel using 30% EtOAc/hexanes to give the product contaminated with deiodinated starting material. This product was washed with ether to give pure product (17.2 mg, 10% yield). $^1$H NMR (CD$_3$OD): δ 9.11 (s, 1H), 8.26 (s, 1H), 8.22 (d, 1H), 8.15 (d, 1H), 7.88 (d, 1H), 7.72 (t, 1H), 7.70 (s, 1H), 7.64 (d, 1H), 7.49 (s, 1H), 7.32 (m, 2H), 2.65 (s, 3H), 2.29 (s, 3H). MS (EI) m/z=493 (M+H).

Step 4: N-4-Methyl-3-[2-(methylsulfonyl)-9H-pyrimido[4,5-b]indol-7-yl]phenyl-3-(trifluoromethyl)-benzamide N-4-Methyl-3-[2-(methylthio)-9H-pyrimido[4,5-b]indol-7-yl]phenyl-3-(trifluoromethyl)-benzamide (16.0 mg, 0.0000325 mol) was dissolved in chloroform (2.00 mL, 0.0250 mol) and methanol (1.0 mL, 0.025 mol) and mCPBA (2.0E1 mg, 0.000071 mol) was added. The resulting mixture was stirred at 25° C. for 16 hours at which time LCMS analysis showed mainly product. The reaction was quenched with NaHSO$_3$ and was extracted with ethyl acetate. The organic extracts were washed with NaHCO$_3$, water, saturated NaCl, dried (MgSO$_4$) and concentrated in vacuo. MS (EI) m/z=525 (M+H).

Step 5: N-[3-(2-Amino-9H-pyrimido[4,5-b]indol-7-yl)-4-methylphenyl]-3-(trifluoromethyl)benzamide trifluoroacetate N-4-Methyl-3-[2-(methylsulfonyl)-9H-pyrimido[4,5-b]indol-7-yl]phenyl-3-(trifluoromethyl)-benzamide (14.0 mg, 0.0267 mmol) was dissolved in ethanol (0.722 mL) and ammonia in water (16 M, 0.260 mL) was added. The reaction was heated at 75° C. for 3 days at which time LCMS analysis showed mainly product with ~30% starting material present and two byproducts. The reaction was rotovaped and the concentrate was purified by prep LC to give the product (4 mg, 26% yield). $^1$H NMR (DMSO-d$_6$) δ 12.41 (brs, 1H), 10.48 (s, 1H), 9.04 (s, 1H), 8.28 (s, 1H), 8.25 (d, 1H), 8.09 (d, 1H), 7.68-7.79 (m, 5H), 7.27-7.35 (m, 3H), 2.24 (s, 3H). MS (EI) m/z=462 (M+H).

Example 68

4-Methyl-3-(9H-pyrido[2,3-b]indol-7-yl)-N-[3-(trifluoromethyl)phenyl]benzamide, trifluoroacetate salt

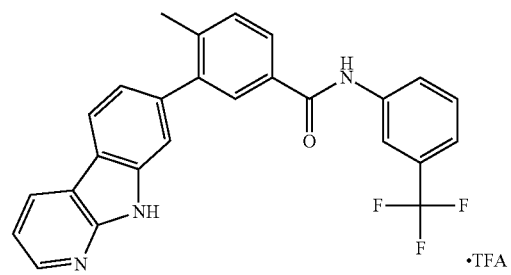 [SMILES: Cc1ccc(C(=O)Nc2cccc(C(F)(F)F)c2)cc1-c1ccc2c(c1)[nH]c1ncccc12]

Step 1: 3-Iodo-4-methyl-N-[3-(trifluoromethyl)phenyl]benzamide

To a suspension of 3-iodo-4-methylbenzoic acid (3.00 g, 11.4 mmol) in DCM (30 mL) at 0° C. was added oxalyl chloride (1.45 mL, 17.2 mmol) followed by two drops of DMF. The reaction was stirred at 0° C. for 30 minutes followed by warming to ambient temperature for 40 minutes. The mixture was concentrated in vacuo. To the resulting residue was added DCM (30 mL), DIPEA (2.99 mL, 17.2 mmol) and 3-(trifluoromethyl)-benzenamine (1.42 mL, 11.4 mmol). The reaction was stirred at ambient temperature for 1 hour. The mixture was then poured into water, and the product was extracted with DCM. The combined organic extracts were washed with water, followed by saturated sodium bicarbonate, and then dried over sodium sulfate. An equal volume of hexane was added and most of the DCM was then removed in vacuo. The resulting yellow solid was filtered, rinsed with hexane and air dried. (4.27 g, 92%).
$^1$H NMR (300 MHz, CDCl$_3$): δ 8.30 (d, 1H), 7.93 (s, 1H), 7.89-7.84 (m, 2H), 7.76 (dd, 1H), 7.50 (t, 1H), 7.41 (d, 1H), 7.35 (d, 1H), 2.50 (s, 3H); MS (ES) (M+H)=405.9.

Step 2: 6-Methyl-3'-nitro-N-[3-(trifluoromethyl)phenyl]biphenyl-3-carboxamide 4,4,5,5-Tetramethyl-2-(3-nitrophenyl)-1,3,2-dioxaborolane (1.4 g, 5.6 mmol) was mixed with 3-iodo-4-methyl-N-[3-(trifluoromethyl)phenyl]benzamide (2.00 g, 4.94 mmol), potassium carbonate (1.4 g, 9.9 mmol), toluene (40 mL), ethanol (6.0 mL), and water (4.0 mL). The mixture was degassed and tetrakis(triphenylphosphine)palladium(0) (0.27 g, 0.24 mmol) was added. The resulting mixture was heated to reflux for 16 hours. The reaction was then cooled and was extracted with ethyl acetate. The organic extracts were washed with water, brine, dried (Na$_2$SO$_4$) and concentrated. The product was purified by flash column chromatography, eluting with a gradient of 20-50% ethyl acetate in hexanes (1.92 g, 91%).
$^1$H NMR (300 MHz, CDCl$_3$): δ 8.26 (dt, 1H), 8.22 (t, 1H), 7.99 (s, 1H), 7.88 (d, 1H), 7.83 (dd, 1H), 7.76 (d, 1H), 7.69 (dt, 1H), 7.65 (q, 1H), 7.53-7.38 (m, 3H), 2.34 (s, 3H); MS (ES) (M+H)=401.0.

Step 3: 3'-Amino-6-methyl-N-[3-(trifluoromethyl) phenyl]biphenyl-3-carboxamide To 6-methyl-3'-nitro-N-[3-(trifluoromethyl)phenyl]biphenyl-3-carboxamide (0.90 g, 2.2 mmol) in ethanol (22 mL) was added acetic acid (2 mL) and iron (0.90 g, 16 mmol) and the resulting mixture was heated to reflux for 1 hour. Solvent was removed in vacuo. Ethyl acetate was added and solids were removed by filtration. The filtrate was washed sequentially with saturated sodium bicarbonate and brine, dried ($Na_2SO_4$) and then concentrated. The product was used without further purification (850 mg, 95%).

$^1$H NMR (300 MHz, $CDCl_3$): δ 8.36 (s, 1H), 7.93 (s, 1H), 7.86 (d, 1H), 7.74 (d, 1H), 7.66 (s, 1H), 7.48-7.23 (m, 3H), 7.17 (t, 1H), 6.70-6.62 (m, 2H), 6.57 (s, 1H), 3.79-3.29 (br s, 2H), 2.30 (s, 3H); MS (ES) (M+H)=371.1.

Step 4: 3'-[(3-Bromopyridin-2-yl)amino]-6-methyl-N-[3-(trifluoromethyl)phenyl]biphenyl-3-carboxamide A mixture of 3'-amino-6-methyl-N-[3-(trifluoromethyl) phenyl]biphenyl-3-carboxamide (150 mg, 0.41 mmol) and 3-bromo-2-chloropyridine (90 mg, 0.47 mmol) was heated neat to 180° C. in an oil bath. The temperature was increased to 200° C., and then heating was discontinued and the reaction mixture was allowed to stir for 72 h. The resulting solid was dissolved in methanol and purified by flash column chromatography (eluting with a gradient of 0-40% ethyl acetate in hexanes) to afford product (87 mg, 39%).

$^1$H NMR (300 MHz, $CDCl_3$): δ 8.45 (s, 1H), 8.15 (dd, 1H), 8.00 (s, 1H), 7.90 (d, 1H), 7.81-7.74 (m, 3H), 7.58 (t, 1H), 7.55-7.50 (m, 1H), 7.44 (t, 1H), 7.39-7.33 (m, 3H), 7.13 (s, 1H), 6.99 (dt, 1H), 6.67 (dd, 1H), 2.36 (s, 3H); MS (ES) (M+H)=526.0/528.0.

Step 5: 4-Methyl-3-(9H-pyrido[2,3-b]indol-7-yl)-N-[3-(trifluoromethyl)phenyl]benzamide trifluoroacetate salt To a degassed mixture of 3'-[(3-bromopyridin-2-yl) amino]-6-methyl-N-[3-(trifluoromethyl)-phenyl]biphenyl-3-carboxamide (0.085 g, 0.16 mmol) and sodium acetate (20 mg, 0.24 mmol) in DMF (4 mL) was added tri-o-tolylphosphine (9.8 mg, 0.032 mmol) and palladium acetate (3.6 mg, 0.016 mmol). The mixture was degassed again and then was heated to vigorous reflux for 3 hours. The mixture was then cooled, filtered and purified by preparative HPLC-MS (C18 eluting with a gradient of MeCN/$H_2O$ containing 0.1% TFA), then lyophilized to afford the product (50 mg, 55%). $^1$H NMR (400 MHz, $d_6$-DMSO): δ12.03 (s, 1H), 10.54 (s, 1H), 8.62 (d, 1H), 8.46 (dd, 1H), 8.28 (d, 1H), 8.25 (s, 1H), 8.08 (d, 1H), 8.01-7.98 (m, 1H), 7.95 (dd, 1H), 7.59 (t, 1H), 7.55-7.49 (m, 2H), 7.45 (d, 1H), 7.33-7.26 (m, 2H), 2.35 (s, 3H); MS (ES) (M+H)=446.1.

Example 69

4-Methyl-3-(9H-pyrido[3',2':4,5]pyrrolo[2,3-d]pyrimidin-7-yl)-N-[3-(trifluoro-methyl)phenyl]benzamide

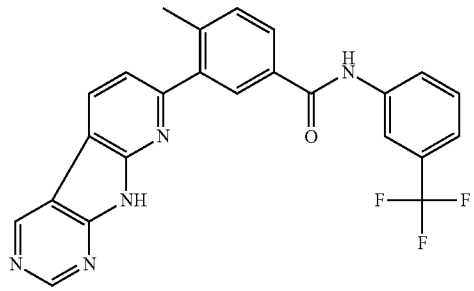 [SMILES: Cc1ccc(C(=O)Nc2cccc(C(F)(F)F)c2)cc1-c1ccc2c(n1)[nH]c1ncncc12]

Step 1: 3-(6-Aminopyridin-2-yl)-4-methyl-N-[3-(trifluoromethyl)phenyl]benzamide To a degassed mixture of 3-iodo-4-methyl-N-[3-(trifluoromethyl)phenyl]benzamide (0.500 g, 1.23 mmol), potassium acetate (424 mg, 4.32 mmol), DMF (15 mL), and 4,4,5,5,4',4',5',5'-octamethyl-[2,2]bi[[1,3,2]dioxaborolanyl] (0.329 g, 1.30 mmol) was added [1,1'-bis(diphenylphosphino)-ferrocene]dichloropalladium(II), complex with DCM (1:1) (101 mg, 0.123 mmol). The reaction was heated to 80° C. for 3 hours, at which time conversion to the boronic ester was complete. The mixture was cooled and potassium carbonate (512 mg, 3.70 mmol), water (2.24 mL), and 6-bromopyridin-2-amine (214 mg, 1.23 mmol) were added. After degassing the mixture, it was heated to 85° C. for 1 hour. The solvent was then removed in vacuo. Water was added and the product was extracted with three portions of ethyl acetate. The combined extracts were washed with brine, dried over sodium sulfate, and concentrated. Purification was carried out by flash column chromatography (eluting with a gradient from 0-50% ethyl acetate in hexanes) afforded the product. (254 mg, 50%).

$^1$H NMR (300 MHz, $CDCl_3$ containing $CD_3OD$): δ 7.94-7.87 (m, 2H), 7.83-7.77 (m, 2H), 7.49 (dd, 1H), 7.42 (t, 1H), 7.36-7.29 (m, 2H), 6.70 (dd, 1H), 6.50 (dd, 1H), 2.35 (s, 3H); MS (ES) (M+H)=372.0.

Step 2: 3-6-[(5-Iodopyrimidin-4-yl)amino]pyridin-2-yl-4-methyl-N-[3-(trifluoromethyl)phenyl]-benzamide A solution of 3-(6-aminopyridin-2-yl)-4-methyl-N-[3-(trifluoromethyl)phenyl]benzamide (0.15 g, 0.42 mmol) in THF (8 mL) at 0° C. was treated with sodium bis(trimethylsilyl) amide in THF (1.00 M, 1.0 mL). This mixture was stirred for 25 minutes followed by the addition of 4-chloro-5-iodopyrimidine (0.100 g, 0.416 mmol) as a solution in THF (3 mL). The resulting mixture was stirred with gradual warming for 1.5 hours. A further portion of sodium bis(trimethylsilyl) amide in THF (1.00 M, 0.3 mL) was added. The reaction was allowed to reach room temp over 15 minutes. The reaction mixture was poured into water and extracted with ethyl acetate. The extracts were washed with brine, dried over sodium sulfate and concentrated. The solid was slurried in a small amount of ethyl acetate and filtered off to provide 140 mg of 3-6-[(5-iodopyrimidin-4-yl)amino]pyridin-2-yl-4-methyl-N-[3-(trifluoromethyl)phenyl]benzamide as a solid product. The mother liquor was purified by flash column chromatography (eluting with a gradient from 0-50% ethyl acetate/hexanes) to provide an additional 65 mg of 3-6-[(5-iodopyrimidin-4-yl)amino]pyridin-2-yl-4-methyl-N-[3-(trifluoro-methyl)phenyl]benzamide as a film (205 mg, 80%). MS (ES) (M+H)=576.0.

Step 3: 4-Methyl-3-(9H-pyrido[3',2':4,5]pyrrolo[2,3-d]pyrimidin-7-yl)-N-[3-(trifluoromethyl)phenyl] benzamide To a degassed mixture of the above generated 3-6-[(5-iodopyrimidin-4-yl)amino]pyridin-2-yl-4-methyl-N-[3-(trifluoromethyl)phenyl]benzamide (0.070 g, 0.11 mmol) in TEA (0.1 mL, 0.8 mmol) and DMF (1.3 mL) was added [1,1'-bis(diphenylphosphino)ferrocene]dichloropalladium (II), complex with DCM (1:1) (9.2 mg, 0.011 mmol) and the resulting mixture was degassed again. The reaction was heated to reflux for 7 hours. The reaction was then cooled, filtered and purified by preparative HPLC-MS (C18 eluting with a gradient of MeCN/H$_2$O containing 0.15% NH$_4$OH) and lyophilized to afford the product (1 mg, 2%).
$^1$H NMR (500 MHz, d$_6$-DMSO): δ☐ 10.54 (s, 1H), 9.38 (s, 1H), 8.89 (s, 1H), 8.64 (s, 1H), 8.24 (s, 1H), 8.14 (d, 1H), 8.08 (d, 1H), 7.96 (d, 1H), 7.64-7.41 (m, 5H); MS (ES) (M+H)=448.1.

Example 70

N-[6-methyl-5-(9H-pyrimido[4,5-b]indol-7-yl)pyridin-3-yl]-3-(trifluoromethyl)benzamide

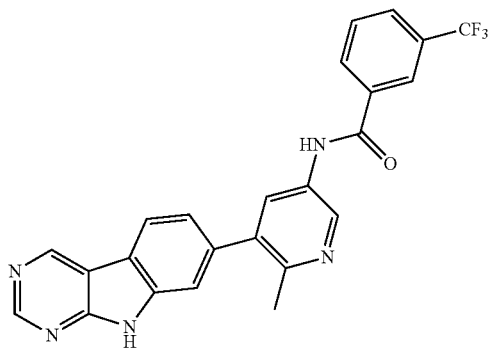 [SMILES: Cc1ncc(NC(=O)c2cccc(C(F)(F)F)c2)cc1-c1ccc2c(c1)[nH]c1ncncc12]

Step 1: 2-chloro-3-iodo-5-nitropyridine

3-Iodo-5-nitropyridin-2-ol (3.00 g, 0.0113 mol) was heated to reflux in phosphoryl chloride (15 mL, 0.1609 mol) for 4 hours. The reaction was quenched in ice/water and was neutralized with Na$_2$CO$_3$. The reaction was extracted with ethyl acetate and the organic extracts were washed with water, saturated NaCl, dried (MgSO$_4$) and stripped in vacuo to give the product, which was used in the next reaction without purification.

Step 2: diethyl (3-iodo-5-nitropyridin-2-yl)malonate

To a round-bottom flask containing sodium hydride (0.56 g, 0.014 mol) suspended in tetrahydrofuran (25 mL) was added ethyl malonate (2.0 mL, 0.013 mol) dropwise, and was stirred at 25° C. for 5 minutes. To this reaction mixture was added 2-chloro-3-iodo-5-nitropyridine (2.5 g, 0.00879 mol) and was stirred at 25° C. for 4 hours. The reaction was diluted with EtOAc and water and was acidified with a few drops of AcOH. Then it was extracted with EtOAc and the organic extracts were washed with water, saturated NaCl, dried (MgSO$_4$) and stripped in vacuo. The reaction was chromatographed on silica gel using 10% EtOAc/hexanes, followed by 20% EtOAc/hexanes to give the product (2.66 g, 74%). $^1$H NMR (400 MHZ, CDCl$_3$): δ 9.35 (d, 1H), 8.89 (d, 1H), 5.27 (s, 1H), 4.31 (q, 4H), 1.30 (t, 6H); MS (ES) (M+H)=409.

Step 3. 3-iodo-2-methyl-5-nitropyridine

Diethyl (3-iodo-5-nitropyridin-2-yl)malonate (0.250 g, 0.000612 mol) was heated in 6 M sulfuric acid (3 mL) at 100° C. for 16 hours. The reaction was neutralized with solid Na$_2$CO$_3$, extracted with EtOAc and the organic extracts were washed with water, saturated NaCl, dried (MgSO$_4$) and stripped in vacuo. NMR analysis indicated that it was clean enough for the next reaction. $^1$H NMR (400 MHZ, CDCl$_3$): δ 9.27 (d, 1H), 8.82 (d, 1H), 2.87 (s, 3H); MS (ES) (M+H)=265.

Step 4: 5-iodo-6-methylpyridin-3-amine

To a solution of 3-iodo-2-methyl-5-nitropyridine (125 mg, 0.4734 mmol) in ethanol (3 mL) was added acetic acid (0.50 mL, 8.8 mmol) and iron powder (140 mg, 2.6 mmol). The reaction was heated at 85° C. for 30 minutes and was diluted with EtOAc, water, and saturated Na$_2$CO$_3$. Then it was filtered and extracted with EtOAc and the organic extracts were washed with water, saturated NaCl, dried (MgSO$_4$) and stripped in vacuo. $^1$H NMR (400 MHz, CDCl$_3$): δ 7.96 (d, 1H), 7.44 (d, 1H), 3.57 (br s, 2H), 2.61 (s, 3H); MS (ES) (M+H)=235.

Step 5: N-(5-iodo-6-methylpyridin-3-yl-3-(trifluoromethyl)benzamide

To a solution of 5-iodo-6-methylpyridin-3-amine (125 mg, 0.534 mmol) in methylene chloride (1 mL) was added triethylamine (0.087 mL, 0.627 mmol) and cooled at 0° C. Into the reaction was added 3-(trifluoromethyl)benzoyl chloride (0.0812 mL, 0.538 mmol) dropwise and stirred at 0° C. for 45 minutes and at 25° C. for 16 hours. The reaction was extracted with EtOAc and the organic extracts were washed with water saturated Na$_2$CO$_3$, saturated NaCl, dried (MgSO$_4$) and stripped in vacuo. The product was used in the next reaction without purification.

Step 6: N-[6-methyl-5-(3-nitrophenyl)pyridin-3-yl]-3-(trifluoromethyl)benzamide (3-Nitrophenyl)boronic acid (0.086 g, 0.52 mmol) was mixed with N-(5-iodo-6-methylpyridin-3-yl)-3-(trifluoromethyl)benzamide (0.21 g, 0.52 mmol) and potassium carbonate (0.13 g, 0.91 mmol) in toluene (3.8 mL), ethanol (0.56 mL) and water (0.5 mL) and the solution was degassed. Into the reaction was added tetrakis(triphenylphosphine)palladium(0) (0.025 g, 0.022 mmol) and was refluxed for 18 hours. The reaction was extracted with EtOAc and the organic extracts were washed with water, saturated NaCl, dried (MgSO$_4$) and stripped in vacuo. The residue was purified by column chromatography using 40% EtOAc/hexanes to give the product (0.156 g, 75% yield). $^1$H NMR (400 MHZ, CDCl$_3$): δ 8.67 (d, 1H), 8.28 (m, 2H), 8.16 (brs, 1H), 8.11 (m, 1H), 7.99 (brs, 1H), 7.85 (m, 1H), 7.69 (m, 4H), 2.52 (s, 3H); MS (ES) (M+H)=402.

Step 7: N-[5-(3-aminophenyl)-6-methylpyridin-3-yl]-3-(trifluoromethyl)benzamide To a solution of N-[6-methyl-5-(3-nitrophenyl)pyridin-3-yl]-3-(trifluoromethyl)benzamide (0.150 g, 0.000374 mol) in ethanol (3 mL) was added acetic acid (0.5 mL, 0.009 mol) and iron powder (0.11 g, 0.0020 mol). The reaction was heated at 87° C. for 2 hours. It was then neutralized with Na$_2$CO$_3$ and extracted with EtOAc and the organic extracts were washed with water, saturated NaCl, dried (MgSO$_4$) and stripped in vacuo. The residue was used in the next reaction without purification. MS (ES) (M+H)=372.

Step 8: N-(5-3-[(5-iodopyrimidin-4-yl)amino]phenyl-6-methylpyridin-3-yl)-3-(trifluoromethyl)benzamide N-[5-(3-aminophenyl)-6-methylpyridin-3-yl]-3-(trifluoromethyl)benzamide (135 mg, 0.3635 mmol) was refluxed with 4-chloro-5-iodopyrimidine (96 mg, 0.40 mmol) in ethanol (4.0 mL), for 16 hours at which time LCMS analysis showed mainly product. The reaction was quenched with saturated Na$_2$CO$_3$ and was extracted with EtOAc and the organic extracts were washed with water, saturated NaCl, dried (MgSO$_4$) and stripped in vacuo. The reaction was chromatographed on silica gel using 1:1 EtOAc/hexanes and 2% Et$_3$N to give the product (0.151 mg, 72% yield). $^1$H NMR (400 MHZ, CDCl$_3$): δ 8.65 (s, 1H), 8.64 (m, 1H), 8.59 (s, 1H), 8.16 (m, 2H), 8.10 (m, 1H), 7.99 (brs, 1H), 7.84 (m, 1H), 7.66 (m, 3H), 7.48 (m, 1H), 7.18 (m, 2H), 2.56 (s, 3H); MS (ES) (M+H)=576.

Step 9: N-[6-methyl-5-(9H-pyrimido[4,5-b]indol-7-yl)pyridin-3-yl]-3-(trifluoromethyl)benzamide N-(5-3-[(5-iodopyrimidin-4-yl)amino]phenyl-6-methylpyridin-3-yl)-3-(trifluoromethyl)benzamide (150 mg, 0.2607 mmol) was mixed with palladium acetate (6.2 mg, 0.028 mmol), tri-o-tolylphosphine (16.8 mg, 0.0552 mmol) and sodium acetate in N,N-Dimethylformamide (1.6 mL). The mixture was degassed and stirred for 5 minutes. The reaction was heated at 148° C. (oil bath temperature) for 16 hours. A third of the reaction was evaporated and purified by prep. LC. to give the product contaminated with deiodinated material. The reaction was extracted with EtOAc and the organic extracts were washed with water, saturated NaCl, dried (MgSO$_4$) and stripped in vacuo. The reaction was triturated with ether and washed with ether to give clean material (37 mg), which was purified by prep LC. $^1$H NMR (400 MHZ, DMSO-D$_6$): δ 13.11 (brs, 1H), 10.90 (s, 1H), 9.67 (s, 1H), 9.15 (s, 1H), 9.02 (d, 1H), 8.45 (d, 1H), 8.34 (m, 3H), 8.00 (m, 1H), 7.82 (t, 1H), 7.68 (s, 1H), 7.52 (m, 1H), 2.53 (s, 3H); MS (ES) (M+H)=448.

Example 71

3-Fluoro-N-[6-methyl-5-(9H-pyrimido[4,5-b]indol-7-yl)pyridin-3-yl]-5-(trifluoromethyl)benzamide

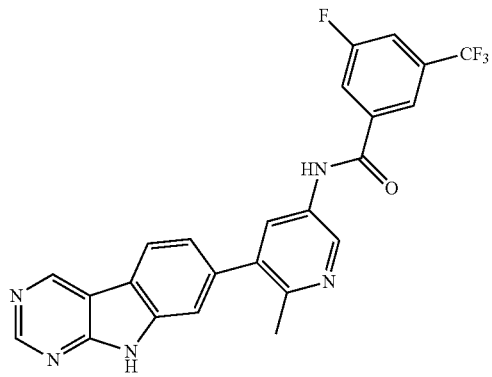 [SMILES: Cc1ncc(NC(=O)c2cc(F)cc(C(F)(F)F)c2)cc1-c1ccc2c(c1)[nH]c1ncncc12]

3-Fluoro-N-(5-3-[(5-iodopyrimidin-4-yl)amino]phenyl-6-methylpyridin-3-yl)-5-(trifluoromethyl)benzamide (2.80 g, 4.72 mmol), synthesized in an analogous manner as in Example 70, was mixed with palladium acetate (0.11 g, 0.50 mmol), tri-o-tolylphosphine (0.30 g, 1.0 mmol) and sodium acetate in N,N-dimethylformamide (20 mL) and was degassed and stirred for 5 minutes. The reaction was heated at 155° C. (oil bath temperature) for 16 hours and at 165° C. (oil bath temperature) for 6 hours. Then it was extracted with EtOAc and the organic extracts were washed with water, saturated NaCl, dried (MgSO$_4$) and stripped in vacuo. The reaction was triturated with ether and was washed with ether to give clean material (1.02 g). $^1$H NMR (400 MHZ, DMSO-D$_6$): δ 12.46 (s, 1H), 10.73 (s, 1H), 9.50 (s, 1H), 8.95 (s, 1H), 8.87 (d, 1H), 8.35 (d, 1H), 8.20 (s, 1H), 8.13 (s, 1H), 8.00 (m, 1H), 7.93 (m, 1H), 7.54 (s, 1H), 7.40 (d, 1H); MS (ES) (M+H)=466.

Example 72

3-(1H-imidazol-1-yl)-N-[6-methyl-5-(9H-pyrimido[4,5-b]indol-7-yl)pyridin-3-yl]-5-(trifluoromethyl)benzamide tris(trifluoroacetate)

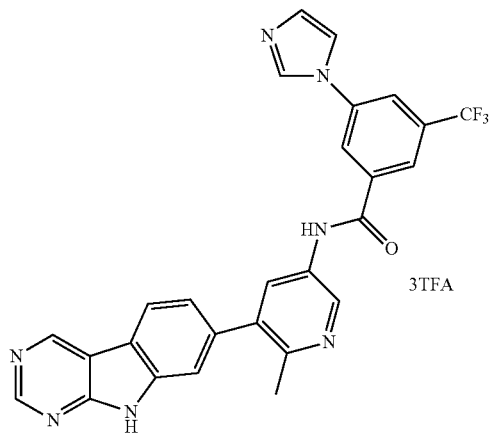 [SMILES: Cc1ncc(NC(=O)c2cc(-n3ccnc3)cc(C(F)(F)F)c2)cc1-c1ccc2c(c1)[nH]c1ncncc12]

To a solution of 3-fluoro-N-[6-methyl-5-(9H-pyrimido[4,5-b]indol-7-yl)pyridin-3-yl]-5-(trifluoromethyl)benzamide (0.023 g, 0.049 mmol) in N,N-dimethylformamide (0.50 mL) was added 1H-imidazole (0.016 g, 0.24 mmol) and potassium carbonate (0.034 g, 0.25 mmol) and was heated at 120° C. for 16 hours. The reaction was diluted with THF, was filtered, was rotovaped and was purified by preparative LC to give the product. $^1$H NMR (400 MHZ, DMSO-D$_6$): δ 13.06 (brs, 1H), 10.99 (s, 1H), 9.65 (s, 1H), 9.54 (brs, 1H), 9.13 (s, 1H), 8.99 (d, 1H), 8.64 (s, 1H), 8.44 (m, 3H), 8.36 (s, 1H), 8.25 (d, 1H), 7.78 (s, 1H), 7.66 (s, 1H), 7.50 (m, 1H), 2.52 (s, 1H); MS (ES) (M+H)=514.

The following compounds in Tables 1, 2, 3, and 4 were made by methods analogous to the procedures above as indicated

TABLE 1

| Ex. No. | R | Ar | Name | Prep. | MS |
|---|---|---|---|---|---|
| 3 | CH$_3$ | 2-F-3-CF$_3$C$_6$H$_3$ | 2-fluoro-N-[4-methyl-3-(9H-pyrimido[4,5-b]indol-7-yl)-phenyl]-3-(trifluoromethyl)-benzamide | Ex. 2 | 465 |
| 4 | CH$_3$ | 4-F-3-CF$_3$C$_6$H$_3$ | 4-fluoro-N-[4-methyl-3-(9H-pyrimido[4,5-b]indol-7-yl)-phenyl]-3-(trifluoromethyl)benzamide | Ex. 2 | 465 |
| 5 | CH$_3$ | 6-F-3-CF$_3$C$_6$H$_3$ | 2-fluoro-N-[4-methyl-3-(9H-pyrimido[4,5-b]indol-7-yl)-phenyl]-5-(trifluoromethyl)-benzamide | Ex. 2 | 465 |
| 6 | CH$_3$ | 3-F-C$_6$H$_4$ | 3-fluoro-N-[4-methyl-3-(9H-pyrimido[4,5-b]indol-7-yl)-phenyl]benzamide | Ex. 1 | 396 |
| 7 | CH$_3$ | 2,5-(CF$_3$)$_2$C$_6$H$_3$ | N-[4-methyl-3-(9H-pyrimido[4,5-b]indol-7-yl)phenyl]-2,5-bis(trifluoromethyl)benzamide | Ex. 2 | 515 |
| 8 | CH$_3$ | 3-Cl-2-F-5-CF$_3$C$_6$H$_2$ | 3-chloro-2-fluoro-N-[4-methyl-3-(9H-pyrimido[4,5-b]-indol-7-yl)phenyl]-5-(trifluoromethyl)benzamide | Ex. 2 | 499 |
| 9 | CH$_3$ | 3,5-(CF$_3$)$_2$C$_6$H$_3$ | N-[4-methyl-3-(9H-pyrimido-[4,5-b]indol-7-yl)phenyl]-3,5-bis(trifluoromethyl)benzamide | Ex. 2 | 515 |
| 10 | CH$_3$ | 4-OCH$_3$—3CF$_3$C$_6$H$_3$ | 4-methoxy-N-[4-methyl-3-(9H-pyrimido[4,5-b]indol-7-yl)-phenyl]-3-(trifluoromethyl)-benzamide | Ex. 2 | 477 |
| 11 | CH$_3$ | 3-OCH$_3$C$_6$H$_4$ | 3-methoxy-N-[4-methyl-3-(9H-pyrimido[4,5-b]indol-7-yl)-phenyl]benzamide | Ex. 2 | 409 |
| 12 | CH$_3$ | 2-CF$_3$C$_6$H$_4$ | N-[4-methyl-3-(9H-pyrimido-[4,5-b]indol-7-yl)phenyl]-2-(trifluoromethyl)benzamide | Ex. 2 | 447 |
| 13 | F | 3-CF$_3$C$_6$H$_4$ | N-[4-fluoro-3-(9H-pyrimido-[4,5-b]indol-7-yl)phenyl]-3-(trifluoromethyl)benzamide | Ex. 2 | 451 |
| 14 | H | 3-CF$_3$C$_6$H$_4$ | N-[3-(9H-pyrimido[4,5-b]-indol-7-yl)phenyl]-3-(trifluoromethyl)benzamide | Ex. 2 | 433 |
| 15 | CH$_3$ | 3-ClC$_6$H$_4$ | 3-chloro-N-[4-methyl-3-(9H-pyrimido[4,5-b]indol-7-yl)-phenyl]benzamide | Ex. 2 | 413 |
| 16 | CH$_3$ | 3-SF$_5$C$_6$H$_4$ | N-[4-methyl-3-(9H-pyrimido-[4,5-b]indol-7-yl)phenyl]-3-(pentafluoro-λ(6)-sulfanyl)-benzamide | Ex. 2 | 505 |
| 17 | Cl | 3-CF$_3$C$_6$H$_4$ | N-[4-chloro-3-(9H-pyrimido-[4,5-b]indol-7-yl)phenyl]-3-(trifluoromethyl)benzamide | Ex. 2 | 467 |

TABLE 1-continued

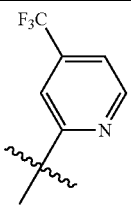

| Ex. No. | R | Ar | Name | Prep. | MS |
|---|---|---|---|---|---|
| 18 | CH₃ | 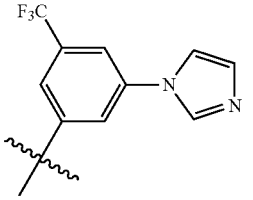 [SMILES: *c1cc(-n2ccnc2)cc(C(F)(F)F)c1] | N-[4-methyl-3-(9H-pyrimido[4,5-b]indol-7-yl)-phenyl]-4-(trifluoromethyl)pyridine-2-carboxamide | Ex. 2 | 448 |
| 23 | CH₃ | 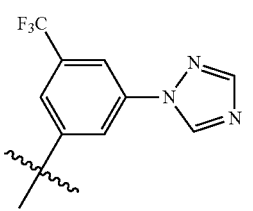 [SMILES: *c1cc(-n2cncn2)cc(C(F)(F)F)c1] | 3-(1H-imidazol-1-yl)-N-[4-methyl-3-(9H-pyrimido[4,5-b]-indol-7-yl)phenyl]-5-(trifluoromethyl)benzamide | Ex. 20 | 513 |
| 24 | CH₃ | 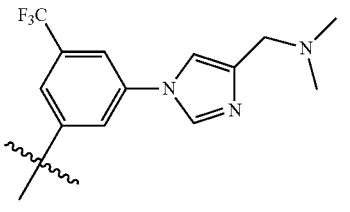 [SMILES: *c1cc(-n2cnc(CN(C)C)c2)cc(C(F)(F)F)c1] | N-[4-methyl-3-(9H-pyrimido-[4,5-b]indol-7-yl)phenyl]-3-(1H-1,2,4-triazol-1-yl)-5-(trifluoromethyl)benzamide | Ex. 20 | 514 |
| 25 | CH₃ | 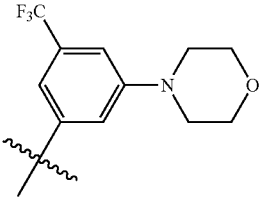 [SMILES: *c1cc(N2CCOCC2)cc(C(F)(F)F)c1] | 3-{4-[(dimethylamino)methyl]-1H-imidazol-1-yl}-N-[4-methyl-3-(9H-pyrimido[4,5-b]-indol-7-yl)phenyl]-5-(trifluoro-methyl)benzamide | Ex. 22 | 570 |
| 27 | CH₃ | 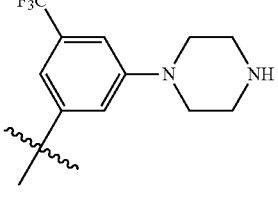 | N-[4-methyl-3-(9H-pyrimido-[4,5-b]indol-7-yl)phenyl]-3-morpholin-4-yl-5-(trifluoromethyl)benzamide | Ex. 26 | 532 |
| 28 | CH₃ |  | N-[4-methyl-3-(9H-pyrimido-[4,5-b]indol-7-yl)phenyl]-3-piperazin-1-yl-5-(trifluoro-methyl)benzamide | Ex. 26 | 531 |

TABLE 1-continued

| Ex. No. | R | Ar | Name | Prep. | MS |
|---|---|---|---|---|---|
| 29 | CH₃ | 3-CF₃-5-(4-hydroxypiperidin-1-yl)phenyl | 3-(4-hydroxypiperidin-1-yl)-N-[4-methyl-3-(9H-pyrimido[4,5-b]indol-7-yl)phenyl]-5-(trifluoromethyl)benzamide | Ex. 26 | 546 |
| 30 | CH₃ | 3-CF₃-5-(3-hydroxypiperidin-1-yl)phenyl | 3-(3-hydroxypiperidin-1-yl)-N-[4-methyl-3-(9H-pyrimido[4,5-b]indol-7-yl)phenyl]-5-(trifluoromethyl)benzamide | Ex. 26 | 546 |
| 31 | CH₃ | 3-CF₃-5-[(2-morpholin-4-ylethyl)amino]phenyl | N-[4-methyl-3-(9H-pyrimido-[4,5-b]indol-7-yl)phenyl]-3-[(2-morpholin-4-ylethyl)amino]-5-(trifluoromethyl)benzamide | Ex. 26 | 575 |
| 32 | CH₃ | 3-CF₃-5-[4-(2-hydroxyethyl)piperazin-1-yl]phenyl | 3-[4-(2-hydroxyethyl)piperazin-1-yl]-N-[4-methyl-3-(9H-pyrimido[4,5-b]indol-7-yl)-phenyl]-5-(trifluoromethyl)-benzamide | Ex. 26 | 575 |
| 33 | CH₃ | 3-CF₃-5-{[3-(dimethylamino)propyl]amino}phenyl | 3-{[3-(dimethylamino)propyl]-amino}-N-[4-methyl-3-(9H-pyrimido[4,5-b]indol-7-yl)-phenyl]-5-(trifluoromethyl)-benzamide | Ex. 26 | 547 |
| 34 | CH₃ | 3-CF₃-5-(3-hydroxypyrrolidin-1-yl)phenyl | 3-(3-hydroxypyrrolidin-1-yl)-N-[4-methyl-3-(9H-pyrimido-[4,5-b]indol-7-yl)phenyl]-5-(trifluoromethyl)benzamide | Ex. 26 | 532 |

TABLE 1-continued

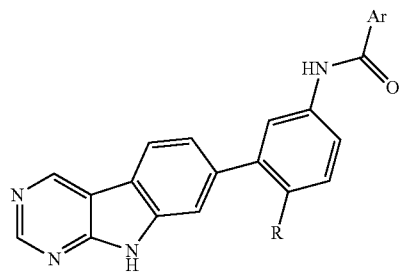

| Ex. No. | R | Ar | Name | Prep. | MS |
|---|---|---|---|---|---|
| 35 | CH$_3$ | (3-CF$_3$-5-(3-(1H-imidazol-1-yl)propylamino)phenyl) | 3-{[3-(1H-imidazol-1-yl)-propyl]amino}-N-[4-methyl-3-(9H-pyrimido[4,5-b]indol-7-yl)phenyl]-5-(trifluoromethyl)-benzamide | Ex. 26 | 570 |
| 36 | CH$_3$ | (3-CF$_3$-5-dimethylaminophenyl) | 3-(dimethylamino)-N-[4-methyl-3-(9H-pyrimido[4,5-b]-indol-7-yl)phenyl]-5-(trifluoromethyl)benzamide | Ex. 26 | 490 |
| 37 | CH$_3$ | (3-CF$_3$-5-(3-(dimethylamino)pyrrolidin-1-yl)phenyl) | 3-[3-(dimethylamino)-pyrrolidin-1-yl]-N-[4-methyl-3-(9H-pyrimido[4,5-b]indol-7-yl)phenyl]-5-(trifluoromethyl)-benzamide | Ex. 26 | 559 |
| 38 | CH$_3$ | (3-CF$_3$-5-(2-(dimethylamino)ethylamino)phenyl) | 3-{[2-(dimethylamino)ethyl]-amino}-N-[4-methyl-3-(9H-pyrimido[4,5-b]pyrimido[4,5-b]-pyrimido[4,5-b]indol-7-yl)-phenyl]-5-(trifluoromethyl)benzamide | Ex. 26 | 533 |

TABLE 2

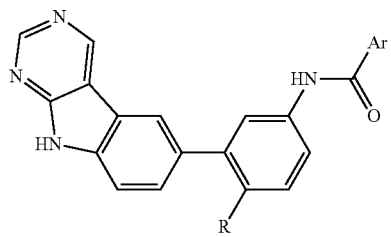

| Ex. No. | R | Ar | Name | Prep. | MS |
|---|---|---|---|---|---|
| 42 | CH$_3$ | 4-F-3-CF$_3$C$_6$H$_3$ | 4-fluoro-N-[4-methyl-3-(9H-pyrimido[4,5-b] | Ex. 41 | 465 |

TABLE 2-continued

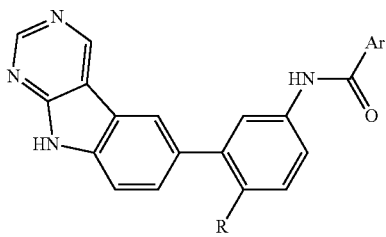

| Ex. No. | R | Ar | Name | Prep. | MS |
|---|---|---|---|---|---|
| | | | indol-6-yl)-phenyl]-3-(trifluoromethyl)-benzamide | | |

TABLE 2-continued

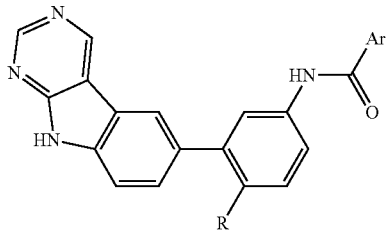

| Ex. No. | R | Ar | Name | Prep. | MS |
|---|---|---|---|---|---|
| 43 | CH$_3$ | 5-F-3-CF$_3$C$_6$H$_3$ | 3-fluoro-N-[4-methyl-3-(9H-pyrimido[4,5-b]indol-6-yl)-phenyl]-5-(trifluoromethyl)-benzamide | Ex. 41 | 465 |
| 44 | CH$_3$ | 3F—C$_6$H$_4$ | 3-fluoro-N-[4-methyl-3-(9H-pyrimido[4,5-b]indol-6-yl)-phenyl]benzamide | Ex. 41 | 397 |
| 45 | CH$_3$ | 2,5-(CF$_3$)$_2$C$_6$H$_3$ | N-[4-methyl-3-(9H-pyrimido-[4,5-b] | Ex. 41 | 515 |

TABLE 2-continued

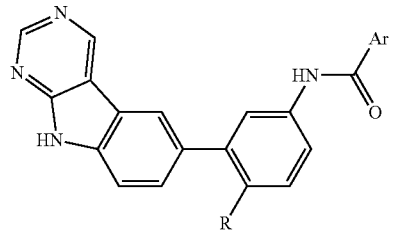

| Ex. No. | R | Ar | Name | Prep. | MS |
|---|---|---|---|---|---|
|  |  |  | indol-6-yl)phenyl]-2,5-bis(trifluoromethyl)benzamide |  |  |
| 46 | CH$_3$ | 3-Cl-2-F-5-CF$_3$C$_6$H$_2$ | 3-chloro-2-fluoro-N-[4-methyl-3-(9H-pyrimido[4,5-b]indol-6-yl)phenyl]-5-(trifluoromethyl)-benzamide | Ex. 41 | 499 |

TABLE 3

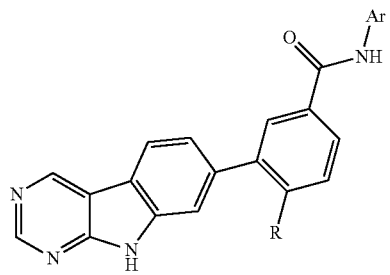

| Ex. No. | R | Ar | Name | Prep. | MS |
|---|---|---|---|---|---|
| 52 | CH$_3$ | 3-CF$_3$C$_6$H$_4$ | 4-methyl-3-(9H-pyrimido-[4,5-b]indol-7-yl)-N-[3-(trifluoromethyl)phenyl]benzamide | Ex. 50 | 393 |
| 53 | CH$_3$ | 3-CH$_3$C$_6$H$_4$ | 4-methyl-N-(3-methyl-phenyl)-3-(9H-pyrimido-[4,5-b]indol-7-yl)benzamide | Ex. 50 | 393 |
| 54 | CH$_3$ | 3-CF$_3$OC$_6$H$_4$ | 4-methyl-3-(9H-pyrimido-[4,5-b]indol-7-yl)-N-[3-(trifluoromethoxy)phenyl]-benzamide | Ex. 50 | 463 |
| 55 | CH$_3$ | 3,6-F$_2$C$_6$H$_3$CH$_2$ | N-(2,5-difluorobenzyl)-4-methyl-3-(9H-pyrimido-[4,5-b]indol-7-yl)benzamide | Ex. 50 | 429 |
| 56 | CH$_3$ | 3-CF$_3$C$_6$H$_4$CH$_2$ | 4-methyl-3-(9H-pyrimido-[4,5-b]indol-7-yl)-N-[3-(trifluoromethyl)benzyl]-benzamide | Ex. 50 | 461 |

TABLE 3-continued

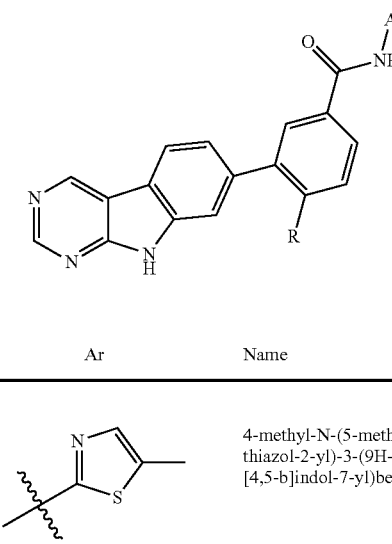

| Ex. No. | R | Ar | Name | Prep. | MS |
|---|---|---|---|---|---|
| 57 | CH$_3$ | 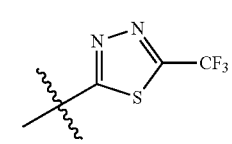 [SMILES: *c1nnc(C(F)(F)F)s1] | 4-methyl-N-(5-methyl-1,3-thiazol-2-yl)-3-(9H-pyrimido-[4,5-b]indol-7-yl)benzamide | Ex. 50 | 400 |
| 58 | Cl | 3-CF$_3$C$_6$H$_4$ | 4-chloro-3-(9H-pyrimido-[4,5-b]indol-7-yl)-N-[3-(trifluoromethyl)phenyl]-benzamide | Ex. 50 | 467 |
| 59 | H | 3-CF$_3$C$_6$H$_4$ | 3-(9H-pyrimido[4,5-b]indol-7-yl)-N-[3-(trifluoromethyl)-phenyl]benzamide | Ex. 50 | 433 |
| 60 | CH$_3$O | 3-CF$_3$C$_6$H$_4$ | 4-methoxy-3-(9H-pyrimido-[4,5-b]indol-7-yl)-N-[3-(trifluoromethyl)phenyl]-benzamide | Ex. 50 | 463 |
| 61 | CH$_3$ | 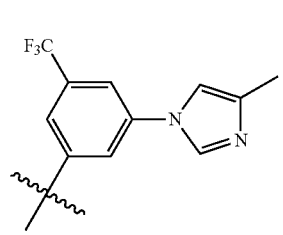 [SMILES: *c1cc(-n2cnc(C)c2)cc(C(F)(F)F)c1] | 4-methyl-3-(9H-pyrimido-[4,5-b]indol-7-yl)-N-[5-(trifluoromethyl)-1,3,4-thiadiazol-2-yl]benzamide | Ex. 50 | 455 |
| 62 | CH$_3$ | | 4-methyl-N-[3-(4-methyl-1H-imidazol-1-yl)-5-(trifluoro-methyl)phenyl]-3-(9H-pyrimido[4,5-b]indol-7-yl)-benzamide | Ex. 50 | 527 |
| 63 | CH$_3$ | (R)—C$_6$H$_5$CH(CH$_3$) | 4-methyl-N-[(1R)-1-phenylethyl]-3-(9H-pyrimido[4,5-b]indol-7-yl)benzamide | Ex. 50 | 407 |
| 64 | CH$_3$ | (S)—C$_6$H$_5$CH(CH$_3$) | 4-methyl-N-[(1S)-1-phenylethyl]-3-(9H-pyrimido[4,5-b]indol-7-yl)benzamide | Ex. 50 | 407 |
| 65 | CH$_3$ | 3-SF$_5$C$_6$H$_4$ | 4-methyl-N-[3-(pentafluoro-λ(6)-sulfanyl)phenyl]-3-(9H-pyrimido[4,5-b]indol-7-yl)-benzamide | Ex. 50 | 505 |

TABLE 4

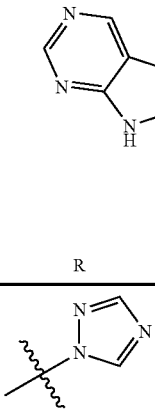

| Ex. No. | R | Name | Prep. | MS |
|---|---|---|---|---|
| 73 | 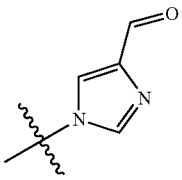 [SMILES: *n1cnc(C=O)c1] | N-[6-methyl-5-(9H-pyrimido[4,5-b]indol-7-yl)pyridin-3-yl]-3-(1H-1,2,4-triazol-1-yl)-5-(trifluoromethyl)benzamide bis(trifluoroacetate) | Ex. 72 | 515 |
| 74 | 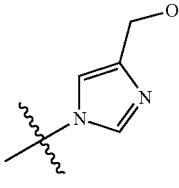 | 3-(4-formyl-1H-imidazol-1-yl)-N-[6-methyl-5-(9H-pyrimido[4,5-b]indol-7-yl)pyridin-3-yl]-5-(trifluoromethyl)benzamide bis(trifluoroacetate) | Ex. 72 | 542 |
| 75 |  | 3-[4-(hydroxymethyl)-1H-imidazol-1-yl]-N-[6-methyl-5-(9H-pyrimido[4,5-b]indol-7-yl)pyridin-3-yl]-5-(trifluoromethyl)benzamide tris(trifluoroacetate) (salt) | Ex. 72 | 544 |
| 76 | —NH(CH$_2$)$_2$NMe$_2$ | 3-[2-(dimethylamino)ethyl]amino-N-[6-methyl-5-(9H-pyrimido[4,5-b]indol-7-yl)pyridin-3-yl]-5-(trifluoromethyl)benzamide tris(trifluoroacetate) | Ex. 72 | 534 |
| 77 | NH(CH$_2$)$_3$NMe$_2$ | 3-[3-(dimethylamino)propyl]amino-N-[6-methyl-5-(9H-pyrimido[4,5-b]indol-7-yl)pyridin-3-yl]-5-(trifluoromethyl)benzamide tris(trifluoroacetate) | Ex. 72 | 548 |

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 μM for JAK1, 30 μM for JAK2 and 3 μM for JAK3. Reactions were carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). Compounds having an IC$_{50}$ of 10 μM or less for any of the above-mentioned JAK targets were considered active.

Example B

Cellular Assays

One or more compounds herein were tested for inhibitory activity of JAK targets according to at least one of the following cellular assays.

Cancer cell lines dependent on cytokines and hence JAK/STAT signal transduction, for growth, were plated at 6000 cells per well (96 well plate format) in RPM 1640, 10% FBS, and 1 nG/mL of appropriate cytokine. Compounds were added to the cells in DMSO/media (final concentration 0.2% DMSO) and incubated for 72 hours at 37° C., 5% CO$_2$. The effect of compound on cell viability was assessed using the CellTiter-Glo Luminescent Cell Viability Assay (Promega) followed by TopCount (Perkin Elmer, Boston, Mass.) quantitation. Potential off-target effects of compounds were measured in parallel using a non-JAK driven cell line with the same assay readout. Compounds having an IC$_{50}$ of 10 μM or less with selectivity for JAK driven proliferation were considered active. All experiments were performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of $2 \times 10^6$ cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol* J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. BCR-ABL1) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today*. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2): 116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds was given throughout the sensitization and challenge phases (day −1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be or have been evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al., Wiley Press.; *Methods in Molecular Biology*: Vol. 225, Inflammation Protocols., Winyard, P. G. and Willoughby, D. A., Humana Press, 2003.).

Example F

ABL1 and T315I Cell Based Assays

One or more compounds herein were tested for inhibitory activity of ABL1 targets according to at least one of the following cellular assays.

Cancer cell lines dependent on ABL1 kinase activity for proliferation and/or survival were plated at 3000 cells per well (96 well plate format) in RPMI 1640, and 10% FBS. Compounds were added to the cells in DMSO/media (final concentration 0.2% DMSO) and incubated for 72 hours at 37° C., 5% $CO_2$. The effect of compound on cell viability was assessed using the CellTiter-Glo Luminescent Cell Viability Assay (Promega) followed by TopCount (Perkin Elmer, Boston, Mass.) quantitation. ABL1-dependent cell lines can include those naturally dependent on ABL1 activity or those engineered to be dependent on ABL1 activity or those engineered to be dependent on ABL1 activity (e.g. BaF/3 cells). The latter can be generated using wild-type ABL1 or mutant ABL1 (such as T315I ABL1) so that the activity of compounds can be assessed against different variants of the ABL1 kinase. Potential off-target effects of compounds were measured in parallel using a non-ABL1 driven cell line with the same assay readout. Compounds having an $IC_{50}$ of 10 M or less with selectivity for JAK driven proliferation were considered active. All experiments were performed in duplicate or greater.

The above cell lines can also be used to examine the effects of compounds on phosphorylation of ABL1 and/or ABL1 substrates, such as STAT proteins, Akt, Erk, or Crk1. These experiments can be performed following incubation of cells with compound(s) for varying period of time (usually 10 minutes to 4 hours), depending on a number of factors (e.g. the half-life of the phosphor-proteins of interest). Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on both cancerous and normal cells.

These same cell lines can be used to examine the effects of inhibiting both ABL and JAK kinases with unique or the same compound. For instance, BaF/3 cells expressing BCR-ABL1 (mutant or wild-type) can be used to evaluate the impact of compounds on the growth, survival, and signaling of cells driven by the ABL1-kinase. However, if these same cells are grown in the presence of specific cytokines (e.g. IL-3) that activate JAK kinases, the impact of compounds can be assessed in cells in which both ABL and JAK kinases contribute to the tumor cell viability and proliferation.

Example G

ABL1 and T315I ABL1 HTRF Assay

Compounds herein described were tested for inhibitory activity of ABL1 kinase (wild-type and T315I mutant) as described below. The catalytic domains of ABL1 kinases (residues 27 to the C-termini) were N-terminal His tagged and expressed by baculovirus in insect cells and purified. These were purchased in purified form from Upstate Cell Signaling Solutions. ABL1 and T315I ABL1 catalyze the phosphorylation of p28. The phosphorylated p28 is detected by Homogeneous Time Resolved Fluorescence (HTRF). $IC_{50}$s of compounds were measured for each kinase in the reactions that contain: 1-2 nM ABL1 or T315I ABL1, 500 nM peptide, 35 µM ATP for ABL1 and 10 µM ATP for T315I ABL1, 2.0% DMSO in assay buffer containing 50 mM Tris, pH 7.8, 100 mM NaCl, 10 mM $MgCl_2$, 5 mM DTT, 0.6 mg/mL BSA. Reactions proceed at room temperature for one and half hour and were stopped by adding, 20 µL additional 50 mM NaCl, 0.4 mg/mL BSA, 45 mM EDTA, 200 nM SA-APC, 4 nM Eu-Py20 in assay buffer. The plates were incubated at room temperature for 40 min and HTRF was then measured on a plate reader.

Other kinase assays may be run in similar fashion using commercially available kinases and substrates and/or through contract service providers such as Invitrogen, Cerep, or Upstate Biosciences.

Example H

In Vivo Anti-Tumor Efficacy

Compounds herein can be evaluated in human tumor xenograft models in immune competent or compromised mice. For example, a tumorigenic variant of the BaF/3 cell line that has been transformed with BCR-ABL1 (wild-type or mutant) can be used to inoculate Balb/c or Balb/c nu/nu mice subcutaneously or intravenously. Tumor cell bearing animals can then be randomized into drug or vehicle treatment groups and different doses of compounds can be administered by any number of the usual routes including oral, i.p. or continuous infusion using implantable pumps. Tumor cell growth is followed over time using calipers (for subcutaneous inoculations) and the survival of animals can also be tracked (for intravenous inoculations). Further, tumor cell samples can be harvested at any time after the initiation of treatment for analysis as described above to evaluate compound effects on kinase activity (JAK, ABL, or other) and downstream signaling pathways. In addition, selectivity of the compound(s) can be assessed using xenograft tumor models that are driven by other 'off-target' kinases.

Example I

Biological Data

Select activity data according to the indicated assay is provided below for certain compounds of the invention in Tables 1 and 2.

TABLE 1

IC$_{50}$ data$^a$

| Example | EXAMPLE A HTS-JAK2 HTRF-2 IC$_{50}$ (nM) | EXAMPLE B JAK2_INA61 IC$_{50}$ (nM) | EXAMPLE A JAK2-JAK1 HTRF-2 IC$_{50}$ (nM) | EXAMPLE A JAK2-JAK3 HTRF-2 IC$_{50}$ (nM) | EXAMPLE F JAK2-TF1-BC RABL1 IC$_{50}$ (nM) |
|---|---|---|---|---|---|
| 1 | + | + | + | + | + |
| 2 | + | ++ | + | + | + |
| 3 | + | + | + | + | + |
| 4 | + | − | + | + | + |
| 5 | + | − | + | + | + |
| 6 | + | ++ | + | + | + |
| 7 | +++ | +++ | + | + | ++ |
| 8 | + | − | + | + | + |
| 9 | + | − | + | + | + |
| 10 | + | − | + | + | + |
| 11 | ++ | +++ | + | + | + |
| 12 | +++ | +++ | + | + | ++ |
| 13 | + | + | + | + | + |
| 14 | + | +++ | + | +++ | ++ |
| 15 | + | + | + | + | + |
| 16 | + | ++ | + | + | + |
| 17 | + | − | + | + | + |
| 18 | + | − | + | + | + |
| 19 | + | + | + | + | + |
| 20 | + | − | + | + | + |
| 21 | + | − | + | + | + |
| 22 | + | − | + | + | + |
| 23 | + | − | + | + | + |
| 24 | + | − | + | + | + |
| 25 | + | − | + | + | + |
| 26 | + | − | + | + | + |
| 27 | + | − | + | + | + |
| 28 | + | ++ | + | + | + |
| 29 | + | − | + | + | + |
| 30 | + | − | + | + | + |
| 31 | + | − | + | + | + |
| 32 | + | − | + | + | + |
| 33 | + | − | + | + | + |
| 34 | + | − | + | + | + |
| 35 | + | − | + | + | + |
| 36 | + | − | + | + | + |
| 37 | + | − | + | + | + |
| 38 | + | ++ | + | + | + |
| 40 | + | + | + | ++ | + |
| 42 | + | +++ | + | ++ | + |
| 43 | + | ++ | +++ | + | + |
| 44 | +++ | +++ | + | + | ++ |
| 45 | +++ | +++ | + | +++ | ++ |
| 46 | + | +++ | + | +++ | + |
| 47 | ++ | +++ | + | + | + |
| 48 | +++ | ++ | + | ++ | + |
| 51 | + | +++ | + | +++ | + |
| 52 | + | ++ | + | + | + |
| 53 | + | ++ | + | + | + |
| 54 | + | ++ | + | + | + |
| 55 | +++ | ++ | +++ | + | ++ |
| 56 | +++ | +++ | +++ | + | + |
| 57 | +++ | +++ | + | +++ | + |
| 58 | + | ++ | + | + | + |
| 59 | + | +++ | + | +++ | ++ |
| 60 | + | +++ | + | ++ | + |
| 61 | +++ | +++ | +++ | + | ++ |
| 62 | + | ++ | + | + | + |
| 63 | +++ | +++ | +++ | ++ | ++ |
| 64 | +++ | +++ | +++ | + | ++ |
| 65 | + | ++ | + | + | + |
| 66 | + | ++ | + | + | + |
| 67 | + | − | + | + | + |
| 68 | + | +++ | + | + | + |

TABLE 1-continued

IC$_{50}$ data[a]

| Example | EXAMPLE A HTS-JAK2 HTRF-2 IC$_{50}$ (nM) | EXAMPLE B JAK2__INA61 IC$_{50}$ (nM) | EXAMPLE A JAK2-JAK1 HTRF-2 IC$_{50}$ (nM) | EXAMPLE A JAK2-JAK3 HTRF-2 IC$_{50}$ (nM) | EXAMPLE F JAK2-TF1-BC RABL1 IC$_{50}$ (nM) |
|---|---|---|---|---|---|
| 70 | + | ++ | + | + | + |
| 71 | + | − | + | + | + |
| 72 | + | − | + | + | + |
| 73 | + | − | + | + | + |
| 74 | + | − | + | + | + |
| 75 | + | − | + | + | + |
| 76 | + | − | + | + | + |
| 77 | + | − | + | + | + |

[a] + = ≤500 nM; ++ = 500-1000 nM; +++ = >1000 nM

TABLE 2

| Example | EXAMPLE G WT Abl IC$_{50}$ (nM) | EXAMPLE G T315I Abl IC$_{50}$ (nM) | EXAMPLE H TF1_BCRABL IC$_{50}$ (nM) |
|---|---|---|---|
| 40 | <200 | <190 | <180 |
| 52 | <200 | <190 | <180 |
| 58 | <200 | <190 | <180 |
| 66 | <200 | <190 | <180 |
| 26 | <200 | <190 | <180 |

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:
1. A compound of Formula IIC:

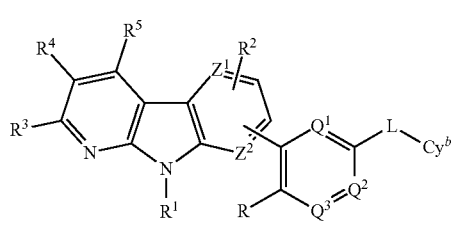

IIC or a pharmaceutically acceptable salt form thereof, wherein:

R is selected from H, halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^i$)NR$^{c1}$R$^{d1}$, NR$^{c1}$C(=NR$^i$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, S(O)R$^{b1}$, S(O)NR$^{c1}$R$^{d1}$, S(O)$_2$R$^{b1}$, and S(O)$_2$NR$^{c1}$R$^{d1}$; wherein said C$_{1-6}$ alkyl, C$_{2-6}$ alkenyl, or C$_{2-6}$ alkynyl is optionally substituted with 1, 2, 3, 4, or 5 substituents selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^i$)NR$^{c1}$R$^{d1}$, NR$^{c1}$C(=NR$^i$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, S(O)R$^{b1}$, S(O)NR$^{c1}$R$^{d1}$, S(O)$_2$R$^{b1}$, and S(O)$_2$NR$^{c1}$R$^{d1}$;

Q$^1$, Q$^2$, and Q$^3$ are independently selected from CR$^Q$ and N;

R$^Q$ is independently selected from H, halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^i$)NR$^{c1}$R$^{d1}$, NR$^{c1}$C(=NR$^i$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, S(O)R$^{b1}$, S(O)NR$^{c1}$R$^{d1}$, S(O)$_2$R$^{b1}$, and S(O)$_2$NR$^{c1}$R$^{d1}$; wherein said C$_{1-6}$ alkyl, C$_{2-6}$ alkenyl, or C$_{2-6}$ alkynyl is optionally substituted with 1, 2, 3, 4, or 5 substituents selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^i$)NR$^{c1}$R$^{d1}$, NR$^{c1}$C(=NR$^i$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, S(O)R$^{b1}$, S(O)NR$^{c1}$R$^{d1}$, S(O)$_2$R$^{b1}$, and S(O)$_2$NR$^{c1}$R$^{d1}$;

Cy$^b$ is a substituted aryl or substituted heteroaryl ring according to Formula IF:

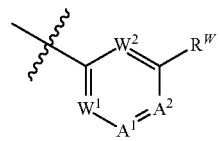

IF wherein:

W$^1$ and W$^2$ are independently selected from CR$^W$ and N;

A$^1$ and A$^2$ are independently selected from CR$^W$ and N; or the group A$^1$=A$^2$ is S, O, or NH; and each R$^W$ is independently selected from H, halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$)NR$^{c2}$R$^{d2}$, NR$^{c2}$C(=NR$^i$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, or C$_{2-6}$ alkynyl is optionally substituted with 1, 2, 3, 4, or 5 substituents selected from halo, C$_{1-6}$ alkyl, C$_{2-6}$ alkenyl, C$_{2-6}$ alkynyl, Cy, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^i$)NR$^{c2}$R$^{d2}$, NR$^{c2}$C(=NR$^i$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S (O)R$^{b2}$, NR$^{c2}$S(O)$_2$R$^{b2}$, NR$^{c2}$C(O)NR$^{c2}$R$^{d2}$, NR$^{c2}$S(O)R$^{b2}$, NR$^{c2}$S(O)$_2$R$^{b2}$, S(O)R$^{b2}$, S(O)NR$^{c2}$R$^{d2}$, S(O)$_2$R$^{b2}$, and S(O)$_2$NR$^{c2}$R$^{d2}$;

L is a divalent moiety selected from C$_{1-6}$ alkylene, C$_{2-6}$ alkenylene, C$_{2-6}$ alkynylene, (C$_{1-6}$ alkylene)$_p$-(C$_{3-10}$ cycloalkylene)-(C$_{1-6}$ alkylene)$_q$, (C$_{1-6}$ alkylene)$_p$-(C$_{3-10}$ heterocycloalkylene)-(C$_{1-6}$ alkylene)$_q$, (C$_{1-6}$ alkylene)$_p$-(C$_{6-10}$ arylene)-(C$_{1-6}$ alkylene)$_q$, (C$_{1-6}$ alkylene)$_p$-(C$_{3-10}$ heteroarylene)-(C$_{1-6}$ alkylene)$_q$, (C$_{1-6}$ alkylene)$_p$-O-(C$_{1-6}$ alkylene)$_q$, (C$_{1-6}$ alkylene)$_p$-S-(C$_{1-6}$ alkylene)$_q$, (C$_{1-6}$ alkylene)$_p$-NR$^{c3}$—(C$_{1-6}$ alkylene)$_q$, (C$_{1-6}$ alkylene)$_p$-C(O)—(C$_{1-6}$ alkylene)$_q$, (C$_{1-6}$ alkylene)$_p$-OC(O)—(C$_{1-6}$ alkylene)$_q$, (C$_{1-6}$ alkylene)$_p$-C(O)NR$^{c3}$—(C$_{1-6}$ alkylene)$_q$, (C$_{1-6}$ alkylene)$_p$-OC(O)NR$^{c3}$—(C$_{1-6}$ alkylene)$_q$, (C$_{1-6}$ alkylene)$_p$-S(O)—(C$_{1-6}$ alkylene)$_q$, (C$_{1-6}$ alkylene)$_p$-S(O)$_2$—(C$_{1-6}$ alkylene)$_q$, (C$_{1-6}$ alkylene)$_p$-S(O)NR$^{c3}$—(C$_{1-6}$ alkylene)$_q$, (C$_{1-6}$ alkylene)$_p$-S(O)$_2$NR$^{c3}$—(C$_{1-6}$ alkylene)$_q$, (C$_{1-6}$ alkylene)$_p$-NR$^{c3}$C(O)NR$^{d3}$—(C$_{1-6}$ alkylene)$_q$, (C$_{1-6}$ alkylene)$_p$-NR$^{c3}$S(O)NR$^{d3}$—(C$_{1-6}$ alkylene)$_q$, and (C$_{1-6}$ alkylene)$_p$-NR$^{c3}$S(O)$_2$NR$^{d3}$—(C$_{1-6}$ alkylene)$_q$, wherein each of the C$_{1-6}$ alkylene, C$_{2-6}$ alkenylene, C$_{2-6}$ alkynylene, cycloalkylene, arylene, heterocycloalkylene, and heteroarylene is optionally substituted by 1, 2 or 3 substituents independently selected from C$_{1-4}$ alkyl, C$_{2-4}$ alkenyl, C$_{2-4}$ alkynyl, C$_{1-4}$ hydroxyalkyl, C$_{1-4}$ cyanoalkyl, aryl, heteroaryl, cycloalkyl, heterocycloalkyl, halo, CN, NO$_2$, SCN, OH, C$_{1-4}$ haloalkyl, halosulfanyl, C$_{1-4}$ alkoxy-C$_{1-4}$ alkyl, C$_{1-4}$ alkoxy, C$_{1-4}$ haloalkoxy, amino, C$_{1-4}$ alkylamino, and C$_{2-8}$ dialkylamino;

wherein L is oriented in either direction with respect to its attachment to Cy$^b$ and the ring containing Q$^1$, Q$^2$, and Q$^3$;

Z$^1$ is CR$^6$;

Z$^2$ is CR$^7$;

R$^1$ is selected from H, C$_{1-6}$ alkyl, C(O)C$_{1-6}$ alkyl, and C(O) aryl;

R$^2$, R$^3$, R$^4$, and R$^5$ are independently selected from H, halo, C$_{1-6}$ alkyl, C$_{2-6}$ alkenyl, C$_{2-6}$ alkynyl, Cy$^1$, C$_{1-6}$ haloalkyl, halosulfanyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^i$)NR$^{c4}$R$^{d4}$, NR$^{c4}$C(=NR$^i$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{2-6}$ alkenyl, or C$_{2-6}$ alkynyl is optionally substituted with 1, 2, 3, 4, or 5 substituents selected from CN, NO$_2$, Cy$^1$, Cy$^1$-(C$_{1-6}$ alkyl)-, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, C(=NR$^i$)NR$^{c4}$R$^{d4}$, NR$^{c4}$C(=NR$^i$)NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

R$^6$ is H;

R$^7$ is H;

Cy, Cy$^1$, and Cy$^2$ are independently selected from aryl, heteroaryl, cycloalkyl, and heterocycloalkyl, each optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, N$_3$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)NR$^{c5}$R$^{d5}$, NR$^{c5}$C(O)OR$^{a5}$, C(=NR$^i$)NR$^{c5}$R$^{d5}$, NR$^{c5}$C(=NR$^i$)NR$^{c5}$R$^{d5}$, P(R$^{f5}$)$_2$, P(OR$^{e5}$)$_2$, P(O)R$^{e5}$R$^{f5}$, P(O)OR$^{e5}$OR$^{f5}$, S(O)R$^{b5}$, S(O)NR$^{c5}$R$^{d5}$, and S(O)$_2$NR$^{c5}$R$^{d5}$, wherein said C$_{1-6}$ alkyl, C$_{2-6}$ alkenyl, and C$_{2-6}$ alkynyl are each optionally substituted by 1, 2, or 3 substituents independently selected from halo, C$_{1-6}$ haloalkyl, halosulfanyl, CN, NO$_2$, N$_3$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^i$)NR$^{c5}$R$^{d5}$, NR$^{c5}$C(=NR$^i$)NR$^{c5}$R$^{d5}$, P(R$^{f5}$)$_2$, P(OR$^{e5}$)$_2$, P(O)R$^{e5}$R$^{f5}$, P(O)OR$^{e5}$OR$^{f5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{a1}$, R$^{a2}$, and R$^{a4}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, and C(O)—C$_{1-7}$ hydrocarbyl, wherein said C$_{1-6}$ alkyl, C$_{2-6}$ alkenyl, C$_{1-7}$ hydrocarbyl, or C$_{2-6}$ alkynyl is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{b1}$, R$^{b2}$, and R$^{b4}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, wherein said C$_{1-6}$ alkyl, C$_{2-6}$ alkenyl, or C$_{2-6}$ alkynyl is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{c1}$, R$^{c2}$, and R$^{c4}$ are independently selected from H, Cy$^2$, —(C$_{1-6}$ alkyl)-Cy$^2$, C$_{1-6}$ alkyl, C$_{1-6}$ haloalkyl, C$_{1-6}$ hydroxyalkyl, C$_{2-6}$ alkenyl, C$_{2-6}$ alkynyl, wherein said C$_{1-6}$ alkyl, C$_{2-6}$ alkenyl, or C$_{2-6}$ alkynyl, is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{d1}$, R$^{d2}$, and R$^{d4}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, wherein said C$_{1-6}$ alkyl, C$_{2-6}$ alkenyl, or C$_{2-6}$ alkynyl, is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl; or, one or more of R$^{c1}$ and R$^{d1}$, R$^{c2}$ and R$^{d2}$, and R$^{c4}$ and R$^{d4}$ together with the N atom to which they are attached, optionally form a 4-, 5-, 6- or 7-membered heterocycloalkyl group or heteroaryl group, each optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{c3}$ and R$^{d3}$ are independently selected from H, Cy$^2$, —(C$_{1-6}$ alkyl)-Cy$^2$, C$_{1-6}$ alkyl, C$_{1-6}$ haloalkyl, C$_{2-6}$ alkenyl, C$_{2-6}$ alkynyl, wherein said C$_{1-6}$ alkyl, C$_{2-6}$ alkenyl, or C$_{2-6}$ alkynyl is optionally substituted with 1, 2, or 3 substituents independently selected from OH, C$_{1-6}$ alkoxy, CN, amino, alkylamino, dialkylamino, halo, C$_{1-6}$ alkyl, C$_{1-6}$ haloalkyl, halosulfanyl, aryl, arylalkyl, heteroaryl, heteroarylalkyl, cycloalkyl, and heterocycloalkyl;

R$^{a5}$ is H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ halo alkoxy;

$R^{b5}$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{e5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; or $R^{e5}$ and $R^{d5}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{e5}$ is H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

$R^{f5}$ is H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl;

$R^i$ is H, CN, $NO_2$, $C(O)NH_2$, or $C_{1-6}$ alkyl;

p is 0 or 1; and q is 0 or 1.

2. A compound of claim 1, or pharmaceutically acceptable salt thereof, wherein $R^1$ is H, $C_{1-6}$ alkyl, or $C(O)C_{1-6}$ alkyl.

3. A compound of claim 1, or pharmaceutically acceptable salt thereof, wherein R is selected from H, halo, CN, $C_{1-6}$ alkyl and $OR^{a1}$.

4. A compound of claim 1, or pharmaceutically acceptable salt thereof, wherein $Q^3$ is $CR^Q$.

5. A compound of claim 1, or pharmaceutically acceptable salt thereof, wherein $Q^3$ is N.

6. A compound of claim 1, or pharmaceutically acceptable salt thereof, wherein $Cy^b$ is a substituted aryl according to Formula IG:

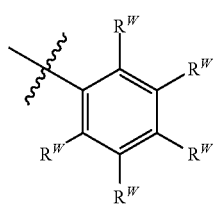

IG wherein each $R^W$ is independently selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, or $C_{2-6}$ alkynyl is optionally substituted with 1, 2, 3, 4, or 5 substituents selected from halo, $C_{1-6}$ alkyl, $C_{2-6}$ alkenyl, $C_{2-6}$ alkynyl, Cy, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^i)NR^{c2}R^{d2}$, $NR^{c2}C(=NR^i)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}C(O)NR^{c2}R^{d2}$, $NR^{c2}S(O)R^{b2}$, $NR^{c2}S(O)_2R^{b2}$, $S(O)R^{b2}$, $S(O)NR^{c2}R^{d2}$, $S(O)_2R^{b2}$, and $S(O)_2NR^{c2}R^{d2}$.

7. A compound of claim 1, or pharmaceutically acceptable salt thereof, wherein L is C(O)NH.

8. A composition comprising a compound according to claim 1, or pharmaceutically acceptable salt thereof, and at least one pharmaceutically acceptable carrier.

9. A compound of claim 1, or a pharmaceutically acceptable salt thereof, wherein the compound is 4-methyl-3-(9H-pyrido[2,3-b]indol-7-yl)-N-[3-(trifluoromethyl)phenyl]benzamide.

10. A method of treating myeloproliferative disorder in a patient, the method comprising, administering to said patient a therapeutically effective amount of a compound of claim 1 or a pharmaceutically acceptable salt thereof.

11. The method of claim 10, wherein said myeloproliferative disorder (MPD) is polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), idiopathic myelofibrosis (IMF), or systemic mast cell disease (SMCD).

12. A method of treating acute lymphoblastic leukemia (ALL), chronic myelomonocytic leukemia (CMML), or chronic myeloid leukemia (CML), in a patient, the method comprising, administering to said patient a therapeutically effective amount of a compound of claim 1, or a pharmaceutically acceptable salt thereof.

13. A method of treating Type I diabetes in a patient, the method comprising, administering to said patient a therapeutically effective amount of a compound of claim 1, or a pharmaceutically acceptable salt thereof.

14. A method of treating psoriasis in a patient, the method comprising, administering to said patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 8,841,318 B2  Page 1 of 1
APPLICATION NO. : 13/834040
DATED : September 23, 2014
INVENTOR(S) : Argyrios G. Arvanitis et al.

It is certified that error appears in the above-identified patent and that said Letters Patent is hereby corrected as shown below:

On The Title Page, Item (56) Other Publication

Page 2, Col. 1, Line 23, delete "96,," and insert -- 96, --.

Page 2, Col. 2, Line 34, delete ""Piramido" and insert -- "Pyrimido --.

Page 2, Col. 2, Line 35, delete "Gurase" and insert -- Gyrase --.

Claims

Col. 104, Line 52, claim 1, delete "$A^1=A^2$" and insert -- $A^1\!=\!A^2$ --.

Col. 105, Line 11-12, claim 1, delete "$(C_{1-6} \text{ alkylene})_p$" and insert -- $(C_{1-6} \text{ alkylene})_p$ --.

Col. 105, Line 12, claim 1, delete "$(C_{1-6} \text{ alkylene})_p$" and insert -- $(C_{1-6} \text{ alkylene})_p$ --.

Col. 105, Line 13, claim 1, delete "$(C_{1-6} \text{ alkylene})_p$" and insert -- $(C_{1-6} \text{ alkylene})_p$ --.

Col. 105, Line 15, claim 1, delete "$(C_{1-6} \text{ alkylene})_p$" and insert -- $(C_{1-6} \text{ alkylene})_p$ --.

Col. 105, Line 56, claim 1, delete "4" and insert -- 4, --.

Col. 107, Line 5, claim 1, delete "halo alkoxy;" and insert -- haloalkoxy; --.

Signed and Sealed this
Twenty-sixth Day of January, 2016

Michelle K. Lee
*Director of the United States Patent and Trademark Office*